United States Patent
Bebernitz et al.

(10) Patent No.: US 7,750,020 B2
(45) Date of Patent: Jul. 6, 2010

(54) SULFONAMIDE-THIAZOLPYRIDINE DERIVATIVES AS GLUCOKINASE ACTIVATORS USEFUL THE TREATMENT OF TYPE 2 DIABETES

(75) Inventors: Gregory Raymond Bebernitz, Stow, MA (US); Ramesh Chandra Gupta, Ahmedabad (IN); Vikrant Vijaykumar Jagtap, Gandhinagar (IN); Appaji Baburao Mandhare, Ahmedabad (IN); Davinder Tuli, Gandhinagar (IN)

(73) Assignee: Novartis AG, Basel (CH)

( * ) Notice: Subject to any disclaimer, the term of this patent is extended or adjusted under 35 U.S.C. 154(b) by 87 days.

(21) Appl. No.: 11/547,046

(22) PCT Filed: Apr. 1, 2005

(86) PCT No.: PCT/EP2005/003456

§ 371 (c)(1), (2), (4) Date: Jun. 22, 2007

(87) PCT Pub. No.: WO2005/095418

PCT Pub. Date: Oct. 13, 2005

(65) Prior Publication Data

US 2008/0103167 A1 May 1, 2008

Related U.S. Application Data

(60) Provisional application No. 60/559,184, filed on Apr. 2, 2004.

(51) Int. Cl.
*A61K 31/437* (2006.01)
*A61K 31/429* (2006.01)
*C07D 513/04* (2006.01)
*C07D 31/4365* (2006.01)

(52) U.S. Cl. ........................... 514/301; 546/114
(58) Field of Classification Search ................. 546/114; 514/301
See application file for complete search history.

(56) References Cited

U.S. PATENT DOCUMENTS

| | | |
|---|---|---|
| 6,320,050 B1 | 11/2001 | Bizzarro et al. |
| 6,353,111 B1 | 3/2002 | Corbett et al. |
| 6,369,232 B1 | 4/2002 | Sidduri |
| 6,384,220 B2 | 5/2002 | Corbett et al. |
| 6,388,071 B2 | 5/2002 | Mahaney |
| 6,388,088 B1 | 5/2002 | Sidduri |
| 6,433,188 B1 | 8/2002 | Corbett et al. |
| 6,441,184 B1 | 8/2002 | Corbett et al. |
| 6,448,399 B1 | 9/2002 | Corbett et al. |
| 6,486,184 B2 | 11/2002 | Kester et al. |
| 6,489,485 B2 | 12/2002 | Bizzarro et al. |
| 6,528,543 B1 | 3/2003 | Bizzarro et al. |
| 6,545,155 B2 | 4/2003 | Corbett et al. |
| 6,583,288 B2 | 6/2003 | Goodnow et al. |
| 6,608,218 B2 | 8/2003 | Kester et al. |
| 6,610,846 B1 | 8/2003 | Bizzarro et al. |
| 6,784,298 B2 | 8/2004 | Goodnow et al. |
| 2001/0039344 A1 | 11/2001 | Bizzarro et al. |
| 2001/0051731 A1 | 12/2001 | Bizzarro et al. |
| 2001/0053851 A1 | 12/2001 | Mahaney |
| 2001/0056191 A1 | 12/2001 | Goodnow, Jr. et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0082260 A1 | 6/2002 | Guertin |
| 2002/0103241 A1 | 8/2002 | Corbett et al. |
| 2002/0107396 A1 | 8/2002 | Corbett et al. |
| 2002/0198200 A1 | 12/2002 | Kester et al. |
| 2003/0219887 A1 | 11/2003 | Corbett et al. |
| 2003/0225283 A1 | 12/2003 | Corbett et al. |
| 2003/0225286 A1 | 12/2003 | Goodnow, Jr. et al. |
| 2004/0014968 A1 | 1/2004 | Bizzarro et al. |
| 2004/0067939 A1 | 4/2004 | Corbett |
| 2004/0147748 A1 | 7/2004 | Chen et al. |
| 2004/0186290 A1 | 9/2004 | Fyfe et al. |
| 2005/0282851 A1 | 12/2005 | Bebernitz |
| 2007/0265297 A1 | 11/2007 | Bebernitz |
| 2008/0312256 A1 | 12/2008 | Bebernitz |
| 2008/0318948 A1 | 12/2008 | Bebernitz |

FOREIGN PATENT DOCUMENTS

| | | |
|---|---|---|
| DE | 10259786 A1 | 7/2003 |
| GB | 2385328 A | 8/2003 |
| WO | 0058293 A2 | 10/2000 |
| WO | 0144216 A1 | 6/2001 |

(Continued)

OTHER PUBLICATIONS

Desai et al., Diabetes, (Oct. 2001) vol. 50, No. 10, pp. 2287-2295.*

(Continued)

*Primary Examiner*—D. Margaret Seaman
*Assistant Examiner*—Niloofar Rahmani
(74) *Attorney, Agent, or Firm*—Theresa Devlin

(57) ABSTRACT

The present invention provides compounds of the formula (I), which are activators of glucokinase activity and, thus, may be employed as therapeutic agents for the treatment of glucokinase mediated conditions. Accordingly, the compounds of formula (I) may be employed for the prevention and the treatment of impaired glucose tolerance, Type 2 diabetes and obesity.

(I)

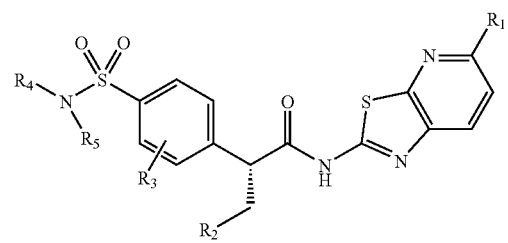

13 Claims, No Drawings

FOREIGN PATENT DOCUMENTS

| | | |
|---|---|---|
| WO | 0183465 A2 | 11/2001 |
| WO | 0183478 A2 | 11/2001 |
| WO | 0185706 A1 | 11/2001 |
| WO | 0185707 A1 | 11/2001 |
| WO | 0208209 A1 | 1/2002 |
| WO | 0214312 A1 | 2/2002 |
| WO | 0246173 | 6/2002 |
| WO | 0248106 A2 | 6/2002 |
| WO | 03/015774 A1 | 2/2003 |
| WO | 03055482 A1 | 7/2003 |
| WO | 03080585 A1 | 10/2003 |
| WO | 03095438 A1 | 11/2003 |
| WO | 03097824 A1 | 11/2003 |
| WO | 2004002481 A1 | 1/2004 |
| WO | 2004050645 * | 6/2004 |
| WO | 2004050645 A1 | 6/2004 |
| WO | 2004052869 A1 | 6/2004 |
| WO | 2004063179 A1 | 7/2004 |
| WO | 2004063194 A1 | 7/2004 |
| WO | 2004072031 | 8/2004 |
| WO | 2004072066 A1 | 8/2004 |
| WO | 2004076420 A1 | 9/2004 |
| WO | 2004081001 A1 | 9/2004 |
| WO | 2005103021 A1 | 11/2005 |
| WO | 2006016194 A1 | 2/2006 |
| WO | 2006058923 A1 | 6/2006 |
| WO | 2007041365 A2 | 4/2007 |
| WO | 2007041366 A1 | 4/2007 |

OTHER PUBLICATIONS

Brocklehurst et al., "Stimulation of Hepatocyte Glucose Metabolism by Novel Small Molecule Glucokinase Activators" Diabetes 53:535-541 (2004).

Guertin et al., "Small Molecule Glucokinase Activators as Glucose Lowering Agents: A New Paradigm for Diabetes Therapy" Current Medicinal Chemistry 13:1839-1843(2006).

McKerrecher et al., "Discovery, synthesis and biological evaluation of novel glucokinase activators" Bioorganic & Medicinal Chemistry Letters 15:2103-2106 (2005).

Leighton et al., "Small molecule glucokinase activators as novel anti-diabetic agents" Biochem Soc Trans 33(2) 371-374 (2005).

Coope et al., "Predictive blood glucose lowering efficacy by Glucokinase activators in high fat fed female Zucker rats" British Journal of Pharmacology:1-8 (2006).

"Tweaking the Glucose Sensor: Adjusting Glucokinase Activity with Activator Compounds" Endocrinology 146 (9):3693-3695 (Sep. 2005).

Futamura et al., "An Allosteric Activator of Glucokinase Impairs The Interaction of Glucokinase and Glucokinase Regulatory Protein and Regulates Glucose Metabolism," The Journal of Biological Chemistry, Manuscript M605186200 (Oct. 6, 2006).

McKerrecher et al., "Design of a potent, soluble glucokinase activator with excellent in vivo efficacy" Bioorganic & Medicinal Chemistry Letters (2006).

Grimsby, "Discovery and Actions of Glucokinase Activators" Metabolic Diseases World Summit, Jul. 24-25, 2006.

Sarabu and Grimsby, "Targeting glucokinase activation for the treatment of type 2 diabetes—A status review" Current Opinion in Drug Discovery & Development 8(5):631-637 (2005).

Efanov et al., "A novel glucokinase activator modulates pancreatic islet and hepacyte function" Endocrinology (May 26, 2005).

Matschinsky et al., "The Network of Glucokinase-Expressing Cells in Glucose Homeostasis and the Potential of Glucokinase Activators for Diabetes Therapy" Diabetes 55:1-12 (Jan. 2006).

Grimsby et al., "Allosteric Activators of Glucokinase: Potential Role in Diabetes Therapy" Science 301:370-373 (Jul. 18, 2003).

Castelhano et al., "Glucokinase-activating ureas" Bioorganic & Medicinal Chemistry Letters 15:1501-1504 (2005).

Office Action mailed in U.S. Patent Application Publication No. 2005-0282851 (U.S. Appl. No. 10/529,670) on Sep. 22, 2008.

Office Action mailed in U.S. Patent Application Publication No. 2005-0282851 (U.S. Appl. No. 10/529,670) on Apr. 28, 2009.

Office Action mailed in U.S. Patent Application Publication No. 2007-0265297 (U.S. Appl. No. 11/547,227) on Apr. 7, 2009.

Office Action mailed in U.S. Patent Application Publication No. 2008-0318948 (U.S. Appl. No. 12/088,608) on Sep. 14, 2009.

* cited by examiner

SULFONAMIDE-THIAZOLPYRIDINE DERIVATIVES AS GLUCOKINASE ACTIVATORS USEFUL THE TREATMENT OF TYPE 2 DIABETES

This application is the National Stage of Application No. PCT/EP2005/003456, filed on Apr. 1, 2005, which claims benefit under 35 U.S.C. § 119(e) of U.S. Provisional Application No. 60/559,184, filed Apr. 2, 2004. The contents of both are incorporated herein by reference in their entirety.

ORGANIC COMPOUNDS

The present invention relates to thiazolopyridine derivatives, pharmaceutical compositions containing them, and to methods of treating glucokinase mediated conditions, in particular, impaired glucose tolerance and Type 2 diabetes, by employing such compounds.

Accordingly, the present invention provides compounds of the formula

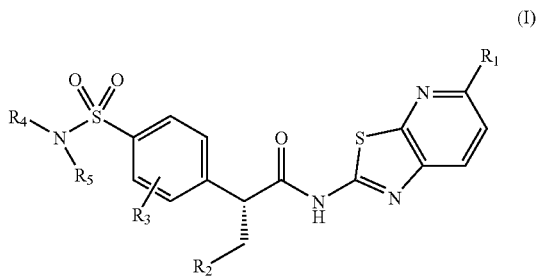

(I)

wherein
$R_1$ is hydrogen, halogen, cyano, nitro, optionally substituted alkyl, alkoxy, alkylthio, alkylthiono, sulfonyl, carboxy, carbamoyl, sulfamoyl or optionally substituted amino;
$R_2$ is $C_3$-$C_6$ cycloalkyl or $C_3$-$C_6$ heterocyclyl;
$R_3$ is hydrogen, halogen, cyano, lower alkyl or lower alkoxy;
$R_4$ is hydrogen, optionally substituted alkyl, or cycloalkyl;
$R_5$ is —$(CR_6R_7)_m$—W—$R_8$ in which
  $R_6$ and $R_7$ are independently hydrogen, optionally substituted alkyl or cycloalkyl; or
  $R_6$ and $R_7$ combined are alkylene which together with the carbon atom to which they are attached form a 3- to 7-membered ring;
  m is zero or an integer from 1 to 5;
  W is —$NR_9$— in which
    $R_9$ is hydrogen, optionally substituted alkyl or heterocyclyl; or
    $R_9$ is —$C(O)R_{10}$, —$C(O)OR_{10}$, or —$C(O)NR_{10}R_{11}$ in which
      $R_{10}$ is optionally substituted alkyl, cycloalkyl, aryl, heteroaryl, aralkyl or heteroaralkyl;
      $R_{11}$ is hydrogen or lower alkyl; or
      $R_{11}$ and $R_{10}$ combined are alkylene which together with the nitrogen atom to which they are attached form a 4- to 7-membered ring; or
  W is absent;
  $R_8$ is hydrogen, optionally substituted $C_1$-$C_7$ alkyl, cycloalkyl, aryl or heterocyclyl; or $R_8$ and $R_9$ combined are alkylene which together with the nitrogen atom to which they are attached form a 4- to 7-membered ring; or
  $R_5$ and $R_4$ combined are alkylene which together with the nitrogen atom to which they are attached form a 4- to 7-membered ring; or
  $R_5$ and $R_4$ taken together with the nitrogen atom to which they are attached form a 6- to 12-membered fused, bridged or spiral bicyclic ring, which may be optionally substituted or may contain 1 to 3 other heteroatoms selected from oxygen, nitrogen and sulfur;

or an enantiomer thereof; or an enantiomeric mixture thereof; or a pharmaceutically acceptable salt thereof.

The compounds of the present invention provide pharmacological agents which are glucokinase activators and, thus, may be employed for the treatment of glucokinase mediated conditions. Accordingly, the compounds of formula (I) may be employed for prevention and treatment of impaired glucose tolerance, Type 2 diabetes and obesity.

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group.

The term "optionally substituted alkyl" refers to unsubstituted or substituted straight- or branched-chain hydrocarbon groups having 1-20 carbon atoms, preferably 1-10 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, alkanoyl, alkoxy, alkanoyloxy, thiol, alkylthio, alkylthiono, sulfonyl, sulfamoyl, carbamoyl, cyano, carboxy, acyl, aryl, alkenyl, alkynyl, aralkoxy, guanidino, optionally substituted amino, heterocyclyl including imidazolyl, furyl, thienyl, thiazolyl, pyrrolidyl, pyridyl, pyrimidyl and the like.

The term "lower alkyl" refers to those alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 4-6 carbon atoms connected by single bonds, e.g., —$(CH_2)_x$—, wherein x is 4-6, which may be interrupted with one or more heteroatoms selected from O, S, S(O), S(O)$_2$ or NR, wherein R may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carbamoyl" refers to H$_2$NC(O)—, alkyl-NH C(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.
The term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.
The term "monocyclic aryl" refers to optionally substituted phenyl as described under aryl.
The term "aralkyl" refers to an aryl group bonded directly through an alkyl group, such as benzyl.
The term "aralkanoyl" refers to aralkyl-C(O)—.
The term "aralkylthio" refers to aralkyl-S—.

The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of the following:

(a) optionally substituted alkyl;
(b) hydroxyl (or protected hydroxyl);
(c) halo;
(d) oxo, i.e., =O;
(e) optionally substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl;
(o) alkanoyloxy;

(p) aroyloxy;
(q) arylthio;
(r) aryloxy;
(s) alkylthio;
(t) formyl;
(u) carbamoyl;
(v) aralkyl; and
(w) aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The term "heterocycloalkyl" refers to nonaromatic heterocyclic groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

Pharmaceutically acceptable salts of the compounds of the present invention refer to salts formed with acids, namely acid addition salts, such as of mineral acids, organic carboxylic acids and organic sulfonic acids, e.g., hydrochloric acid, maleic acid and methanesulfonic acid, respectively.

Similarly, pharmaceutically acceptable salts of the compounds of the invention refer to salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)-methyl-ammonium salts and salts with amino acids provided an acidic group constitutes part of the structure.

As described herein above, the present invention provides thiazolopyridine derivatives of formula (I), pharmaceutical compositions containing them, methods for preparing said compounds, and methods of treating glucokinase mediated conditions by administration of a therapeutically effective amount of a compound of the present invention, or a pharmaceutical composition thereof.

Preferred are the compounds of formula (I) wherein
$R_1$ is hydrogen, halogen, cyano, nitro, alkoxy, carboxy, carbamoyl or optionally substituted amino;
$R_2$ is $C_3$-$C_6$ cycloalkyl or $C_3$-$C_6$ heterocyclyl;
$R_3$ is hydrogen, halogen, cyano, lower alkyl or lower alkoxy;
$R_4$ is hydrogen or lower alkyl;
$R_5$ is —(CR$_6$R$_7$)$_m$—W—R$_8$ in which
$R_6$ and $R_7$ are independently hydrogen or optionally substituted lower alkyl;
m is zero or an integer from 1 to 5;
W is —NR$_9$— in which
$R_9$ is hydrogen or lower alkyl; or
$R_9$ is —C(O)R$_{10}$, —C(O)OR$_{10}$, or —C(O)NR$_{10}$R$_{11}$ in which
$R_{10}$ is optionally substituted alkyl, cycloalkyl, aryl, heteroaryl, aralkyl or heteroaralkyl;
$R_{11}$ is hydrogen or lower alkyl; or
$R_{11}$ and $R_{10}$ combined are alkylene which together with the nitrogen atom to which they are attached form a 5- to 7-membered ring; or
W is absent;
$R_8$ is hydrogen, optionally substituted $C_1$-$C_7$ alkyl, cycloalkyl, aryl or heterocyclyl; or
$R_8$ and $R_9$ combined are alkylene which together with the nitrogen atom to which they are attached form a 5- to 7-membered ring; or
$R_5$ and $R_4$ combined are alkylene which together with the nitrogen atom to which they are attached form a 5- to 7-membered ring;

or an enantiomer thereof; or an enantiomeric mixture thereof; or a pharmaceutically acceptable salt thereof.

Further preferred are the compounds of formula (I) wherein
$R_4$ is hydrogen or lower alkyl;
$R_5$ is —(CR$_6$R$_7$)$_m$—W—R$_8$ in which
$R_6$ and $R_7$ are independently hydrogen or optionally substituted lower alkyl;
m is an integer from 2 to 5;
W is —NR$_9$— in which
$R_9$ is hydrogen or lower alkyl; or
$R_9$ is —C(O)R$_{10}$, —C(O)OR$_{10}$, or —C(O)NR$_{10}$R$_{11}$ in which
$R_{10}$ is optionally substituted alkyl, cycloalkyl, aryl, heteroaryl, aralkyl or heteroaralkyl;
$R_{11}$ is hydrogen or lower alkyl; or
$R_{11}$ and $R_{10}$ combined are alkylene which together with the nitrogen atom to which they are attached form a 5- to 7-membered ring; or
$R_8$ is hydrogen, optionally substituted $C_1$-$C_7$ alkyl, cycloalkyl, aryl or heterocyclyl; or
$R_8$ and $R_9$ combined are alkylene which together with the nitrogen atom to which they are attached form a 5- to 7-membered ring;

or an enantiomer thereof; or an enantiomeric mixture thereof; or a pharmaceutically acceptable salt thereof.

More preferred are the compounds of formula (I) wherein
$R_1$ is hydrogen, halogen, $C_1$-$C_4$ alkoxy, carboxy or carbamoyl;
$R_2$ is $C_3$-$C_5$ cycloalkyl;
$R_3$ is hydrogen;
$R_6$ and $R_7$ are hydrogen;

or an enantiomer thereof; or an enantiomeric mixture thereof; or a pharmaceutically acceptable salt thereof.

Most preferred are the compounds of formula (I) having the formula

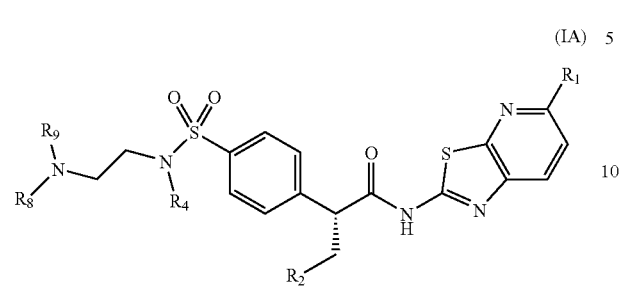

(IA)

wherein
- $R_1$ is hydrogen, halogen, $C_1$-$C_4$ alkoxy, carboxy or carbamoyl;
- $R_2$ is $C_3$-$C_5$ cycloalkyl;
- $R_4$ is hydrogen or lower alkyl;
- $R_8$ is hydrogen, optionally substituted $C_1$-$C_7$ alkyl, cycloalkyl, aryl or heterocyclyl;
- $R_9$ is hydrogen or lower alkyl; or
- $R_9$ is —C(O)$R_{10}$, —C(O)O$R_{10}$, or —C(O)N$R_{10}R_{11}$ in which
  - $R_{10}$ is optionally substituted alkyl, cycloalkyl, aryl, heteroaryl, aralkyl or heteroaralkyl;
  - $R_{11}$ is hydrogen or lower alkyl; or
  - $R_{11}$ and $R_{10}$ combined are alkylene which together with the nitrogen atom to which they are attached form a 5- to 7-membered ring; or
- $R_9$ and $R_8$ combined are alkylene which together with the nitrogen atom to which they are attached form a 5- to 7-membered ring;

or an enantiomer thereof; or an enantiomeric mixture thereof; or a pharmaceutically acceptable salt thereof.

Preferred are the compounds of formula (IA) wherein
- $R_1$ is methoxy;

or an enantiomer thereof; or an enantiomeric mixture thereof; or a pharmaceutically acceptable salt thereof.

Preferred are also the compounds of formula (IA) wherein
- $R_2$ is cyclopentyl;

or an enantiomer thereof; or an enantiomeric mixture thereof; or a pharmaceutically acceptable salt thereof.

Preferred are also the compounds of formula (IA) wherein
- $R_1$ is methoxy;
- $R_2$ is cyclopentyl;

or an enantiomer thereof; or an enantiomeric mixture thereof; or a pharmaceutically acceptable salt thereof.

Preferred are also the compounds of formula (I), designated as the A group, wherein
- $R_4$ and $R_5$ combined are alkylene which together with the nitrogen atom to which they are attached form a 5- to 7-membered ring;

or an enantiomer thereof; or an enantiomeric mixture thereof; or a pharmaceutically acceptable salt thereof.

Preferred are the compounds in the A group of the formula

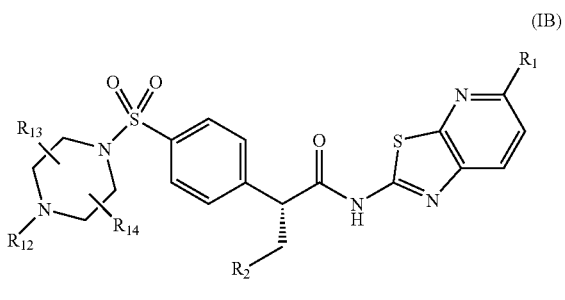

(IB)

wherein
- $R_1$ is hydrogen, halogen, $C_1$-$C_4$ alkoxy, carboxy or carbamoyl;
- $R_2$ is $C_3$-$C_5$ cycloalkyl;
- $R_{12}$ is hydrogen, optionally substituted lower alkyl, cycloalkyl, aryl, heteroaryl, aralkyl or heteroaralkyl; or
- $R_{12}$ is —C(O)$R_{15}$, —C(O)O$R_{15}$, or —C(O)N$R_{15}R_{16}$ in which
  - $R_{15}$ optionally substituted alkyl, cycloalkyl, aryl, heteroaryl, aralkyl or heteroaralkyl;
  - $R_{16}$ is hydrogen or lower alkyl; or
  - $R_{16}$ and $R_{15}$ combined are alkylene which together with the nitrogen atom to which they are attached form a 5- to 7-membered ring;
- $R_{13}$ and $R_{14}$ are independently hydrogen or lower alkyl;

or an enantiomer thereof; or an enantiomeric mixture thereof; or a pharmaceutically acceptable salt thereof.

Preferred are the compounds of formula (IB) wherein
- $R_1$ is methoxy;

or an enantiomer thereof; or an enantiomeric mixture thereof; or a pharmaceutically acceptable salt thereof.

Preferred are also the compounds of formula (IB) wherein
- $R_2$ is cyclopentyl;

or an enantiomer thereof; or an enantiomeric mixture thereof; or a pharmaceutically acceptable salt thereof.

Preferred are also the compounds of formula (IB) wherein
- $R_1$ is methoxy;
- $R_2$ is cyclopentyl;

or an enantiomer thereof; or an enantiomeric mixture thereof; or a pharmaceutically acceptable salt thereof.

Preferred are also the compounds of formula (IB) wherein
- $R_{12}$ is methyl;

or an enantiomer thereof; or an enantiomeric mixture thereof; or a pharmaceutically acceptable salt thereof.

Preferred are also the compounds of formula (IB) wherein
- $R_1$ is methoxy;
- $R_2$ is cyclopentyl;
- $R_{13}$ and $R_{14}$ are independently hydrogen or methyl;

or an enantiomer thereof; or an enantiomeric mixture thereof; or a pharmaceutically acceptable salt thereof.

Preferred are also the compounds in the A group of the formula

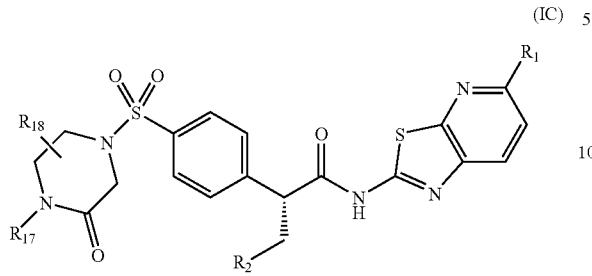

(IC)

wherein
R$_1$ is hydrogen, halogen, C$_1$-C$_4$ alkoxy, carboxy or carbamoyl;
R$_2$ is C$_3$-C$_5$ cycloalkyl;
R$_{17}$ is hydrogen, optionally substituted lower alkyl, cycloalkyl, aryl, heteroaryl, aralkyl or heteroaralkyl;
R$_{18}$ is hydrogen or lower alkyl;

or an enantiomer thereof; or an enantiomeric mixture thereof; or a pharmaceutically acceptable salt thereof.
Preferred are the compounds of formula (IC) wherein
R$_1$ is methoxy;

or an enantiomer thereof; or an enantiomeric mixture thereof; or a pharmaceutically acceptable salt thereof.
Preferred are also the compounds of formula (IC) wherein
R$_2$ is cyclopentyl;

or an enantiomer thereof; or an enantiomeric mixture thereof; or a pharmaceutically acceptable salt thereof.
Preferred are also the compounds of formula (IC) wherein
R$_1$ is methoxy;
R$_2$ is cyclopentyl;

or an enantiomer thereof; or an enantiomeric mixture thereof; or a pharmaceutically acceptable salt thereof.
Preferred are also the compounds of formula (IC) wherein
R$_1$ is methoxy;
R$_2$ is cyclopentyl;
R$_{18}$ is hydrogen or methyl;

or an enantiomer thereof; or an enantiomeric mixture thereof; or a pharmaceutically acceptable salt thereof.
Preferred are also the compounds in the A group of the formula

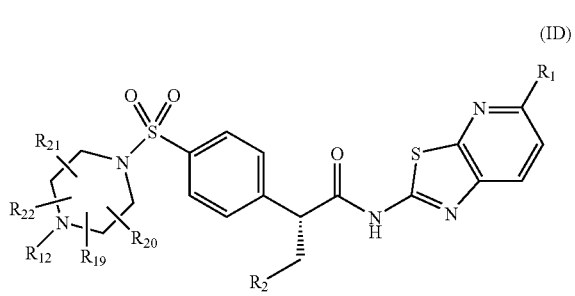

(ID)

wherein
R$_1$ is hydrogen, halogen, C$_1$-C$_4$ alkoxy, carboxy or carbamoyl;
R$_2$ is C$_3$-C$_5$ cycloalkyl;
R$_{12}$ is hydrogen, optionally substituted lower alkyl, cycloalkyl, aryl, heteroaryl, aralkyl or heteroaralkyl; or
R$_{12}$ is —C(O)R$_{15}$, —C(O)OR$_{15}$, or —C(O)NR$_{15}$R$_{16}$ in which
R$_{15}$ optionally substituted alkyl, cycloalkyl, aryl, heteroaryl, aralkyl or heteroaralkyl;
R$_{16}$ is hydrogen or lower alkyl; or
R$_{16}$ and R$_{15}$ combined are alkylene which together with the nitrogen atom to which they are attached form a 5- to 7-membered ring;
R$_{19}$, R$_{20}$, R$_{21}$, and R$_{22}$ are independently hydrogen, optionally substituted lower alkyl, cycloalkyl, aryl or heterocyclyl;

or an enantiomer thereof; or an enantiomeric mixture thereof; or a pharmaceutically acceptable salt thereof.
Preferred are the compounds of formula (ID) wherein
R$_1$ is methoxy;

or an enantiomer thereof; or an enantiomeric mixture thereof; or a pharmaceutically acceptable salt thereof.
Preferred are also the compounds of formula (ID) wherein
R$_2$ is cyclopentyl;

or an enantiomer thereof; or an enantiomeric mixture thereof; or a pharmaceutically acceptable salt thereof.
Preferred are also the compounds of formula (ID) wherein
R$_1$ is methoxy;
R$_2$ is cyclopentyl;

or an enantiomer thereof; or an enantiomeric mixture thereof; or a pharmaceutically acceptable salt thereof.
Preferred are also the compounds of formula (ID) wherein
R$_{12}$ is methyl;

or an enantiomer thereof; or an enantiomeric mixture thereof; or a pharmaceutically acceptable salt thereof.
Preferred are also the compounds of formula (ID) wherein
R$_1$ is methoxy;
R$_2$ is cyclopentyl;
R$_{19}$, R$_{20}$, R$_{21}$ and R$_{22}$ are methyl;

or an enantiomer thereof; or an enantiomeric mixture thereof; or a pharmaceutically acceptable salt thereof.
Preferred are also the compounds of formula (I), designated as the B group, wherein
R$_4$ and R$_5$ taken together with the nitrogen atom to which they are attached form a 8- to 12-membered fused, bridged or spiral bicyclic ring, which may be optionally substituted or may contain 1 to 3 other heteroatoms selected from oxygen, nitrogen and sulfur;

or an enantiomer thereof; or an enantiomeric mixture thereof; or a pharmaceutically acceptable salt thereof.
Preferred are the compounds in the B group of the formula

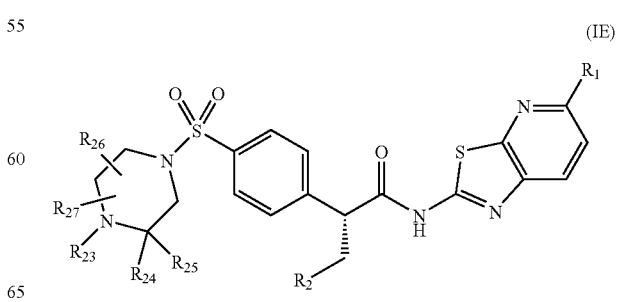

(IE)

wherein
R$_1$ is hydrogen, halogen, C$_1$-C$_4$ alkoxy, carboxy or carbamoyl;
R$_2$ is C$_3$-C$_5$ cycloalkyl;
R$_{12}$ is hydrogen, optionally substituted lower alkyl, cycloalkyl, aryl, heteroaryl, aralkyl or heteroaralkyl; or
R$_{23}$ is —C(O)R$_{15}$, —C(O)OR$_{15}$, or —C(O)NR$_{15}$R$_{16}$ in which
R$_{15}$ optionally substituted alkyl, cycloalkyl, aryl, heteroaryl, aralkyl or heteroaralkyl;
R$_{16}$ is hydrogen or lower alkyl; or
R$_{16}$ and R$_{15}$ combined are alkylene which together with the nitrogen atom to which they are attached form a 5- to 7-membered ring; or
R$_{23}$ and R$_{24}$ combined are alkylene which together with the nitrogen and carbon atoms to which they are attached form a 4- to 7-membered ring;
R$_{25}$ is hydrogen; or
R$_{25}$ and R$_{24}$ combined are alkylene which together with the carbon atom to which they are attached form a 3- to 7-membered ring;
R$_{26}$ and R$_{27}$ are independently optionally substituted lower alkyl, cycloalkyl, aryl or heterocyclyl;

or an enantiomer thereof; or an enantiomeric mixture thereof; or a pharmaceutically acceptable salt thereof.
Preferred are the compounds of formula (IE) wherein
R$_1$ is methoxy;

or an enantiomer thereof; or an enantiomeric mixture thereof; or a pharmaceutically acceptable salt thereof.
Preferred are the compounds of formula (IE) wherein
R$_2$ is cyclopentyl;

or an enantiomer thereof; or an enantiomeric mixture thereof; or a pharmaceutically acceptable salt thereof.
Preferred are the compounds of formula (IE) wherein
R$_1$ is methoxy;
R$_2$ is cyclopentyl;

or an enantiomer thereof; or an enantiomeric mixture thereof; or a pharmaceutically acceptable salt thereof.
The compounds of the invention depending on the nature of the substituents possess one or more asymmetric centers. The resulting diastereoisomers, optical isomers, i.e., enantiomers, and geometric isomers, and mixtures thereof, are encompassed by the instant invention. Preferred are the compounds of the present invention wherein the substituent at the carbon atom adjacent to the amide group attains the R-configuration.

Particular embodiments of the invention are:
3-Cyclopentyl-2-(4-cyclopropylsulfamoyl-phenyl)-N-(5-methoxy-thiazolo[5,4-b]pyridin-2-yl)-propionamide;
3-Cyclopentyl-2-[4-(2-methoxy-ethylsulfamoyl)-phenyl]-N-(5-methoxy-thiazolo[5,4-b]pyridin-2-yl)-propionamide;
3-Cyclopentyl-2-[4-(3-methoxy-benzylsulfamoyl)-phenyl]-N-(5-methoxy-thiazolo[5,4-b]pyridin-2-yl)-propionamide;
3-Cyclopentyl-N-(5-methoxy-thiazolo[5,4-b]pyridin-2-yl)-2-(4-phenylsulfamoyl-phenyl)-propionamide;
2-[4-(2-Carbamoyl-ethylsulfamoyl)-phenyl]-3-cyclopentyl-N-(5-methoxy-thiazolo[5,4-b]pyridin-2-yl)-propionamide;
3-Cyclopentyl-2-(4-diisopropylsulfamoyl-phenyl)-N-(5-methoxy-thiazolo[5,4-b]pyridin-2-yl)-propionamide;
3-Cyclopentyl-2-{4-[(furan-2-ylmethyl)-sulfamoyl]-phenyl}-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(phenyl-propyl-sulfamoyl)-phenyl]-propionamide;
3-Cyclopentyl-2-(4-dimethylsulfamoyl-phenyl)-N-(5-methoxy-thiazolo[5,4-b]pyridin-2-yl)-propionamide;
3-Cyclopentyl-2-(4-diethylsulfamoyl-phenyl)-N-(5-methoxy-thiazolo[5,4-b]pyridin-2-yl)-propionamide;
3-Cyclopentyl-2-(4-dipropylsulfamoyl-phenyl)-N-(5-methoxy-thiazolo[5,4-b]pyridin-2-yl)-propionamide;
3-Cyclopentyl-N-(5-methoxy-thiazolo[5,4-b]pyridin-2-yl)-2-{4-[(pyridin-3-ylmethyl)-sulfamoyl]-phenyl}-propionamide;
2-(4-Cyclohexylsulfamoyl-phenyl)-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(piperidine-1-sulfonyl)-phenyl]-propionamide;
3-Cyclopentyl-N-(5-methoxy-thiazolo[5,4-b]pyridin-2-yl)-2-[4-(morpholine-4-sulfonyl)-phenyl]-propionamide;
3-Cyclopentyl-N-(5-methoxy-thiazolo[5,4-b]pyridin-2-yl)-2-{4-[(thiophen-2-ylmethyl)-sulfamoyl]-phenyl}-propionamide;
3-Cyclopentyl-N-(5-methoxy-thiazolo[5,4-b]pyridin-2-yl)-2-[4-(pyridin-3-ylsulfamoyl)-phenyl]-propionamide;
3-Cyclopentyl-2-[4-(2-fluoro-benzylsulfamoyl)-phenyl]-N-(5-methoxy-thiazolo[5,4-b]pyridin-2-yl)-propionamide;
3-Cyclopentyl-2-[4-(4-methoxy-benzylsulfamoyl)-phenyl]-N-(5-methoxy-thiazolo[5,4-b]pyridin-2-yl)-propionamide;
2-(4-Benzylsulfamoyl-phenyl)-3-cyclopentyl-N-(5-methoxy-thiazolo[5,4-b]pyridin-2-yl)-propionamide;
2-[4-(Benzyl-methyl-sulfamoyl)-phenyl]-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(4-methyl-piperazine-1-sulfonyl)-phenyl]-propionamide;
3-Cyclopentyl-2-(4-dibutylsulfamoyl-phenyl)-N-(5-methoxy-thiazolo[5,4-b]pyridin-2-yl)-propionamide;
3-Cyclopentyl-2-[4-(4-ethyl-piperazine-1-sulfonyl)-phenyl]-N-(5-methoxy-thiazolo[5,4-b]pyridin-2-yl)-propionamide;
2-[4-(4-Acetyl-piperazine-1-sulfonyl)-phenyl]-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(piperazine-1-sulfonyl)-phenyl]-propionamide hydrochloride;
3-Cyclopentyl-N-(5-methoxy-thiazolo[5,4-b]pyridin-2-yl)-2-[4-(4-phenyl-piperazine-1-sulfonyl)-phenyl]-propionamide;
3-Cyclopentyl-2-{4-[4-(2-methoxy-phenyl)-piperazine-1-sulfonyl]-phenyl}-N-(5-methoxy-thiazolo[5,4-b]pyridin-2-yl)-propionamide;
2-{4-[4-(3-Chloro-phenyl)-piperazine-1-sulfonyl]-phenyl}-3-cyclopentyl-N-(5-methoxy-thiazolo[5,4-b]pyridin-2-yl)-propionamide;
2-[4-(4-Benzyl-piperazine-1-sulfonyl)-phenyl]-3-cyclopentyl-N-(5-methoxy-thiazolo[5,4-b]pyridin-2-yl)-propionamide;
3-Cyclopentyl-2-[4-(4-isopropyl-piperazine-1-sulfonyl)-phenyl]-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(4-o-tolyl-piperazine-1-sulfonyl)-phenyl]-propionamide;
N-[2-(2-{4-[4-(2-Chloro-phenyl)-piperazine-1-sulfonyl]-phenyl}-3-cyclopentyl-propionylamino)-thiazol-5-yl]-acetimidic acid methyl ester;

3-Cyclopentyl-2-{4-[4-(4-fluoro-phenyl)-piperazine-1-sulfonyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-pyridin-2-yl-piperazine-1-sulfonyl)-phenyl]-propionamide;

3-Cyclopentyl-2-{4-[(2-hydroxy-ethyl)-methyl-sulfamoyl]-phenyl}-N-(6-methoxy-thiazolo[5,4-b]pyridin-2-yl)-propionamide;

3-Cyclopentyl-N-(5-methoxy-thiazolo[5,4-b]pyridin-2-yl)-2-[4-(4-pyridin-4-yl-piperazine-1-sulfonyl)-phenyl]-propionamide;

3-Cyclopentyl-N-(5-methoxy-thiazolo[5,4-b]pyridin-2-yl)-2-[4-(2-piperidin-1-yl-ethylsulfamoyl)-phenyl]-propionamide;

3-Cyclopentyl-N-(5-methoxy-thiazolo[5,4-b]pyridin-2-yl)-2-[4-(2-pyrrolidin-1-yl-ethylsulfamoyl)-phenyl]-propionamide;

3-Cyclopentyl-2-{4-[(2-dimethylamino-ethyl)-ethyl-sulfamoyl]-phenyl}-N-(5-methoxy-thiazolo[5,4-b]pyridin-2-yl)-propionamide hydrochloride;

3-Cyclopentyl-2-[4-(2-dimethylamino-ethylsulfamoyl)-phenyl]-N-(5-methoxy-thiazolo[5,4-b]pyridin-2-yl)-propionamide hydrochloride;

3-Cyclopentyl-2-{4-[4-(2-hydroxy-ethyl)-piperazine-1-sulfonyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[methyl-(2-pyrrolidin-1-yl-ethyl)-sulfamoyl]-phenyl}-propionamide hydrochloride;

3-Cyclopentyl-N-(5-methoxy-thiazolo[5,4-b]pyridin-2-yl)-2-{4-[methyl-(2-piperidin-1-yl-ethyl)-sulfamoyl]-phenyl}-propionamide hydrochloride;

3-Cyclopentyl-N-(5-methoxy-thiazolo[5,4-b]pyridin-2-yl)-2-{4-[methyl-(2-morpholin-4-yl-ethyl)-sulfamoyl]-phenyl}-propionamide;

4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid ethyl ester;

3-Cyclopentyl-2-{4-[(2-diethylamino-ethyl)-methyl-sulfamoyl]-phenyl}-N-(5-methoxy-thiazolo[5,4-b]pyridin-2-yl)-propionamide;

3-Cyclopentyl-2-[4-(2-hydroxy-ethylsulfamoyl)-phenyl]-N-(5-methoxy-thiazolo[5,4-b]pyridin-2-yl)-propionamide;

2-[4-(4-Carbamoylmethyl-piperazine-1-sulfonyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(pyrrolidine-1-sulfonyl)-phenyl]-propionamide;

3-Cyclopentyl-N-(5-methoxy-thiazolo[5,4-b]pyridin-2-yl)-2-[4-(pyridin-2-ylsulfamoyl)-phenyl]-propionamide;

4-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester;

4-({4-[2-Cyclopentyl-1-(5-methoxy-thiazolo[5,4-b]pyridin-2-ylcarbamoyl)-ethyl]-benzenesulfonylamino}-methyl)-piperidine-1-carboxylic acid tert-butyl ester;

3-Cyclopentyl-2-{4-[(1-ethyl-pyrrolidin-2-ylmethyl)-sulfamoyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(piperidin-4-ylsulfamoyl)-phenyl]-propionamide;

3-Cyclopentyl-N-(5-methoxy-thiazolo[5,4-b]pyridin-2-yl)-2-{4-[(piperidin-4-ylmethyl)-sulfamoyl]-phenyl}-propionamide;

(4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid ethyl ester;

3-Cyclopentyl-2-{4-[(3-hydroxy-5-hydroxymethyl-2-methyl-pyridin-4-ylmethyl)-sulfamoyl]-phenyl}-N-(5-methoxy-thiazolo[5,4-b]pyridin-2-yl)-propionamide;

3-{4-[2-Cyclopentyl-1-(5-methoxy-thiazolo[5,4-b]pyridin-2-ylcarbamoyl)-ethyl]-benzenesulfonylamino}-azetidine-1-carboxylic acid tert-butyl ester;

(1-{4-[2-Cyclopentyl-1-(5-methoxy-thiazolo[5,4-b]pyridin-2-ylcarbamoyl)-ethyl]-benzenesulfonyl}-azetidin-3-yl)-carbamic acid tert-butyl ester;

3-({4-[2-Cyclopentyl-1-(5-methoxy-thiazolo[5,4-b]pyridin-2-ylcarbamoyl)-ethyl]-benzenesulfonylamino}-methyl)-azetidine-1-carboxylic acid tert-butyl ester;

1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid;

2-[4-(Azetidin-3-ylsulfamoyl)-phenyl]-3-cyclopentyl-N-(5-methoxy-thiazolo[5,4-b]pyridin-2-yl)-propionamide;

2-[4-(3-Amino-azetidine-1-sulfonyl)-phenyl]-3-cyclopentyl-N-(5-methoxy-thiazolo[5,4-b]pyridin-2-yl)-propionamide;

2-{4-[(Azetidin-3-ylmethyl)-sulfamoyl]-phenyl}-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-(4-sulfamoyl-phenyl)-propionamide;

3-Cyclopentyl-N-(5-methoxy-thiazolo[5,4-b]pyridin-2-yl)-2-{4-[(pyridin-4-ylmethyl)-sulfamoyl]-phenyl}-propionamide;

3-Cyclopentyl-N-(5-methoxy-thiazolo[5,4-b]pyridin-2-yl)-2-{4-[(pyridin-2-ylmethyl)-sulfamoyl]-phenyl}-propionamide;

4-{4-[2-Cyclopentyl-1-(5-methoxy-thiazolo[5,4-b]pyridin-2-ylcarbamoyl)-ethyl]-benzenesulfonylamino}-benzoic acid;

3-Cyclopentyl-2-[4-(4-dimethylamino-phenylsulfamoyl)-phenyl]-N-(5-methoxy-thiazolo[5,4-b]pyridin-2-yl)-propionamide;

2-[4-(4-Cyclohexylmethyl-piperazine-1-sulfonyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(1,2,2,6,6-pentamethyl-piperidin-4-ylsulfamoyl)-phenyl]-propionamide;

3-Cyclopentyl-2-[4-(1,1-dimethyl-2-morpholin-4-yl-ethylsulfamoyl)-phenyl]-N-(5-methoxy-thiazolo[5,4-b]pyridin-2-yl)-propionamide;

(S)-3-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester;

2-[4-([1,4']Bipiperidinyl-1'-sulfonyl)-phenyl]-3-cyclopentyl-N-(5-methoxy-thiazolo[5,4-b]pyridin-2-yl)-propionamide;

3-Cyclopentyl-2-[4-(4-diethylamino-piperidine-1-sulfonyl)-phenyl]-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-pyrrolidin-1-yl-piperidine-1-sulfonyl)-phenyl]-propionamide;

3-Cyclopentyl-N-(5-methoxy-thiazolo[5,4-b]pyridin-2-yl)-2-[4-(octahydro-pyrido[1,2-a]pyrazine-2-sulfonyl)-phenyl]-propionamide;

3-Cyclopentyl-N-(5-methoxy-thiazolo[5,4-b]pyridin-2-yl)-2-[4-(pyridin-4-ylsulfamoyl)-phenyl]-propionamide;

3-Cyclopentyl-N-(5-methoxy-thiazolo[5,4-b]pyridin-2-yl)-2-[4-((S)-piperidin-3-ylsulfamoyl)-phenyl]-propionamide;

3-Cyclopentyl-2-[4-(1-ethyl-piperidin-3-ylsulfamoyl)-phenyl]-N-(5-methoxy-thiazolo[5,4-b]pyridin-2-yl)-propionamide;

2-{4-[4-(2-Cyano-ethyl)-piperazine-1-sulfonyl]-phenyl}-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-piperidin-1-ylmethyl-phenylsulfamoyl)-phenyl]-propionamide;

3-Cyclopentyl-N-(5-methoxy-thiazolo[5,4-b]pyridin-2-yl)-2-[4-(1-phenyl-2-pyrrolidin-1-yl-ethylsulfamoyl)-phenyl]-propionamide;

2-[4-(4-Cyclohexyl-piperazine-1-sulfonyl)-phenyl]-3-cyclopentyl-N-(5-methoxy-thiazolo[5,4-b]pyridin-2-yl)-propionamide;

3-Cyclopentyl-2-[4-(2-dimethylamino-2-pyridin-3-yl-ethylsulfamoyl)-phenyl]-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[methyl-(1-methyl-piperidin-4-yl)-sulfamoyl]-phenyl}-propionamide;

2-[4-(4-Cyclooctyl-piperazine-1-sulfonyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-phenethyl-piperazine-1-sulfonyl)-phenyl]-propionamide;

(R)-3-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester;

3-Cyclopentyl-2-{4-[4-(2-ethoxy-ethyl)-piperazine-1-sulfonyl]-phenyl}-N-(5-methoxy-thiazolo[5,4-b]pyridin-2-yl)-propionamide;

3-Cyclopentyl-2-{4-[4-(2-diethylamino-ethyl)-piperazine-1-sulfonyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-[4-((R)-piperidin-3-ylsulfamoyl)-phenyl]-propionamide;

(1-{4-[2-Cyclopentyl-1-(5-methoxy-thiazolo[5,4-b]pyridin-2-ylcarbamoyl)-ethyl]-benzenesulfonyl}-azetidin-3-ylamino)-acetic acid ethyl ester;

[3-({4-[2-Cyclopentyl-1-(5-methoxy-thiazolo[5,4-b]pyridin-2-ylcarbamoyl)-ethyl]-benzenesulfonylamino}-methyl)-azetidin-1-yl]-acetic acid ethyl ester;

3-Cyclopentyl-2-[4-(hexahydro-pyrrolo[1,2-a]pyrazine-2-sulfonyl)-phenyl]-N-(5-methoxy-thiazolo[5,4-b]pyridin-2-yl)-propionamide;

4-{4-[2-Cyclopentyl-1-(5-methoxy-thiazolo[5,4-b]pyridin-2-ylcarbamoyl)-ethyl]-benzenesulfonylamino}-piperidine-1-carboxylic acid ethyl ester;

3-Cyclopentyl-2-{4-[cyclopropyl-(1-methyl-piperidin-4-yl)-sulfamoyl]-phenyl}-N-(5-methoxy-thiazolo[5,4-b]pyridin-2-yl)-propionamide;

2-[4-(4-Benzyl-4,7-diaza-spiro[2.5]octane-7-sulfonyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[4-(4-methyl-piperazin-1-yl)-piperidine-1-sulfonyl]-phenyl}-propionamide;

3-Cyclopentyl-2-[4-(4-cyclopentyl-piperazine-1-sulfonyl)-phenyl]-N-(5-methoxy-thiazolo[5,4-b]pyridin-2-yl)-propionamide;

3-Cyclopentyl-2-[4-(4,7-diaza-spiro[2.5]octane-7-sulfonyl)-phenyl]-N-(5-methoxy-thiazolo[5,4-b]pyridin-2-yl)-propionamide;

3-({4-[2-Cyclopentyl-1-(5-methoxy-thiazolo[5,4-b]pyridin-2-ylcarbamoyl)-ethyl]-benzenesulfonylamino}-methyl)-piperidine-1-carboxylic acid tert-butyl ester;

(S)-1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid;

(R)-1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid;

3-Cyclopentyl-2-{4-[4-(2-diethylamino-acetyl)-piperazine-1-sulfonyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[(piperidin-3-ylmethyl)-sulfamoyl]-phenyl}-propionamide;

2-(4-Butyrylsulfamoyl-phenyl)-3-cyclopentyl-N-(5-methoxy-thiazolo[5,4-b]pyridin-2-yl)-propionamide;

2-[4-(4-Cyanomethyl-piperazine-1-sulfonyl)-phenyl]-3-cyclopentyl-N-(5-methoxy-thiazolo[5,4-b]pyridin-2-yl)-propionamide;

3-{4-[2-Cyclopentyl-1-(5-methoxy-thiazolo[5,4-b]pyridin-2-ylcarbamoyl)-ethyl]-benzenesulfonylamino}-propionic acid ethyl ester;

3-Cyclopentyl-N-(5-methoxy-thiazolo[5,4-b]pyridin-2-yl)-2-{4-[methyl-(1-methyl-1H-imidazol-2-ylmethyl)-sulfamoyl]-phenyl}-propionamide;

3-{4-[2-Cyclopentyl-1-(5-methoxy-thiazolo[5,4-b]pyridin-2-ylcarbamoyl)-ethyl]-benzenesulfonylamino}-propionic acid;

3-Cyclopentyl-N-(5-methoxy-thiazolo[5,4-b]pyridin-2-yl)-2-{4-[3-(4-methyl-piperazin-1-yl)-3-oxo-propylsulfamoyl]-phenyl}-propionamide;

3-Cyclopentyl-2-{4-[2-(4-hydroxy-piperidin-1-yl)-ethylsulfamoyl]-phenyl}-N-(5-methoxy-thiazolo[5,4-b]pyridin-2-yl)-propionamide;

2-[4-(4-Cyclobutyl-piperazine-1-sulfonyl)-phenyl]-3-cyclopentyl-N-(5-methoxy-thiazolo[5,4-b]pyridin-2-yl)-propionamide;

2-[4-(4-Allyl-piperazine-1-sulfonyl)-phenyl]-3-cyclopentyl-N-(5-methoxy-thiazolo[5,4-b]pyridin-2-yl)-propionamide;

(1-{4-[2-Cyclopentyl-1-(5-methoxy-thiazolo[5,4-b]pyridin-2-ylcarbamoyl)-ethyl]-benzenesulfonyl}-azetidin-3-ylamino)-acetic acid;

3-Cyclopentyl-N-(5-methoxy-thiazolo[5,4-b]pyridin-2-yl)-2-[4-(2-piperidin-1-ylmethyl-phenylsulfamoyl)-phenyl]-propionamide;

3-Cyclopentyl-2-{4-[4-(2-dimethylamino-ethyl)-phenylsulfamoyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-(4-propionylsulfamoyl-phenyl)-propionamide;

[3-({4-[2-Cyclopentyl-1-(5-methoxy-thiazolo[5,4-b]pyridin-2-ylcarbamoyl)-ethyl]-benzenesulfonylamino}-methyl)-azetidin-1-yl]-acetic acid;

3-Cyclopentyl-N-(5-methoxy-thiazolo[5,4-b]pyridin-2-yl)-2-{4-[4-(2,2,2-trifluoro-acetyl)-piperazine-1-sulfonyl]-phenyl}-propionamide;

3-Cyclopentyl-2-[4-(3-isopropylamino-azetidine-1-sulfonyl)-phenyl]-N-(5-methoxy-thiazolo[5,4-b]pyridin-2-yl)-propionamide;

3-Cyclopentyl-2-[4-(1-isopropyl-azetidin-3-ylsulfamoyl)-phenyl]-N-(5-methoxy-thiazolo[5,4-b]pyridin-2-yl)-propionamide;

3-Cyclopentyl-2-{4-[(1-isopropyl-azetidin-3-ylmethyl)-sulfamoyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[(oxazol-2-ylmethyl)-sulfamoyl]-phenyl}-propionamide;

3-Cyclopentyl-2-{4-[4-(2-methanesulfonyl-ethyl)-piperazine-1-sulfonyl]-phenyl}-N-(5-methoxy-thiazolo[5,4-b]pyridin-2-yl)-propionamide;

2-{4-[4-(3-Cyano-propyl)-piperazine-1-sulfonyl]-phenyl}-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(tetrahydro-pyran-4-ylsulfamoyl)-phenyl]-propionamide;

3-Cyclopentyl-N-(5-methoxy-thiazolo[5,4-b]pyridin-2-yl)-2-{4-[1-(tetrahydro-pyran-4-yl)-azetidin-3-ylsulfamoyl]-phenyl}-propionamide;

4-{4-[2-Cyclopentyl-1-(5-methoxy-thiazolo[5,4-b]pyridin-2-ylcarbamoyl)-ethyl]-benzenesulfonyl}-3-hydroxymethyl-piperazine-1-carboxylic acid tert-butyl ester;

(S)-2-tert-Butoxycarbonylamino-4-{4-[2-cyclopentyl-1-(5-methoxy-thiazolo[5,4-b]pyridin-2-ylcarbamoyl)-ethyl]-benzenesulfonylamino}-butyric acid tert-butyl ester;

S)-2-Amino-4-{4-[2-cyclopentyl-1-(5-methoxy-thiazolo[5,4-b]pyridin-2-ylcarbamoyl)-ethyl]-benzenesulfonylamino}-butyric acid;

3-Cyclopentyl-2-{4-[4-(2-imidazol-1-yl-ethyl)-piperazine-1-sulfonyl]-phenyl}-N-(5-methoxy-thiazolo[5,4-b]pyridin-2-yl)-propionamide;

3-Cyclopentyl-2-[4-(2-hydroxymethyl-piperazine-1-sulfonyl)-phenyl]-N-(5-methoxy-thiazolo[5,4-b]pyridin-2-yl)-propionamide;

(4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid;

3-Cyclopentyl-2-{4-[(2-methoxy-ethyl)-(1-methyl-piperidin-4-yl)-sulfamoyl]-phenyl}-N-(5-methoxy-thiazolo[5,4-b]pyridin-2-yl)-propionamide;

3-Cyclopentyl-2-{4-[(2-methoxy-ethyl)-pyridin-2-ylmethyl-sulfamoyl]-phenyl}-N-(5-methoxy-thiazolo[5,4-b]pyridin-2-yl)-propionamide hydrochloride;

3-Cyclopentyl-2-{4-[(2-hydroxy-ethyl)-(1-methyl-piperidin-4-yl)-sulfamoyl]-phenyl}-N-(5-methoxy-thiazolo[5,4-b]pyridin-2-yl)-propionamide;

2-[4-(4-Benzooxazol-2-yl-piperazine-1-sulfonyl)-phenyl]-3-cyclopentyl-N-(5-methoxy-thiazolo[5,4-b]pyridin-2-yl)-propionamide;

3-Cyclopentyl-2-[4-(furan-2-ylmethyl-methyl-sulfamoyl)-phenyl]-N-(5-methoxy-thiazolo[5,4-b]pyridin-2-yl)-propionamide;

3-Cyclopentyl-2-[4-(3-hydroxy-4,7-dihydro-5H-isoxazolo[5,4-c]pyridine-6-sulfonyl)-phenyl]-N-(5-methoxy-thiazolo[5,4-b]pyridin-2-yl)-propionamide;

2-[4-((S)-1-Benzyl-piperidin-3-ylsulfamoyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[4-(2,2,2-trifluoro-ethyl)-piperazine-1-sulfonyl]-phenyl}-propionamide;

({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-acetic acid ethyl ester hydrochloride;

3-Cyclopentyl-N-(5-methoxy-thiazolo[5,4-b]pyridin-2-yl)-2-[4-(4-pyridin-3-ylmethyl-piperazine-1-sulfonyl)-phenyl]-propionamide hydrochloride;

1'-{4-[2-Cyclopentyl-1-(5-methoxy-thiazolo[5,4-b]pyridin-2-ylcarbamoyl)-ethyl]-benzenesulfonyl}-[1,4']bipiperidinyl-4-carboxylic acid ethyl ester hydrochloride;

1'-{4-[2-Cyclopentyl-1-(5-methoxy-thiazolo[5,4-b]pyridin-2-ylcarbamoyl)-ethyl]-benzenesulfonyl}-[1,4']bipiperidinyl-4-carboxylic acid hydrochloride;

3-Cyclopentyl-N-(5-methoxy-thiazolo[5,4-b]pyridin-2-yl)-2-{4-[2-(1-methyl-pyrrolidin-2-yl)-ethylsulfamoyl]-phenyl}-propionamide;

({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-acetic acid;

3-({4-[2-Cyclopentyl-1-(5-methoxy-thiazolo[5,4-b]pyridin-2-ylcarbamoyl)-ethyl]-benzenesulfonyl}-furan-2-ylmethyl-amino)-propionic acid ethyl ester;

2-{4-[(2-Cyano-ethyl)-furan-2-ylmethyl-sulfamoyl]-phenyl}-3-cyclopentyl-N-(5-methoxy-thiazolo[5,4-b]pyridin-2-yl)-propionamide;

3-Cyclopentyl-2-{4-[(3-methoxy-propyl)-(1-methyl-piperidin-4-yl)-sulfamoyl]-phenyl}-N-(5-methoxy-thiazolo[5,4-b]pyridin-2-yl)-propionamide;

3-Cyclopentyl-2-{4-[(2-diethylamino-ethyl)-(1-methyl-piperidin-4-yl)-sulfamoyl]-phenyl}-N-(5-methoxy-thiazolo[5,4-b]pyridin-2-yl)-propionamide;

3-Cyclopentyl-2-{4-[(3-diethylamino-propyl)-(1-methyl-piperidin-4-yl)-sulfamoyl]-phenyl}-N-(5-methoxy-thiazolo[5,4-b]pyridin-2-yl)-propionamide;

3-({4-[2-Cyclopentyl-1-(5-methoxy-thiazolo[5,4-b]pyridin-2-ylcarbamoyl)-ethyl]-benzenesulfonyl}-furan-2-ylmethyl-amino)-propionic acid;

3-Cyclopentyl-N-(5-methoxy-thiazolo[5,4-b]pyridin-2-yl)-2-[4-(3-phenyl-piperazine-1-sulfonyl)-phenyl]-propionamide;

3-Cyclopentyl-N-(5-methoxy-thiazolo[5,4-b]pyridin-2-yl)-2-[4-(3,3,4-trimethyl-piperazine-1-sulfonyl)-phenyl]-propionamide;

3-Cyclopentyl-2-[4-(3,3-dimethyl-piperazine-1-sulfonyl)-phenyl]-N-(5-methoxy-thiazolo[5,4-b]pyridin-2-yl)-propionamide;

4-{4-[2-Cyclopentyl-1-(5-methoxy-thiazolo[5,4-b]pyridin-2-ylcarbamoyl)-ethyl]-benzenesulfonyl}-piperazine-1,3-dicarboxylic acid 1-tert-butyl ester;

3-Cyclopentyl-N-(5-methoxy-thiazolo[5,4-b]pyridin-2-yl)-2-[4-(4-methyl-3-phenyl-piperazine-1-sulfonyl)-phenyl]-propionamide; and 3-Cyclopentyl-2-[4-(2,5-diaza-bicyclo[2.2.1]heptane-2-sulfonyl)-phenyl]-N-(5-methoxy-thiazolo[5,4-b]pyridin-2-yl)-propionamide;

or an enantiomer thereof; or an enantiomeric mixture thereof; or a pharmaceutically acceptable salt thereof.

Compounds of formula (I) may be prepared using methods well known in the art, e.g., according to Method A or Method B as outlined herein below.

Method A:

Compounds of formula (I) may be obtained by coupling an amine of the formula

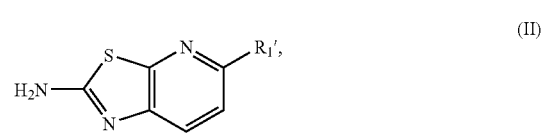

or acid addition salts thereof, wherein $R_1'$ represents $R_1$ as defined herein above, or $R_1'$ is a group convertible to $R_1$, with an activated derivative of a carboxylic acid of the formula

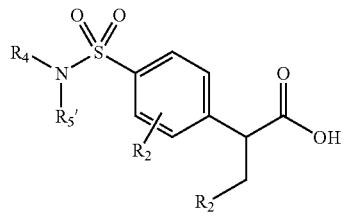

(III)

wherein $R_2$, $R_3$ and $R_4$ have meanings as defined herein, and $R_5'$ represents $R_5$ as defined herein above, or $R_5'$ is a group convertible to $R_5$, to afford a compound of the formula

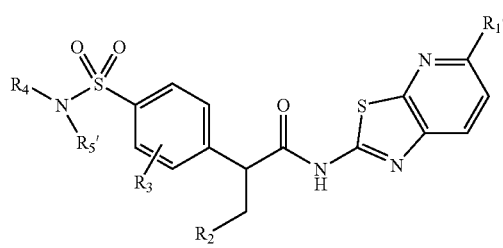

(I')

wherein $R_1'$, $R_2$, $R_3$, $R_4$ and $R_5'$ have meanings as defined for formulae (II) and (III).

In the coupling reaction cited herein above, an activated derivative of a carboxylic acid, e.g., those corresponding to carboxylic acids of formula (III), include acid chlorides, bromides and fluorides, mixed anhydrides, lower alkyl esters and activated esters thereof, and adducts formed with coupling agents, such as 1-ethyl-3-(3-dimethylaminopropyl)carbodiimide hydrochloride (EDCI), 1-hydroxy benzotriazole (HOBt), O-(1,2-dihydro-2-oxo-1-pyridyl)-N,N,N',N'-tetramethyluronium tetrafluoroborate, benzotriazole-1-yl-oxy-tris-pyrrolidino-phosphonium hexafluorophosphate (PyBOP) and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those corresponding to carboxylic acids of formula (III), with an amine, e.g., those of formula (II), may be carried out in the presence of a base, such as pyridine, triethylamine (TEA), diisopropylethylamine (DIEA) or N-methylmorpholine (NMM) in an inert organic solvent, such as dichloromethane (DCM), N,N-dimethylformamide (DMF) or tetrahydrofuran (THF), or a mixture of solvents thereof. Carboxylic acids of formula (III) may be converted to their activated derivatives using methods described herein or according to methods generally known in the art, e.g., a carboxylic acid of formula (III) may be treated with a chlorinating agent, such as thionyl chloride or oxalyl chloride, to afford a corresponding acid chloride thereof, or by the treatment of a coupling agent such as EDCI or HOBt, or a mixture of coupling agents thereof.

Amines of formula (II) and carboxylic acids of formula (III) are known, or if they are novel they may be prepared using methods described herein in the illustrative Examples, or modifications thereof, or using methods well known in the art. For example, compounds of formula (III) may be prepared by treating an ester of the formula

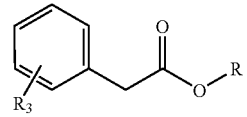

(IV)

wherein $R_3$ has a meaning as defined herein above, and R is lower alkyl, preferably, methyl or ethyl, with chlorosulfonic acid to afford a compound of the formula

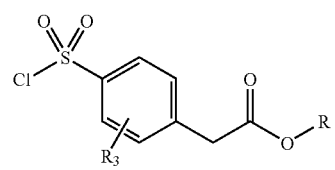

(V)

wherein $R_3$ and R have meanings as defined herein above, optionally in the presence of an intrinsic organic solvent. Preferably, the reaction is carried out without an intrinsic organic solvent.

A compound of formula (V) may then be treated with an amine of the formula

$R_4$—NH—$R_5'$ (VI), or an acid addition salt thereof, wherein $R_4$ and $R_5'$ have meanings as defined herein above, in the presence of a base, such as pyridine, TEA, DIEA or NMM, in an inert organic solvent, such as DCM, DMF or THF, or a mixture of solvents thereof, to afford a compound of the formula

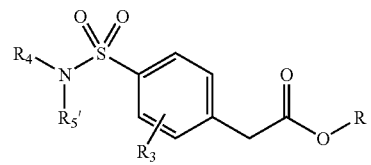

(VII)

wherein $R_3$, $R_4$, $R_5'$ and R have meanings as defined herein above. Preferably, the reaction is conducted at a temperature ranging from about $-4°$ C. to room temperature (RT), more preferably, the reaction temperature is about $0°$ C.

A resulting compound of formula (VII) may then be treated with a base, such as sodium hydride, lithium diisopropylamide (LDA) or lithium bis(trimethylsilyl)amide (LHMDS), preferably LDA, followed by addition of an alkylating agent of the formula

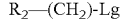

$R_2$—(CH$_2$)-Lg (VIII)

wherein $R_2$ has a meaning as defined herein above, and Lg represents a leaving group, such as chloride, bromide, iodide, mesylate, tosylate or triflate, preferably iodide, to afford a compound of the formula

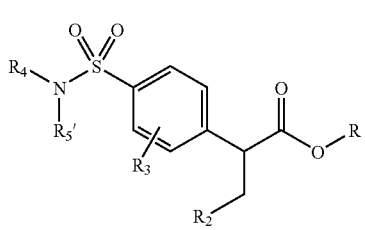

(IX)

wherein $R_2$, $R_3$, $R_4$, $R_5'$ and R have meanings as defined herein above. The alkylation step is preferably conducted in a polar organic solvent, such as THF, DMF, N-methylpyrrolidone (NMP), 1,3-dimethyl-3,4,5,6-tetrahydro-2(1H)-pyridone (DMPU) or 1,3-dimethyl-3,4,5,6-tetrahydro-2(1H)-pyrimidinone (DMTP), or in a mixture of solvents thereof.

A resulting compound of formula (IX) may then be hydrolyzed, e.g., in the presence of an aqueous base such as sodium, lithium or potassium hydroxide and an organic solvent such as THF or lower alcohol, preferably, methanol or ethanol, to afford a carboxylic acid of formula (III) wherein $R_2$, $R_3$, $R_4$ and $R_5'$ have meanings as defined herein above.

A carboxylic acid of formula (III) may then be coupled with an amine of formula (II) under reaction conditions as described herein above to afford a compound of formula (I') wherein $R_1'$, $R_2$, $R_3$, $R_4$ and $R_5'$ have meanings as defined herein above, e.g., via conversion of the acid to the corresponding acid chloride or in the presence of a coupling agent such as EDCI, HOBt or PyBOP, or a mixture of coupling agents thereof.

Alternatively, compounds of formula (I) may be prepared as outlined herein below.

Method B:

Compounds of formula (I) may be obtained by reacting a compound of the formula

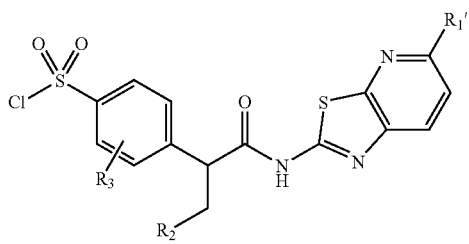

(X)

wherein $R_2$ and $R_3$ have meanings as defined herein above, and $R_1'$ represents $R_1$ as defined herein above, or $R_1'$ is a group convertible to $R_1$, with an amine of the formula

 (VI), or an acid addition salt thereof, wherein $R_4$ has a meaning as defined herein, and $R_5'$ represents $R_5$ as defined herein above, or $R_5'$ is a group convertible to $R_5$, in the presence of a base, such as pyridine, TEA, DIEA or NMM, in an inert organic solvent, such as DCM, DMF or THF, or a mixture of solvents thereof, to afford a compound of the formula

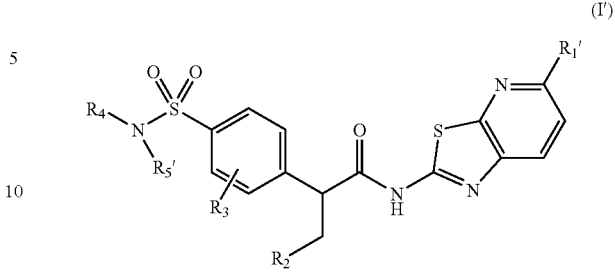

(I')

wherein $R_1'$, $R_2$, $R_3$, $R_4$ and $R_5'$ have meanings as defined herein above.

Compounds of formula (X) may be prepared, e.g., by treating a compound of the formula

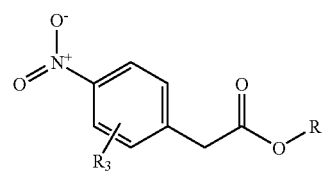

(XI)

wherein $R_3$ and R have meanings as defined herein above, with a base, such as sodium hydride, LDA or LHMDS, preferably LDA, followed by addition of an alkylating agent of the formula

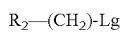 (VIII)

wherein $R_2$ has a meaning as defined herein above, and Lg represents a leaving group, such as chloride, bromide, iodide, mesylate, tosylate or triflate, preferably iodide, to afford a compound of the formula

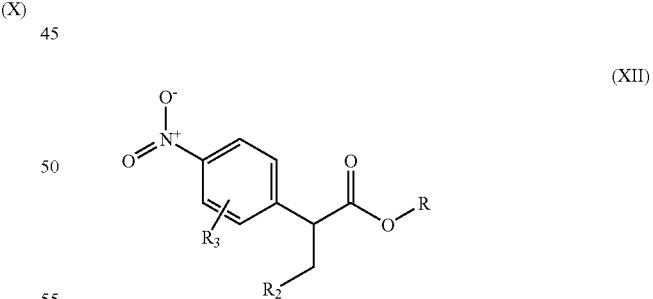

(XII)

wherein $R_2$, $R_3$ and R have meanings as defined herein above. The alkylation step is preferably conducted in a polar organic solvent, such as THF, DMF, NMP, DMPU or DMTP, or in a mixture of solvents thereof.

A resulting compound of formula (XII) may then be hydrolyzed, e.g., in the presence of an aqueous base, such as sodium, lithium or potassium hydroxide and an organic solvent such as THF or lower alcohol, preferably, methanol or ethanol, to afford a carboxylic acid of the formula

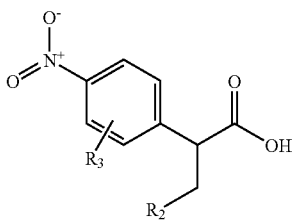

(XIII)

wherein $R_2$ and $R_3$ have meanings as defined herein above.

A carboxylic acid of formula (XIII) may then be coupled with an amine of formula (II) under reaction conditions as described herein above to afford a compound of the formula

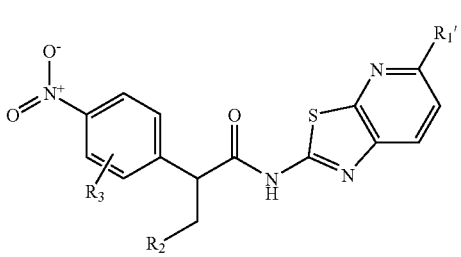

(XIV)

wherein $R_1'$, $R_2$ and $R_3$ have meanings as defined herein above, e.g., via conversion of the acid to the corresponding acid chloride or in the presence of a coupling agent, such as EDCI, HOBt or PyBOP, or a mixture of coupling agents thereof.

A resulting compound of formula (XIV) may then be converted to a sulfonyl chloride derivative of the formula

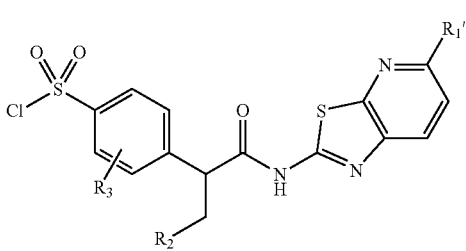

(XV)

wherein $R_1'$, $R_2$ and $R_3$ have meanings as defined herein above, by reduction of the nitro group to the amino group, e.g., using iron powder in the presence of a mixture of acetic acid and a lower alcohol, such as ethanol, followed by diazotization reaction and subsequent treatment with, e.g., sulfur dioxide in the presence of copper(II) chloride and acetic acid.

Finally, a sulfonyl chloride derivative of formula (XV) may be treated with an amine of the formula

  (VI), or an acid addition salt thereof, wherein $R_4$ and $R_5'$ have meanings as defined herein above, in the presence of a base, such as pyridine, TEA, DIEA or NMM, in an inert organic solvent, such as DCM, DMF or THF, or a mixture of solvents thereof, to afford a compound of formula (I') wherein $R_1'$, $R_2$, $R_3$, $R_4$ and $R_5'$ have meanings as defined herein above.

The processes described herein above may be conducted under inert atmosphere, preferably under nitrogen atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediate, e.g., acids of formulae (III) and (XIII), can be resolved into the optical antipodes by known methods, e.g., by separation of the diastereomeric salts thereof, obtained with an optically active acid or base and liberating the optically active acidic or basic compound, e.g., acids of formulae (III) and (XIII) can be resolved using 1-phenylethylamine. Furthermore, the thiazolopyridine moiety may be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-ρ-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the invention are either obtained in the free form, or in a salt form thereof, preferably, in a pharmaceutically acceptable salt form thereof, or as a prodrug derivative thereof.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention, in general, may be converted into acid addition salts, especially pharmaceutically acceptable salts. These are formed, e.g., with inorganic acids, such as mineral acids, e.g., sulfuric acid, phosphoric or hydrohalic acid, or with organic carboxylic acids, such as ($C_1$-$C_4$)-alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as ($C_1$-$C_4$)-alkylsulfonic acids, e.g., methanesulfonic acid; or arylsulfonic acids which are unsubstituted or substituted (for example by halogen). Preferred are salts formed with hydrochloric acid, maleic acid and methanesulfonic acid.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the corn pounds of the present invention may be employed for the treatment of conditions mediated by glucokinase activity. Such compounds may thus be employed therapeutically for the treatment of impaired glucose tolerance, Type 2 diabetes and obesity.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by glucokinase activity. Such conditions include impaired glucose tolerance, Type 2 diabetes and obesity.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by glucokinase activity, preferably, impaired glucose tolerance, Type 2 diabetes and obesity.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1 B (PTP-1 B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by glucokinase activity, preferably, impaired glucose tolerance, Type 2 diabetes and obesity.

Thus, the present invention also relates to a compound of formula (I) for use as a medicament; to the use of a compound of formula (I) for the preparation of a pharmaceutical composition for the prevention and/or treatment of conditions mediated by glucokinase activity, and to a pharmaceutical composition for use in conditions mediated by glucokinase activity comprising a compound of formula (I), or a pharmaceutically acceptable salt thereof, in association with a pharmaceutically acceptable diluent or carrier therefore.

The present invention further provides a method for the prevention and/or treatment of conditions mediated by glucokinase activity, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents and anti-hypertensive agents, or a pharmaceutically acceptable salt thereof. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent and an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of the glucokinase activity.

Preferably, the condition associated with glucokinase activity is selected from impaired glucose tolerance, Type 2 diabetes and obesity.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.1 mg/kg and 1000 mg/kg, preferably between about 1 mg/kg and 100 mg/kg.

The activity of compounds according to the invention may be assessed by the following methods or methods well-described in the art:

The glucokinase activation in vitro may be determined by measuring the activation of recombinant GST-GK by a compound of the present invention in the absence or the presence of GKRP, a 68,000 Da protein inhibitor of GK. In these assays, formation of glucose-6-phosphate is coupled directly to the formation of thioNADH. GST-GK catalyzes the reaction of glucose and Mg-ATP to produce glucose-6-phosphate and ADP. Glucose-6-phosphate dehydrogenase (G6PDH) reduces thionicotinamide (thioNAD) to thioNADH. The assay measures the formation of NADH at 405 nM.

The basic GK assay components are as follows: 25 mM HEPES (pH 7.1), 25 mM KCl, 2.5 mM $MgCl_2$, 1 mM ATP (Sigma A-5394), 1 mM DTT, 1 mM thioNAD (Sigma T-7375), 80 units/mL G6PDH (Sigma G-5885), 10 mM glucose and 8.7 mg/mL GST-GK (110 nM). For assessing reversal of GK inhibition by GKRP, 20 µM Fructose-1-phosphate (F-6-P) and 25 µg/mL of recombinant GKRP (370 nM) are added to these assay components. F-1-P at 1 µM is used as a control in the GK/GKRP assay. F-1-P reverses inhibition of GST-GK by GKRP.

The assay is done in standard, 96-well, round-bottom plates and the total assay volume is 25 µL. Compounds are serially diluted into 100% DMSO and 0.5 µL of diluted compound in 100% DMSO is added to the assay plate. Assay reagents (24.5 µL) are added using a Zymark robotic platform. Buffer, containing HEPES, $MgCl_2$, KCl, thioNAD, G6PDH, F-6-P, glucose, GKRP and GST-GK, are added (5 µL) using the Zymark 8-channel hand pipet. The reaction is then initiated by adding 19.5 µL of buffer containing HEPES, $MgCl_2$, KCl, DTT and ATP using the Zymark Reagent Addition Station/Reagent Addition Module. The plates are then delivered via the Zymark XP arm to a Thermomax plate reader and read kinetically over three min at 405 nM at RT. Units are expressed as milli-optical density per minute (mOD/min).

The glucokinase activation in rat hepatocytes may be determined as follows:

Hepatocytes are isolated by collagenase perfusion of the livers of overnight-fasted male Harlen Sprague-Dawley rats (Charles River Laboratories, Raleigh, N.C.) as previously described (see Berry et al., *J. Cell Biol.*, Vol. 43, pp. 506-520 (1969)). The cells are washed three times each with 100 mL of glucose-free Dulbecco's Modified Eagle medium (DMEM, Gibco BRL) containing 5% fetal bovine serum (FBS) and then suspended in glucose-free DMEM/5% FBS. Cells are plated in collagen coated 24-well plates (Becton Dickinson) at a density of $3 \times 10^5$ cells/well in 1 mL of William's Medium E (Sigma) supplemented with 5% FBS, and incubated at 37° C. in 5% $CO_2$/95% air. After cell attachment (~4 h), the medium is replaced with serum-free DMEM containing 5 mM glucose and 10 nM dexamethasone (Sigma), and cells are cultured further for 16-20 h prior to use.

The rate of glucose phosphorylation is determined by the release of $^3H_2O$ from [2-$^3$H]glucose. The medium from the cultured hepatocytes is removed, and the cells are pre-incubated in 150 µL of fresh serum-free DMEM containing 5 mM glucose and compound (1, 10 and 30 µM) or DMSO for 3 h at 37° C. The final concentration of DMSO is 0.2%. The medium is then removed and 150 µL of a fresh mixture of DMEM/5 mM glucose containing compound or DMSO, and 1 µCi of [2-$^3$H]glucose (NEN) is added. As a positive control for stimulation of glucose phosphorylation, cells are preincubated in serum-free DMEM/5 mM glucose medium containing DMSO for 3 h and then are incubated for 1 h in labeled glucose medium containing 0.5 mM fructose/DMSO (precursor of F-1-P, AnalaR® from BDH). All conditions are tested in quadruplicate where one well per plate received 200 µL of the appropriate medium plus labeled glucose (instead of 150 µL) of which 50 µL is immediately removed and placed in a 1.2 mL microfuge tube (Costar) containing 10 µL of 1 N HCl. This sample is used as a 0-minute time point for determining background $^3H_2O$ release (exchange values). Following the addition of the labeled glucose media, hepatocytes are incubated at 37° C. on a slow moving rocker for 1 h.

On termination of the incubation, 50 µL of the culture medium is collected into microfuge tubes containing 10 µL of 1 N HCl, and determination of $^3H_2O$. The tubes are left uncapped and each is placed inside a 20 mL glass scintillation vial (Wheaton) containing 1.5 mL of deionized water. The vials are capped tightly and incubated at 37° C. in a dry incubator for 2 days ($^3H_2O$ from the reaction mixture will equilibrate with the water in the vial). A standard curve is generated using [$^3$H]$H_2O$ (NEN) to correct for exchange. 50 µL aliquots of serial dilutions of the labeled water are added to 10 µL of 1 N HCl and exchange is performed as described for the samples (typically, approximately 90% exchange is observed). The microfuge tubes are then removed from the vials carefully to minimize the removal of any water from the vial and 18 mL of scintillation cocktail (Ready Safe, Beckman Coulter) is then added to each vial. The $^3$H-label recovered from [2-$^3$H]glucose in the water is determined using a Beckman Model LS500 scintillation counter and the counts (minus the 0-time point) are corrected for recovery of $^3H_2O$. The amount of glucose de-tritiated in nanomoles/h per $10^6$ cells is calculated, and the results are expressed as percent increase over the DMSO control.

Illustrative of the invention, the compound of Example 1 demonstrates an $EC_{50}$ of about 251 nM in the in vitro assay measuring the activation of recombinant GST-GK.

The following Examples are intended to illustrate the invention and are not to be construed as being limitations thereon. If not mentioned otherwise, all evaporations are performed under reduced pressure, preferably between about 50 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

The following compounds may be prepared according to Method A.

EXAMPLE 1

3-Cyclopentyl-N-(5-methoxy-thiazolo[5,4-b]pyridin-2-yl)-2-[4-(4-methyl-piperazine-1-sulfonyl)-phenyl]-propionamide

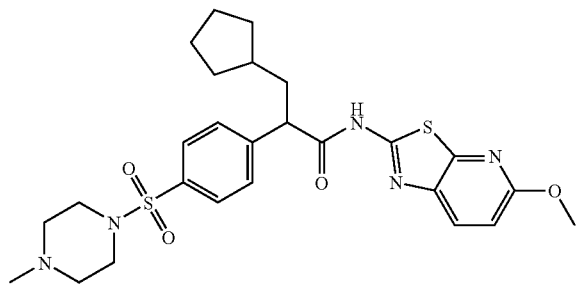

A. Phenylacetic Acid Ethyl Ester

A solution of phenylacetic acid (50 g, 0.36 mol) in ethanol (150 mL) is treated with catalytic amount of sulfuric acid (4 mL). The reaction mixture is refluxed for 4 h. The reaction is then concentrated in vacuo. The residue is dissolved in diethyl ether (300 mL) and washed with saturated aqueous sodium bicarbonate solution (2×50 mL) and water (1×100 mL). The organic layer dried over sodium sulfate filtered and concentrated in vacuo to give phenylacetic acid ethyl ester as a colorless oil: $^1$H NMR (400 MHz, CDCl$_3$) δ 1.2 (t, J=7.2, 3H), 3.6 (s, 2H), 4.1 (q, J=7.2, 2H), 7.3 (m, 5H); MS 165 [M+1]$^+$.

B. (4-Chlorosulfonyl-phenyl)-acetic acid ethyl ester

To a cooled chlorosulfonic acid (83.83 g, 48 mL, 0.71 mol) under nitrogen is added the title A compound, phenylacetic acid ethyl ester (59 g, 0.35 mol) over a period of 1 h. Reaction temperature is brought to RT (28° C.), then heated to 70° C., maintaining it at this temperature for 1 h while stirring. Reaction is cooled to RT and poured over saturated aqueous sodium chloride solution (200 mL) followed by extraction with DCM (2×200 mL). The organic layer is washed with water (5×100 mL), followed by saturated aqueous sodium chloride solution (1×150 mL). The organic layer dried over sodium sulfate, filtered and concentrated in vacuo to give crude (4-chlorosulfonyl-phenyl)acetic acid ethyl ester. Further column chromatography over silica gel (60-120 mesh), using 100% hexane afforded pure (4-chlorosulfonyl-phenyl)-acetic acid ethyl ester as a colorless oil.

C. [4-(4-Methyl-piperazine-1-sulfonyl)-phenyl]-acetic acid ethyl ester

A solution of N-methylpiperazine (9.23 g, 10.21 ml, 0.092 mol), DIEA (13 g, 17.4 mL, 0.10 mol) and DCM 80 mL is cooled to 0° C., and to this is added a solution of the title B compound, (4-chlorosulfonyl-phenyl)-acetic acid ethyl ester (22 g, 0.083 mol) in 50 mL of DCM within 30 min. Reaction mixture stirred at 0° C. for 2 h, and the reaction mixture is washed with water (100 mL), followed by 0.1 N aqueous hydrochloric acid solution (1×200 mL). The organic layer dried over sodium sulfate, filtered and concentrated under vacuo to give crude [4-(4-methyl-piperazine-1-sulfonyl)-phenyl]-acetic acid ethyl ester. Column chromatography over silicagel (60-120 mesh), using ethyl acetate afforded pure [4-(4-methyl-piperazine-1-sulfonyl)-phenyl]-acetic acid ethyl ester as white crystalline solid: $^1$H NMR (400 MHz, CDCl$_3$) δ 1.3 (t, J=7.4, 3H), 2.3 (s, 3H), 2.5 (m, 4H), 3.0 (br s, 4H), 3.7 (s, 2H), 4.2 (q, J=7.4, 2H), 7.4 (d, J=8.3, 2H), 7.7 (d, J=7.3, 2H); MS 327 [M+1]$^+$.

D. 3-Cyclopentyl-2-[4-(4-methyl-piperazine-1-sulfonyl)-phenyl]-propionic acid ethyl ester A solution of the title C compound, [4-(4-methyl-piperazine-1-sulfonyl)-phenyl]-acetic acid ethyl ester (15 g, 0.046 mol) in a mixture of THF (60 mL) and DMTP (10 mL) is cooled to −78° C. under nitrogen. The resulting solution is stirred at −78° C. for 45 min and to this is added LDA (25.6 mL, 6.40 g, 0.059 mol, 25% solution in THF/Hexane). A solution of iodomethylcyclopentane (11.60 g, 0.055 mol) in a mixture of DMTP (12 mL) and THF (20 mL) is added over a period of 15 min at −78° C. and reaction mixture stirred at −78° C. for 3 h further, followed by stirring at 25° C. for 12 h. The reaction mixture is then quenched by the dropwise addition of saturated aqueous ammonium chloride solution (50 mL) and is concentrated in vacuo. The residue is diluted with water (50 mL) and extracted with ethyl acetate (3×100 mL). The organic solution is washed with a saturated aqueous sodium chloride (2×150 mL), dried over sodium sulfate, filtered and concentrated in vacuo. Column chromatography over silica gel (60-120 mesh), using 50% ethyl acetate in hexane as an eluent to afford 3-cyclopentyl-2-[4-(4-methyl-piperazine-1-sulfonyl)-phenyl]-propionic acid ethyl ester as a white solid: $^1$H NMR (400 MHz, CDCl$_3$) δ 0.9-2.1 (m, 11H), 1.2 (t, J=7.1, 3H), 2.3 (s, 3H), 2.5 (br s, 4H), 3.0 (br s, 4H), 3.6 (m, 1H), 4.1 (q, J=7.1, 2H), 7.5 (d, J=8.3, 2H), 7.7 (d, J=8.3, 2H); MS 409 [M+1]$^+$.

E. 3-Cyclopentyl-2-[4-(4-methyl-piperazine-1-sulfonyl)-phenyl]-propionic acid A solution of the title D compound, 3-cyclopentyl-2-[4-(4-methyl-piperazine-1-sulfonyl)-phenyl]-propionic acid ethyl ester (14 g, 0.034 mol) in methanol:water (30 mL:10 mL) and sodium hydroxide (4.11 g, 0.10 mol) is stirred at 60° C. for 8 h in an oil bath. The methanol is then removed in vacuo at 45-50° C. The residue is diluted with water (25 mL) and extracted with ether (1×40 mL). The aqueous layer is acidified to pH 5 with 3 N aqueous hydrochloric acid solution. The precipitated solid is collected by vacuum filtration, washed with water (20 mL), followed by isopropyl alcohol (20 mL). Finally, solid cake is washed with 100 mL of hexane and dried under vacuum at 40° C. for 6 h to give 3-cyclopentyl-2-[4-(4-methyl-piperazine-1-sulfonyl)-phenyl]-propionic acid as a white solid: $^1$H NMR (400 MHz, CDCl$_3$) δ 1.1-2.0 (m, 11H), 2.4 (s, 3H), 2.7 (br s, 4H), 3.1 (br s, 4H), 3.6 (m, 1H), 7.5 (d, J=8.3, 2H), 7.6 (d, J=8.3, 2H); MS 381 [M+l]$^+$.

F. 5-Methoxy-thiazolo[5,4-b]pyridin-2-ylamine

A solution of 6-methoxy-pyridin-3-ylamine (5.0 g, 0.0403 mol) in 10 mL of acetic acid is added slowly to a solution of potassium thiocyanate (20 g, 0.205 mol) in 100 mL of acetic acid at 0° C. followed by a solution of bromine (2.5 mL, 0.0488 mol) in 5 mL of acetic acid. The reaction is stirred for 2 h at 0° C. and then allowed to warm to RT. The resulting solid is collected by filtration and washed with acetic acid, then partitioned between ethyl acetate and saturated aqueous sodium bicarbonate. The insoluble material is removed by filtration and the organic layer is evaporated and dried to afford 5-methoxy-thiazolo[5,4-b]pyridin-2-ylamine as a tan solid.

G. 3-Cyclopentyl-N-(5-methoxy-thiazolo[5,4-b]pyridin-2-yl)-2-[4-(4-methyl-piperazine-1-sulfonyl)-phenyl]-propionamide A solution of the title E compound, 3-cyclopentyl-2-[4-(4-methyl-piperazine-1-sulfonyl)-phenyl]-propionic acid (5 g, 0.013 mol) in DCM (250 mL) is cooled to 0° C. and then charged HOBt hydrate (2.66 g, 0.019 mol), followed by EDCI hydrochloride (6 g, 0.031 mol). The reaction mixture is stirred at 0° C. for 5 h. After that the solution of the title F compound, 5-methoxy-thiazolo[5,4-b]pyridin-2-ylamine (2.36 g, 0.013 mol) and D1EA (8 mL, 0.046 mol) in a mixture of DCM (60 mL) and DMF (20 mL) is added dropwise over 30 min. Reaction temperature is maintained at 0° C. for 3 h, then at RT (28° C.) for 3 days. Reaction is diluted with (60 mL) of water and the organic layer is separated and washed with saturated sodium bicarbonate solution (2×50 mL) followed by water washing (2×50 mL) and saturated sodium chloride aqueous solution (1×150 mL). Finally the organic layer is dried over sodium sulfate, filtered, and evaporated under vacuo. The crude product is purified using column chromatography over silica gel (60-120 mesh), using 40% ethyl acetate in hexane as an eluent to afford 3-cyclopentyl-N-(5-methoxy-thiazolo[5,4-b]pyridin-2-yl)-2-[4-(4-methyl-piperazine-1-sulfonyl)-phenyl]-propionamide as a white solid: $^1$H NMR (400 MHz, CDCl$_3$) δ 0.9-2.1 (m, 11H), 2.2 (s, 3H), 2.5 (br s, 4H), 3.1 (br s, 4H), 3.7 (m, 1H), 4.0 (s, 3H), 6.8 (d, J=8.8, 1H), 7.5 (d, J=8.3, 2H), 7.7 (d, J=8.3, 2H), 7.8 (d, J=8.8, 1H), 8.6 (s, 1H); MS 617 [M+1]$^+$.

H. 3-Cyclopentyl-N-(5-methoxy-thiazolo[5,4-b]pyridin-2-yl)-2-[4-(4-methyl-piperazine-1-sulfonyl)-phenyl]-propionamide dihydrochloride The title G compound, 3-cyclopentyl-2-(4-methyl piperazinyl sulfonyl)phenyl-N-(5-methoxy-thiazolo[5,4-b]pyridin-2-yl)propionamide (2.8 g, 0.0051 mol) is added to a cooled solution of 10% hydrochloric acid in isopropanol (3.75 mL). The reaction mixture is stirred at 0° C. for 1 h and then at RT for 2 h. The solid is separated, triturated with 10 mL of isopropanol and collected by vacuum filtration and washed with 50 mL of hexane. The solid is dried at 70° C. for 48 h to afford 3-cyclopentyl-N-(5-methoxy-thiazolo[5,4-b]pyridin-2-yl)-2-[4-(4-methyl-piperazine-1-sulfonyl)-phenyl]-propionamide dihydrochloride as an off white solid.

EXAMPLE 2

(R)-3-Cyclopentyl-N-(5-methoxy-thiazolo[5,4-b]pyridin-2-yl)-2-[4-(4-methyl-piperazine-1-sulfonyl)-phenyl]-propionamide

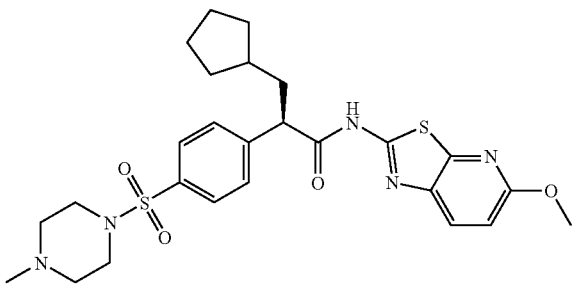

The title compound is obtained analogously to Example 1 by employing the following additional resolution step:

The racemic title E compound of Example 1,3-cyclopentyl-2-[4-(4-methyl-piperazine-1-sulfonyl)-phenyl]-propionic acid (10 g, 0.026 mol) in 1,4-dioxane (500 mL) is treated in a three necked 1 liter flask, equipped with heating mantle, water condenser, calcium chloride guard tube and mechanical stirrer with 3.18 g (0.026 mol) of (R)-(+)-1-phenylethylamine. This reaction mixture is then refluxed at 100° C. for 1 h. The clear reaction solution is cooled to RT (27° C.) and stirred for 10 h. The crystallized salt is collected by filtration under vacuum, washed with 5 mL of hexane and dried under vacuum to afford salt A.

The salt A is dissolved in 1,4-dioxane (500 mL) and heated at 100° C. for 1 h. The clear reaction solution is cooled to RT (27° C.) and stirred for 10 h. The crystallized product is collected by filtration under vacuum, washed with 50 mL of hexane, and dried under vacuum to afford salt B.

The salt B is dissolved in 1,4-dioxane (290 mL) and heated at 100° C. for 1 h. The clear reaction solution is cooled to RT (27° C.) and stirred for 10 h. The crystallized product is collected by filtration under vacuum, washed with 30 mL of hexane, and dried under vacuum to afford salt C.

The salt C is dissolved in 1,4-dioxane (100 mL) and heated at 100° C. for 1 h. The clear reaction solution is cooled to RT (27° C.) and stirred for 10 h. The crystallized product is collected by filtration under vacuum, washed with 30 ml of hexane, and dried under vacuum to afford salt D.

The salt D is treated with aqueous hydrochloric acid solution (20 mL, 1 mL of concentrated hydrochloric acid diluted with 100 mL of water) and stirred for 5 min. The white solid precipitates out and is collected by vacuum filtration, washed with 10 mL of cold water, 5 mL of isopropanol and 20 mL of hexane, and dried under vacuum to yield the hydrochloride salt of (R)-(−)-3-cyclopentyl-2-[4-(4-methyl-piperazine-1-sulfonyl)-phenyl]-propionic acid, salt E.

The salt E is neutralized by stirring with aqueous sodium bicarbonate solution (10 mL, 1 g of sodium bicarbonate dissolved in 120 mL of water) for 5 min. The precipitated solid is collected by filtration, washed with 10 mL of cold water, 100 mL of hexane, and dried to afford (R)-(−)-3-cyclopentyl-2-[4-(4-methyl-piperazine-1-sulfonyl)-phenyl]-propionic acid: m.p. 202.2-203.4° C.

Alternatively, the title compound may be obtained by the resolution of the racemic title compound of Example 1 using the following preparative chiral HPLC method:

Column: Chiralcel OD-R (250×20 mm) Diacel make, Japan;
Solvent A: water:methanol:acetonitrile (10:80:10 v/v/v);
Solvent B: water:methanol:acetonitrile (05:90:05 v/v/v);
Using gradient elution: gradient program (time, min/% B): 0/0, 20/0, 50/100, 55/0, 70/0;
Flow rate: 6.0 mL/min; and
Detection: by UV at 305 nm.

EXAMPLE 3

(S)-3-Cyclopentyl-N-(5-methoxy-thiazolo[5,4-b]pyridin-2-yl)-2-[4-(4-methyl-piperazine-1-sulfonyl)-phenyl]-propionamide

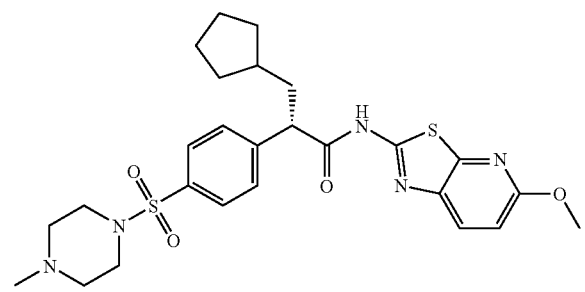

The title compound is prepared analogously to Example 2.

EXAMPLE 4

3-Cyclopentyl-2-(4-cyclopropylsulfamoyl-phenyl)-N-(5-methoxy-thiazolo[5,4-b]pyridin-2-yl)-propionamide

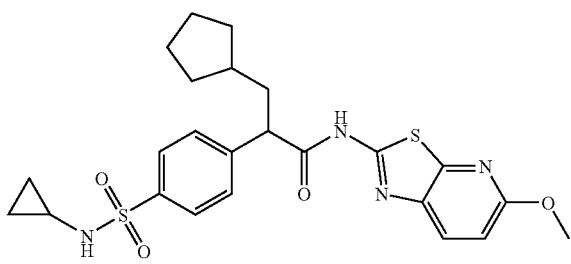

The title compound is prepared analogously to Example 1: MS e/z (ES) 499 (M−1−, 100%); m.p. 235-237° C.; $^1$H NMR (CDCl$_3$) δ 12.68 (s, 1H), 8.03 (d, J=8.8, 1H), 7.89 (d, J=2.4, 1H), 7.80 (d, J=8.4, 2H), 7.63 (d, J=8.4, 2H), 6.91 (d, J=8.8, 1H), 4.08 (t, J=7.2, 1H), 3.91 (s, 3H), 2.14-2.19 (m, 1H), 2.05-2.08 (m, 1H), 1.71-1.85 (m, 3H), 1.56-1.62 (m, 3H), 1.42-1.45 (m, 2H), 1.09-1.16 (m, 2H), 0.44-0.48 (m, 2H), 0.34-0.38 (m, 2H).

EXAMPLE 5

3-Cyclopentyl-2-[4-(2-methoxy-ethylsulfamoyl)-phenyl]-N-(5-methoxy-thiazolo[5,4-b]pyridin-2-yl)-propionamide

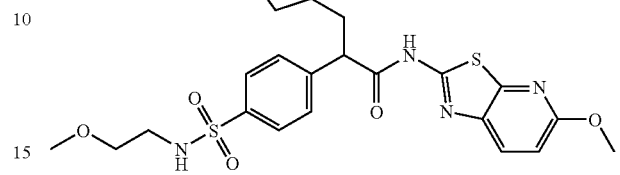

The title compound is prepared analogously to Example 1: MS e/z (ES) 519 (M+1+, 100%); m.p. 209-211° C.; $^1$H NMR (CDCl$_3$) δ 12.66 (s, 1H), 8.03 (d, J=8.8, 1H), 7.78 (d, J=8.4, 2H), 7.69 (t, J=5.6, 1H), 7.61 (d, J=8.4, 2H), 6.90 (d, J=8.8, 1H), 4.06 (t, J=7.6, 1H), 3.91 (s, 3H), 3.24-3.27 (m, 2H), 3.09 (s, 3H), 2.87-2.91 (m, 2H), 2.10-2.18 (m, 1H), 1.78-1.85 (m, 1H), 1.65-1.75 (m, 2H), 1.56-1.61 (m, 3H), 1.42-1.45 (m, 2H), 1.09-1.18 (m, 2H).

EXAMPLE 6

3-Cyclopentyl-2-[4-(3-methoxy-benzylsulfamoyl)-phenyl]-N-(5-methoxy-thiazolo[5,4-b]pyridin-2-yl)-propionamide

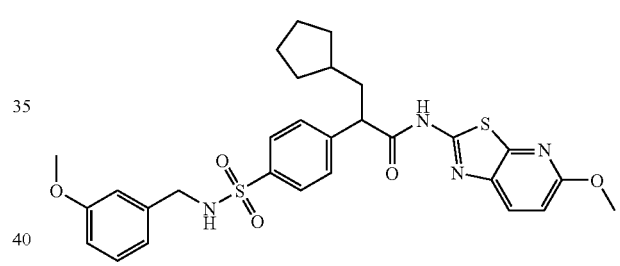

The title compound is prepared analogously to Example 1: MS e/z (ES) 579 (M−1−, 100%); m.p. 179-181° C.; $^1$H NMR (CDCl$_3$) δ 12.67 (s, 1H), 8.15 (t, J=6.4, 1H), 8.04 (d, J=8.8, 1H), 7.72 (d, J=8.0, 2H), 7.55 (d, J=8.4, 2H), 7.08 (t, J=8.0, 1H), 6.91 (d, J=8.8, 1H), 6.70-6.75 (m, 2H), 6.63-6.68 (m, 1H), 4.04 (t, J=7.6, 1H), 3.98 (d, J=6.0, 2H), 3.91 (s, 3H), 3.63 (s, 3H), 2.10-2.19 (m, 1H), 1.70-1.88 (m, 3H), 1.50-1.60 (m, 3H), 1.40-1.48 (m, 2H), 1.10-1.22 (m, 2H).

EXAMPLE 7

3-Cyclopentyl-N-(5-methoxy-thiazolo[5,4-b]pyridin-2-yl)-2-(4-phenylsulfamoyl-phenyl)-propionamide

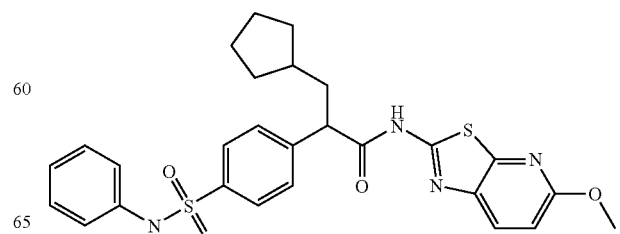

The title compound is prepared analogously to Example 1: MS e/z (ES) 535 (M−1⁻, 100%); m.p. 223-226° C.; ¹H NMR (CDCl₃) δ 12.65 (s, 1H), 10.30 (s, 1H), 8.02 (d, J=8.8, 1H), 7.75 (d, J=8.4, 2H), 7.56 (d, J=8.4, 2H), 7.15-7.24 (m, 2H), 7.05-7.09 (m, 2H), 6.95-7.04 (m, 1H), 6.90 (d, J=8.8, 1H), 4.06 (t, J=7.6, 1H), 3.90 (s, 3H), 2.07-2.15 (m, 1H), 1.65-1.76 (m, 3H), 1.50-1.58 (m, 3H), 1.40-1.48 (m, 2H), 1.10-122 (m, 2H).

EXAMPLE 8

2-[4-(2-Carbamoyl-ethylsulfamoyl)-phenyl]-3-cyclopentyl-N-(5-methoxy-thiazolo[5,4-b]pyridin-2-yl)-propionamide

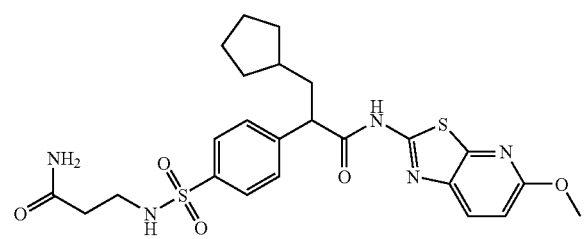

The title compound is prepared analogously to Example 1: MS e/z (ES) 532.1 (M+1⁺, 100%); ¹H NMR (CDCl₃) δ 12.69 (s, 1H), 8.03 (d, J=8.8, 1H), 7.78 (d, J=8.4, 2H), 7.62 (d, J=8.0, 2H), 7.23 (s, 2H), 6.89 (d, J=8.8, 1H), 6.82 (s, 1H), 4.07 (t, J=7.6, 1H), 3.91 (s, 3H), 2.85-2.94 (m, 2H), 2.21 (t, J=7.2, 2H), 2.23-2.29 (m, 1H), 2.14-2.20 (m, 1H), 1.68-1.85 (m, 2H), 1.55-1.64 (m, 3H), 1.42-1.48 (m, 2H), 1.11-1.18 (m, 2H).

EXAMPLE 9

3-Cyclopentyl-2-(4-diisopropylsulfamoyl-phenyl)-N-(5-methoxy-thiazolo[5,4-b]pyridin-2-yl)-propionamide

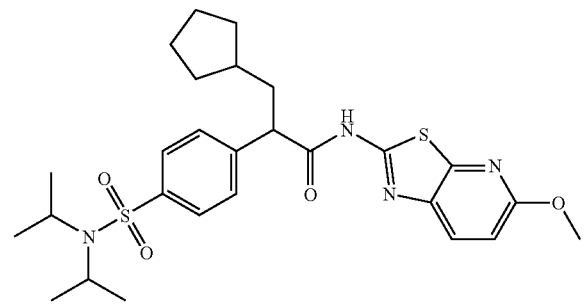

The title compound is prepared analogously to Example 1: MS e/z (ES) 545.5 (M+1⁺, 100%); m.p. 83-85° C.; ¹H NMR (CDCl₃) δ 12.68 (s, 1H), 8.02 (d, J=8.8, 1H), 7.81 (d, J=8.4, 2H), 7.59 (d, J=8.4, 2H), 6.90 (d, J=8.8, 1H), 4.05 (t, J=7.6, 1H), 3.90 (s, 3H), 3.69 (m, 2H), 2.11-2.17 (m, 1H), 1.76-1.80 (m, 1H), 1.68-1.70 (m, 2H), 1.55-1.61 (m, 3H), 1.40-1.44 (m, 2H), 1.22-1.24 (m, 1H), 1.15 (d, J=6.8, 12H), 0.83-0.85 (m, 1H).

EXAMPLE 10

3-Cyclopentyl-2-{4-[(furan-2-ylmethyl)-sulfamoyl]-phenyl}-N-(5-methoxy-thiazolo[5,4-b]pyridin-2-yl)-propionamide

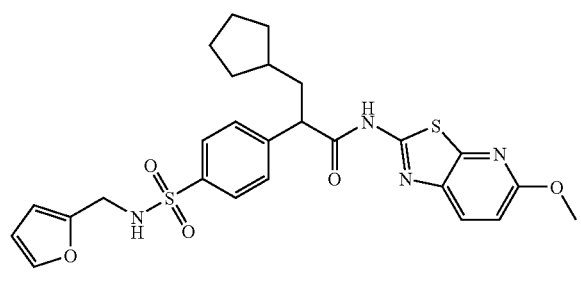

The title compound is prepared analogously to Example 1: MS e/z (ES) 541 (M+1⁺, 100%); m.p. 244-247° C.; ¹H NMR (CDCl₃) δ 12.66 (s, 1H), 8.15 (m, 1H), 8.03 (d, J=8.8, 1H), 7.73 (d, J=8.0, 2H), 7.56 (d, J=8.0, 2H), 7.37 (s, 1H), 6.92 (d, J=8.8, 1H), 6.16 (s, 1H), 6.08 (s, 1H), 4.00 (m, 3H), 3.90 (s, 3H), 2.11-2.14 (m, 1H), 1.70-1.83 (m, 3H), 1.50-1.60 (m, 2H), 1.40-1.45 (m, 2H), 1.10-1.16 (m, 3H).

EXAMPLE 11

3-Cyclopentyl-N-(5-methoxy-thiazolo[5,4-b]pyridin-2-yl)-2-[4-(phenyl-propyl-sulfamoyl)-phenyl]-propionamide

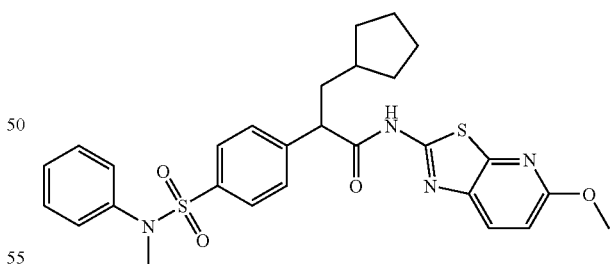

The title compound is prepared analogously to Example 1: MS e/z (ES) 579 (M+1⁺, 100%); m.p. 83-85° C.; ¹H NMR (CDCl₃) δ 12.69 (s, 1H), 8.03 (d, J=8.8, 1H), 7.55-7.61 (m, 4H), 7.28-7.35 (m, 2H), 7.03-7.05 (m, 2H), 6.91 (d, J=8.8, 1H), 4.07 (t, J=7.2, 1H), 3.91 (s, 3H), 3.48-3.52 (t, J=6.8, 2H), 2.12-2.19 (m, 1H), 1.69-1.82 (m, 3H), 1.56-1.61 (m, 3H), 1.43-1.46 (m, 2H), 1.27-1.33 (m, 3H), 1.12-1.14 (m, 2H), 0.79-0.83 (t, J=7.2, 3H).

EXAMPLE 12

3-Cyclopentyl-2-(4-dimethylsulfamoyl-phenyl)-N-(5-methoxy-thiazolo[5,4-b]pyridin-2-yl)-propionamide

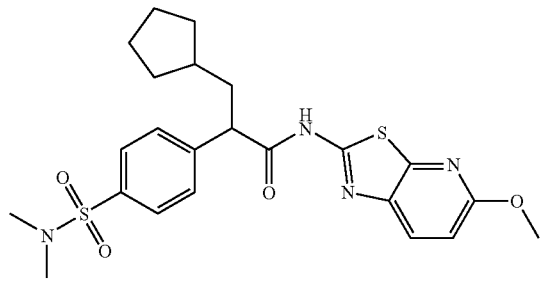

The title compound is prepared analogously to Example 1: MS e/z (ES) 487 (M−1−, 100%); m.p. 229-234° C.; $^1$H NMR (CDCl$_3$) δ 12.70 (s, 1H), 8.03 (d, J=8.8, 1H), 7.75 (d, J=8.4, 2H), 7.67 (d, J=8.4, 2H), 6.91 (d, J=8.8, 1H), 4.09 (t, J=7.6, 1H), 3.91 (s, 3H), 2.60 (s, 6H), 2.14-2.21 (m, 1H), 1.68-1.83 (m, 3H), 1.50-1.65 (m, 3H), 1.40-1.48 (m, 2H), 1.08-1.18 (m, 2H).

EXAMPLE 13

3-Cyclopentyl-2-(4-diethylsulfamoyl-phenyl)-N-(5-methoxy-thiazolo[5,4-b]pyridin-2-yl)-propionamide

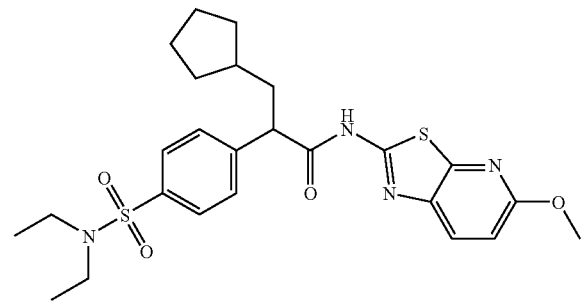

The title compound is prepared analogously to Example 1: MS e/z (ES) 515 (M−1−, 100%); m.p. 150-152° C.; $^1$H NMR (CDCl$_3$) δ 12.69 (s, 1H), 8.03 (d, J=8.8, 1H), 7.78 (d, J=8.0, 2H), 7.61 (d, J=8.0, 2H), 6.91 (d, J=8.8, 1H), 4.06 (t, J=7.6, 1H), 3.90 (s, 3H), 3.12 (q, J=7.2, 4H), 2.10-2.21 (m, 1H), 1.68-1.90 (m, 3H), 1.50-1.65 (m, 3H), 1.40-1.48 (m, 2H), 1.08-1.20 (m, 2H), 1.00-1.06 (m, 6H),

EXAMPLE 14

3-Cyclopentyl-2-(4-dipropylsulfamoyl-phenyl)-N-(5-methoxy-thiazolo[5,4-b]pyridin-2-yl)-propionamide

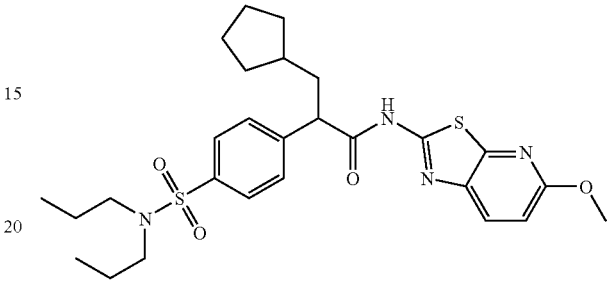

The title compound is prepared analogously to Example 1: MS e/z (ES) 545 (M+1+, 100%); m.p. 64-66° C.; $^1$H NMR (CDCl$_3$) δ 12.67 (s, 1H), 8.03 (d, J=8.8, 1H), 7.79 (d, J=8.4, 2H), 7.62 (d, J=8.4, 2H), 6.90 (d, J=8.8, 1H), 4.07 (t, J=7.2, 1H), 3.90 (s, 3H), 2.99 (t, J=7.2, 4H), 2.10-2.20 (m, 1H), 1.68-1.84 (m, 3H), 1.54-1.62 (m, 3H), 1.35-1.51 (m, 6H), 1.08-1.16 (m, 2H), 0.74-0.81 (m, 6H).

EXAMPLE 15

3-Cyclopentyl-N-(5-methoxy-thiazolo[5,4-b]pyridin-2-yl)-2-{4-[(pyridin-3-ylmethyl)-sulfamoyl]-phenyl}-propionamide The title compound is prepared analogously to Example 1: MS e/z (ES) 550 (M−1−, 100%); m.p. 227-229° C.; $^1$H NMR (CDCl$_3$) δ 12.67 (s, 1H), 8.38 (s, 1H), 8.25-8.32 (m, 2H), 8.04 (d, J=8.4, 1H), 7.74 (d, J=8.0, 2H), 7.51-7.58 (m, 3H), 7.12-7.21 (m, 1H), 6.91 (d, J=8.8, 1H), 4.02-4.06 (m, 3H), 3.91 (s, 3H), 2.10-2.18 (m, 1H), 1.70-1.83 (m, 3H), 1.60-1.80 (m, 3H), 1.40-1.50 (m, 2H), 1.10-1.22 (m, 2H).

EXAMPLE 16

2-(4-Cyclohexylsulfamoyl-phenyl)-3-cyclopentyl-N-(5-methoxy-thiazolo[5,4-b]pyridin-2-yl)-propionamide

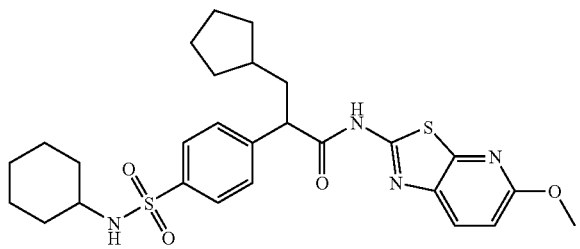

The title compound is prepared analogously to Example 1: MS e/z (ES) 541.6 (M−1⁻, 100%); m.p. 228-23° C.; $^1$H NMR (CDCl$_3$) δ 12.69 (s, 1H), 8.02 (d, J=8.8, 1H), 7.79 (d, J=8.4, 2H), 7.59 (m, 3H), 6.91 (d, J=8.8, 1H), 4.05 (t, J=6.8, 1H), 3.90 (s, 3H), 2.70-3.00 (m, 1H), 2.2-2.2 (m, 1H), 1.75-1.85 (m, 1H), 1.52-1.70 (m, 2H), 1.52-1.68 (m, 7H), 1.40-1.50 (m, 3H), 1.06-1.20 (m, 7H).

EXAMPLE 17

3-Cyclopentyl-N-(5-methoxy-thiazolo[5,4-b]pyridin-2-yl)-2-[4-(piperidine-1-sulfonyl)-phenyl]-propionamide

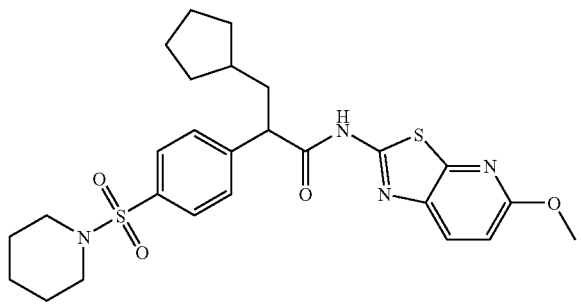

The title compound is prepared analogously to Example 1: MS e/z (ES) 527 (M−1⁻, 100%); m.p. 184-18° C.; $^1$H NMR (CDCl$_3$) δ 12.71 (s, 1H), 8.03 (d, J=8.8, 1H), 7.64-7.74 (m, 4H), 6.91 (d, J=8.8, 1H), 4.08 (t, J=7.2, 1H), 3.90 (s, 3H), 2.86 (m, 5H) 2.13-2.21 (m, 1H), 1.63-1.76 (m, 3H), 1.45-1.60 (m, 8H), 1.39-1.43 (m, 2H), 1.07-1.21 (m, 2H).

EXAMPLE 18

3-Cyclopentyl-N-(5-methoxy-thiazolo[5,4-b]pyridin-2-yl)-2-[4-(morpholine-4-sulfonyl)-phenyl]-propionamide

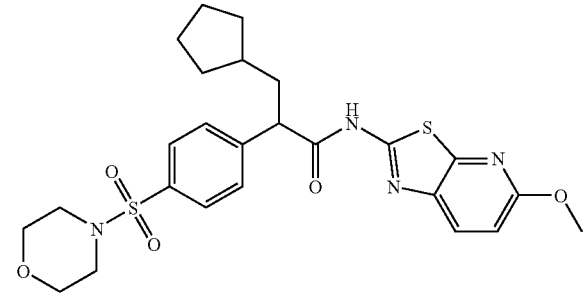

The title compound is prepared analogously to Example 1: MS e/z (ES) 529 (M−1⁻, 100%); m.p. 120-123° C.; $^1$H NMR (CDCl$_3$) δ 12.70 (s, 1H), 8.04 (d, J=8.4, 1H), 7.68-7.77 (m, 4H), 6.91 (d, J=8.8, 1H), 4.11 (t, J=6.8, 1H), 3.91 (s, 3H), 3.61 (m, 4H), 2.85 (m, 4H), 2.16-2.20 (m, 1H), 1.79-1.83 (m, 1H), 1.72-1.78 (m, 2H), 1.5-1.70 (m, 3H), 1.40-1.44 (m, 2H), 1.08-1.20 (m, 2H).

EXAMPLE 19

3-Cyclopentyl-N-(5-methoxy-thiazolo[5,4-b]pyridin-2-yl)-2-{4-[(thiophen-2-ylmethyl)-sulfamoyl]-phenyl}-propionamide

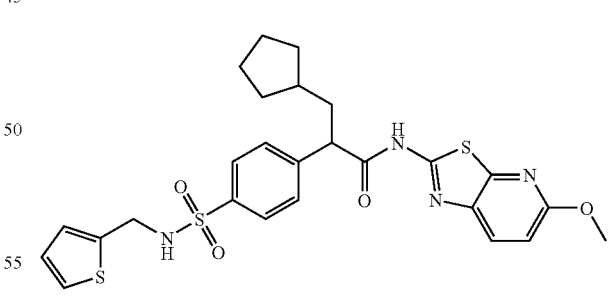

The title compound is prepared analogously to Example 1: MS e/z (ES) 555 (M−1⁻, 100%); m.p. 263-268° C.; $^1$H NMR (CDCl$_3$) δ 8.18 (s, 1H), 7.70 (d, J=8.0 2H), 7.55-7.61 (m, 3H), 7.34 (d, J=3.6, 1H), 6.87 (m, 2H), 6.61 (d, J=8.4, 1H), 4.14 (s, 2H), 3.83 (s, 3H), 3.68 (t, 1H), 2.04-2.11 (m, 1H), 1.68-1.74 (m, 3H), 1.50-1.65 (m, 3H), 1.37-1.45 (m, 2H), 1.10-1.20 (m, 2H).

EXAMPLE 20

3-Cyclopentyl-N-(5-methoxy-thiazolo[5,4-b]pyridin-2-yl)-2-[4-(pyridin-3-ylsulfamoyl)-phenyl]-propionamide

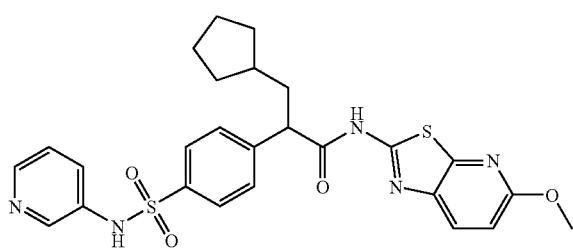

The title compound is prepared analogously to Example 1: MS e/z (ES) 536 (M−1⁻, 100%); m.p. 125-127° C.; ¹H NMR (CDCl₃), δ 12.66 (s, 1H), 10.58 (s, 1H), 8.20-8.28 (m, 2H), 8.02 (d, J=8.8, 1H), 7.77 (d, J=8.0, 2H), 7.58 (d, J=8.0, 2H), 7.46-7.51 (m, 1H), 7.21-7.30 (m, 1H), 6.90 (d, J=8.8, 1H), 4.01 (m, 1H), 3.90 (s, 3H), 2.08-2.18 (m, 1H), 1.60-1.80 (m, 3H), 1.50-1.68 (m, 3H), 1.40-1.48 (m, 2H), 1.10-1.22 (m, 2H).

EXAMPLE 21

3-Cyclopentyl-2-[4-(2-fluoro-benzylsulfamoyl)-phenyl]-N-(5-methoxy-thiazolo[5,4-b]pyridin-2-yl)-propionamide

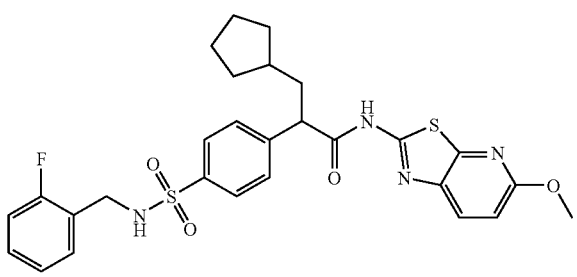

The title compound is prepared analogously to Example 1: MS e/z (ES) 567 (M−1⁻, 100%); m.p. 238-240° C.; ¹H NMR (CDCl₃) δ 12.67 (s, 1H), 8.19 (t, J=5.6, 1H), 8.02 (d, J=8.8, 1H), 7.73 (d, J=8.0, 2H), 7.54 (d, J=8.0, 2H), 7.24 (t, J=6.4, 1H), 7.00-7.18 (m, 1H), 6.96-7.09 (m, 1H), 6.91 (d, J=8.8, 1H), 4.04 (m, 3H) 3.91 (s, 3H), 2.08-2.18 (m, 1H), 1.60-1.90 (m, 3H), 1.50-1.68 (m, 3H), 1.40-1.48 (m, 2H), 1.10-1.22 (m, 2H).

EXAMPLE 22

3-Cyclopentyl-2-[4-(4-methoxy-benzylsulfamoyl)-phenyl]-N-(5-methoxy-thiazolo[5,4-b]pyridin-2-yl)-propionamide

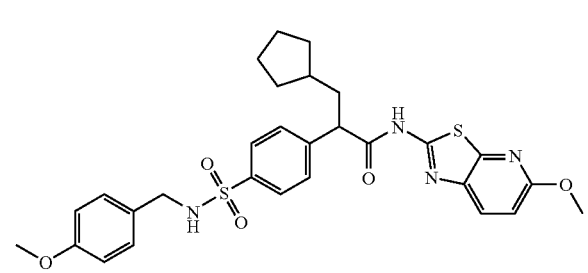

The title compound is prepared analogously to Example 1: MS m/z (ES) 565 (M−1⁻, 100%); m.p. 170-172° C.; ¹H NMR (CDCl₃) δ 12.64 (s, 1H), 9.91 (s, 1H), 8.02 (d, J=8.8, 1H), 7.67 (d, J=8.0, 2H), 7.54 (d, J=8.4, 2H), 6.91 (d, J=8.8, 2H), 6.63-6.78 (m, 3H), 3.95-4.04 (m, 1H), 3.91 (s, 3H), 3.63 (s, 3H), 2.10-2.18 (m, 1H), 1.70-1.83 (m, 3H), 1.60-1.80 (m, 3H), 1.40-1.50 (m, 2H), 1.10-1.22 (m, 2H).

EXAMPLE 23

2-(4-Benzylsulfamoyl-phenyl)-3-cyclopentyl-N-(5-methoxy-thiazolo[5,4-b]pyridin-2-yl)-propionamide

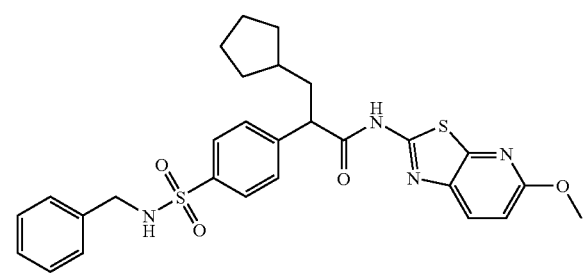

The title compound is prepared analogously to Example 1: MS e/z (ES) 549 (M−1⁻, 100%); m.p. 237-240° C.; ¹H NMR (CDCl₃) δ 12.68 (s, 1H), 8.16 (t, J=6.4, 1H), 8.02 (d, J=8.8, 1H), 7.74 (d, J=8.4, 2H), 7.56 (d, J=8.4, 2H), 7.01-7.30 (t, 5H), 6.91 (d, J=8.8, 1H), 3.92-4.10 (m, 3H), 3.91 (s, 3H), 2.08-2.18 (m, 1H), 1.60-1.90 (m, 3H), 1.50-1.68 (m, 3H), 1.40-1.48 (m, 2H), 1.10-1.22 (m, 2H).

EXAMPLE 24

2-[4-(Benzyl-methyl-sulfamoyl)-phenyl]-3-cyclopentyl-N-(5-methoxy-thiazolo[5,4-b]pyridin-2-yl)-propionamide

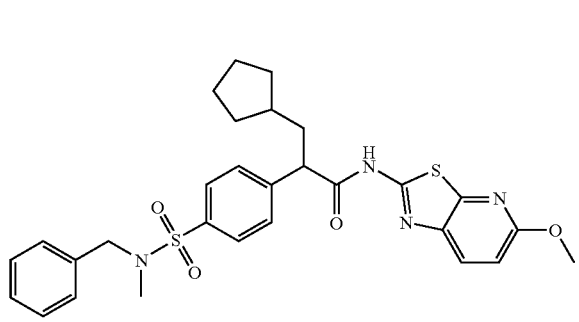

The title compound is prepared analogously to Example 1: MS e/z (ES) 565 (M+1$^+$, 100%); m.p. 206-208° C.; $^1$H NMR (CDCl$_3$) δ 12.73 (s, 1H), 8.04 (d, J=8.8, 1H), 7.85 (d, J=8.0, 2H), 7.67 (d, J=8.0, 2H), 7.26-7.32 (m, 5H), 6.91 (d, J=8.8, 1H), 4.08-4.13 (m, 3H), 3.90 (s, 3H), 2.54 (s, 3H), 2.14-2.21 (m, 1H), 1.71-1.82 (m, 3H), 1.50-1.65 (m, 3H), 1.40-1.49 (m, 2H), 1.10-1.25 (m, 2H).

EXAMPLE 25

3-Cyclopentyl-2-(4-dibutylsulfamoyl-phenyl)-N-(5-methoxy-thiazolo[5,4-b]pyridin-2-yl)-propionamide

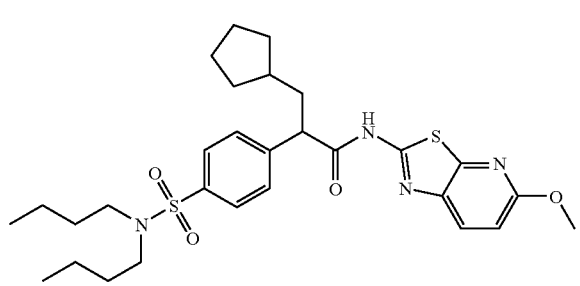

The title compound is prepared analogously to Example 1: MS e/z (ES) 573.4 (M+1$^+$, 100%); m.p. 65-67° C.; $^1$H NMR (CDCl$_3$) δ 12.66 (s, 1H), 8.02 (d, J=8.8, 1H), 7.78 (d, J=8.4, 2H), 7.62 (d, J=8.4, 2H), 6.90 (d, J=8.8, 1H), 4.06 (t, J=7.6, 1H), 3.90 (s, 3H), 3.04 (t, J=7.6, 4H), 2.10-2.15 (m, 1H), 1.79-1.85 (m, 1H), 1.65-1.76 (m, 2H), 1.55-1.60 (m, 3H), 1.32-1.44 (m, 6H), 1.13-1.30 (m, 6H), 0.78-0.82 (m, 6H).

EXAMPLE 26

3-Cyclopentyl-2-[4-(4-ethyl-piperazine-1-sulfonyl)-phenyl]-N-(5-methoxy-thiazolo[5,4-b]pyridin-2-yl)-propionamide

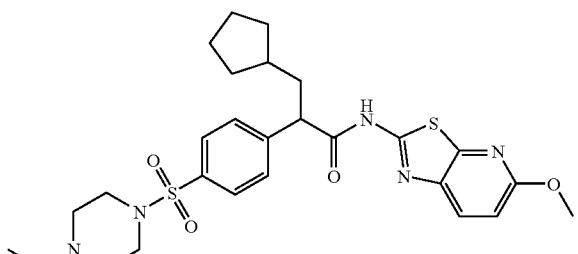

The title compound is prepared analogously to Example 1: MS e/z (ES) 556 (M−1$^-$, 100%); m.p. 106-10° C.; $^1$H NMR (CDCl$_3$) δ 12.71 (s, 1H), 8.03 (d, J=8.8, 1H), 7.66-7.75 (m, 4H), 6.91 (d, J=8.4, 1H), 4.09 (t, J=7.6, 1H), 3.91 (s, 3H), 2.85-2.88 (m, 4H), 2.34-2.38 (m, 4H), 2.23-2.29 (m, 2H), 2.14-2.21 (m, 1H), 1.70-1.83 (m, 3H), 1.55-1.61 (m, 3H), 1.42-1.45 (m, 2H), 1.11-1.18 (m, 2H), 0.86-0.91 (m, 3H).

EXAMPLE 27

2-[4-(4-Acetyl-piperazine-1-sulfonyl)-phenyl]-3-cyclopentyl-N-(5-methoxy-thiazolo[5,4-b]pyridin-2-yl)-propionamide

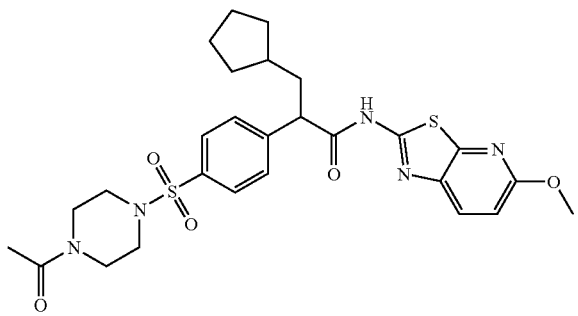

The title compound is prepared analogously to Example 1: MS e/z (ES) 572 (M+1$^+$, 100%); m.p. 215-217° C.; $^1$H NMR (CDCl$_3$) δ 12.72 (s, 1H), 8.03 (d, J=8.8, 1H), 7.66-7.76 (m, 4H), 6.91 (d, J=8.4, 1H), 4.09 (m, 1H), 3.90 (s, 3H), 3.47-3.50 (m, 4H), 2.84-2.91 (m, 4H), 2.14-2.20 (m, 1H), 1.91 (s, 3H), 1.70-1.81 (m, 2H), 1.50-1.59 (m, 3H), 1.40-1.49 (m, 2H), 1.08-1.14 (m, 3H).

The following compounds may also be prepared according to Method A.

EXAMPLE 28

| Example | Chemical Name | MS; M + 1+ |
|---|---|---|
| 28-1 | 3-Cyclopentyl-N-(5-methoxy-thiazolo[5,4-b]pyridin-2-yl)-2-[4-(piperazine-1-sulfonyl)-phenyl]-propionamide hydrochloride | 530.68 |
| 28-2 | 3-Cyclopentyl-N-(5-methoxy-thiazolo[5,4-b]pyridin-2-yl)-2-[4-(4-phenyl-piperazine-1-sulfonyl)-phenyl]-propionamide | 606.78 |
| 28-3 | 3-Cyclopentyl-2-{4-[4-(2-methoxy-phenyl)-piperazine-1-sulfonyl]-phenyl}-N-(5-methoxy-thiazolo[5,4-b]pyridin-2-yl)-propionamide | 636.81 |
| 28-4 | 2-{4-[4-(3-Chloro-phenyl)-piperazine-1-sulfonyl]-phenyl}-3-cyclopentyl-N-(5-methoxy-thiazolo[5,4-b]pyridin-2-yl)-propionamide | 641.23 |

-continued

| Example | Structure | Chemical Name | MS; M + 1+ |
|---|---|---|---|
| 28-5 | 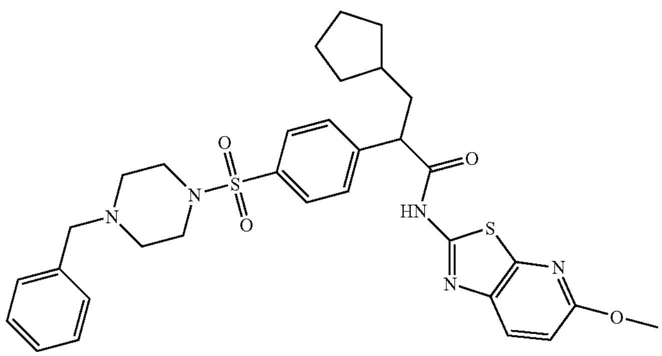 | 2-[4-(4-Benzyl-piperazine-1-sulfonyl)-phenyl]-3-cyclopentyl-N-(5-methoxy-thiazolo[5,4-b]pyridin-2-yl)-propionamide | 620.81 |
| 28-6 | 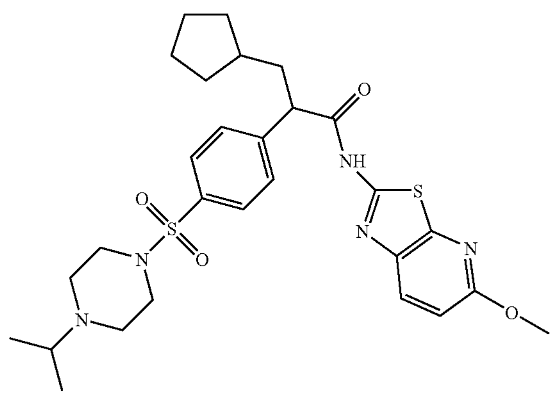 | 3-Cyclopentyl-2-[4-(4-isopropyl-piperazine-1-sulfonyl)-phenyl]-N-(5-methoxy-thiazolo[5,4-b]pyridin-2-yl)-propionamide | 572.77 |
| 28-7 | 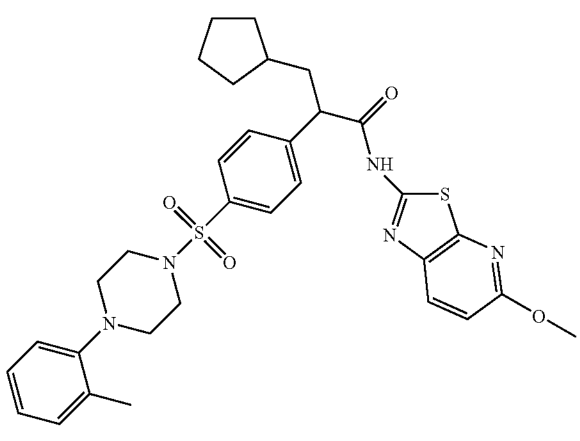 | 3-Cyclopentyl-N-(5-methoxy-thiazolo[5,4-b]pyridin-2-yl)-2-[4-(4-o-tolyl-piperazine-1-sulfonyl)-phenyl]-propionamide | 620.81 |

-continued

| Example | Structure | Chemical Name | MS; M + 1+ |
|---|---|---|---|
| 28-8 | 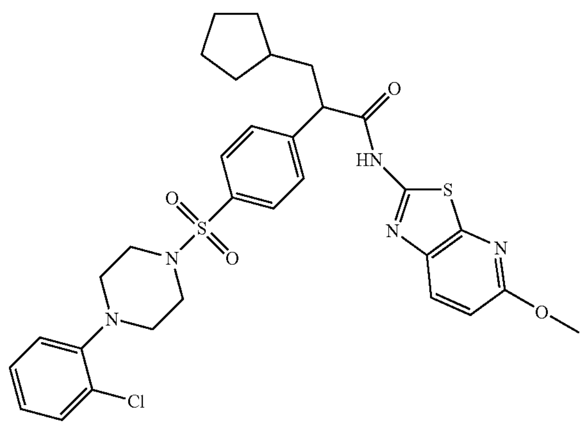 | N-[2-(2-{4-[4-(2-Chloro-phenyl)-piperazine-1-sulfonyl]-phenyl}-3-cyclopentyl-propionylamino)-thiazol-5-yl]-acetimidic acid methyl ester | 641.23 |
| 28-9 | 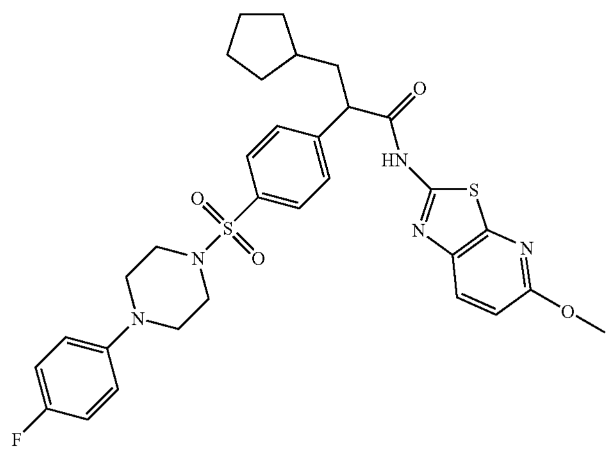 | 3-Cyclopentyl-2-{4-[4-(4-fluoro-phenyl)-piperazine-1-sulfonyl]-phenyl}-N-(5-methoxy-thiazolo[5,4-b]pyridin-2-yl)-propionamide | 624.77 |
| 28-10 | 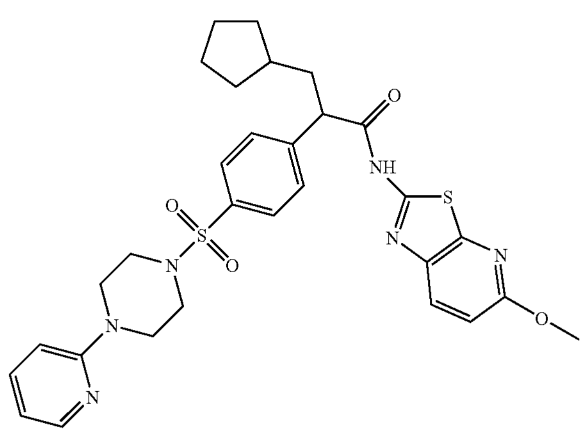 | 3-Cyclopentyl-N-(5-methoxy-thiazolo[5,4-b]pyridin-2-yl)-2-[4-(4-pyridin-2-yl-piperazine-1-sulfonyl)-phenyl]-propionamide | 607.77 |

-continued

| Example | Structure | Chemical Name | MS; M + 1+ |
|---|---|---|---|
| 28-11 | 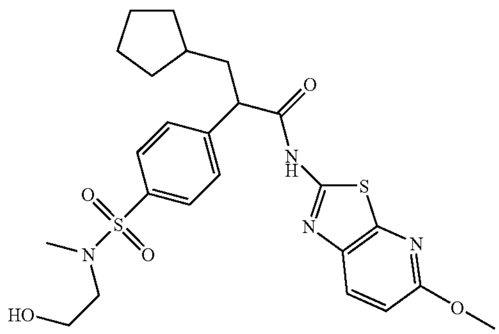 | 3-Cyclopentyl-2-{4-[(2-hydroxy-ethyl)-methyl-sulfamoyl]-phenyl}-N-(5-methoxy-thiazolo[5,4-b]pyridin-2-yl)-propionamide | 519.66 |
| 28-12 | 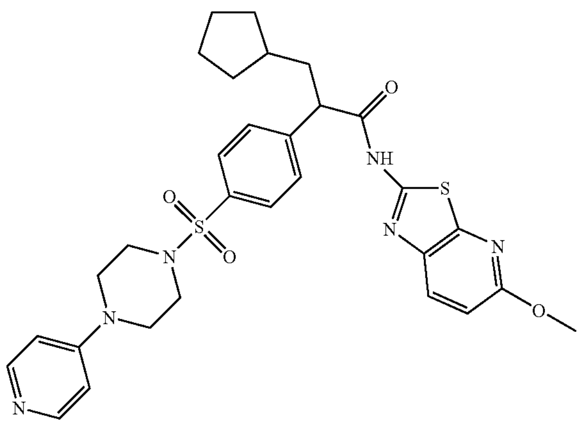 | 3-Cyclopentyl-N-(5-methoxy-thiazolo[5,4-b]pyridin-2-yl)-2-[4-(4-pyridin-4-yl-piperazine-1-sulfonyl)-phenyl]-propionamide | 607.77 |
| 28-13 | 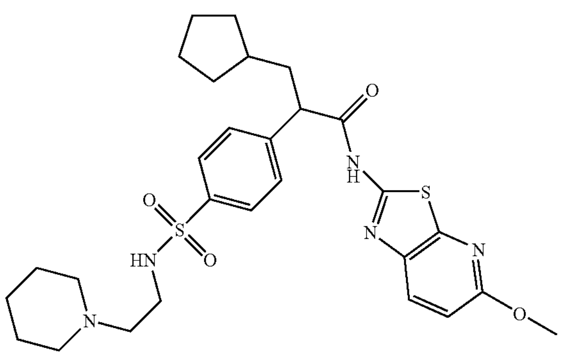 | 3-Cyclopentyl-N-(5-methoxy-thiazolo[5,4-b]pyridin-2-yl)-2-[4-(2-piperidin-1-yl-ethylsulfamoyl)-phenyl]-propionamide | 572.77 |
| 28-14 | 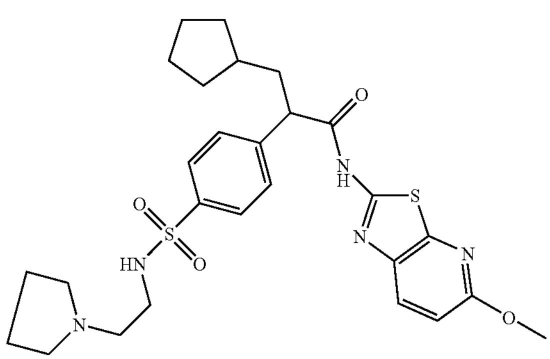 | 3-Cyclopentyl-N-(5-methoxy-thiazolo[5,4-b]pyridin-2-yl)-2-[4-(2-pyrrolidin-1-yl-ethylsulfamoyl)-phenyl]-propionamide | 558.74 |

-continued

| Example | Structure | Chemical Name | MS; M + 1+ |
|---|---|---|---|
| 28-15 | 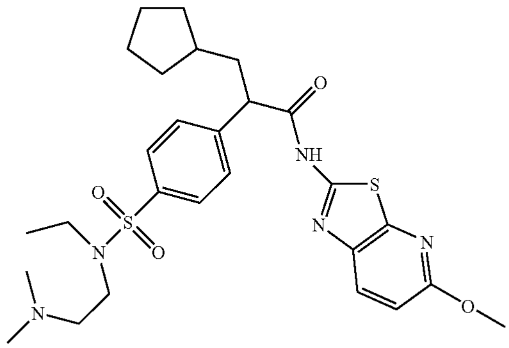 | 3-Cyclopentyl-2-{4-[(2-dimethylamino-ethyl)-ethyl-sulfamoyl]-phenyl}-N-(5-methoxy-thiazolo[5,4-b]pyridin-2-yl)-propionamide hydrochloride | 560.76 |
| 28-16 | 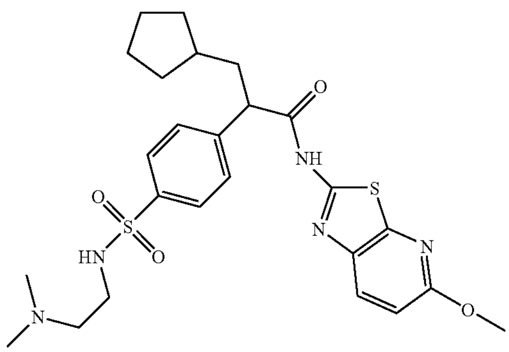 | 3-Cyclopentyl-2-[4-(2-dimethylamino-ethylsulfamoyl)-phenyl]-N-(5-methoxy-thiazolo[5,4-b]pyridin-2-yl)-propionamide hydrochloride | 532.7 |
| 28-17 | 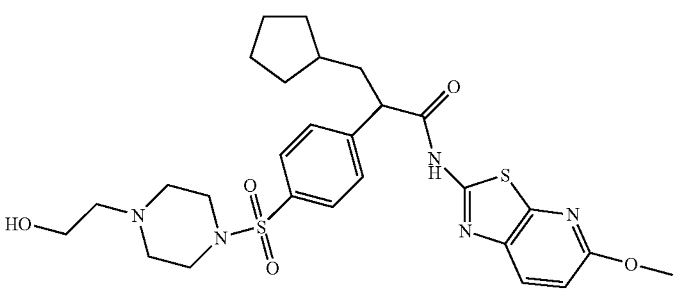 | 3-Cyclopentyl-2-{4-[4-(2-hydroxy-ethyl)-piperazine-1-sulfonyl]-phenyl}-N-(5-methoxy-thiazolo[5,4-b]pyridin-2-yl)-propionamide | 574.74 |
| 28-18 | 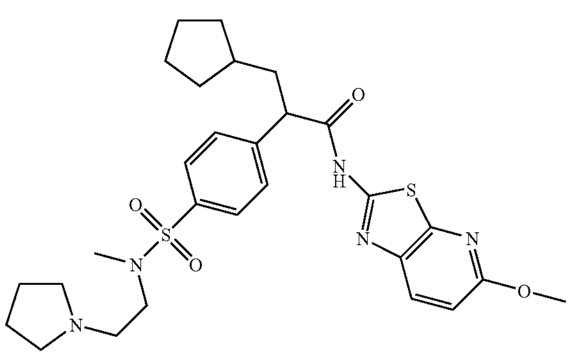 | 3-Cyclopentyl-N-(5-methoxy-thiazolo[5,4-b]pyridin-2-yl)-2-{4-[methyl-(2-pyrrolidin-1-yl-ethyl)-sulfamoyl]-phenyl}-propionamide hydrochloride | 572.77 |

-continued

| Example | Structure | Chemical Name | MS; M + 1+ |
|---|---|---|---|
| 28-19 | 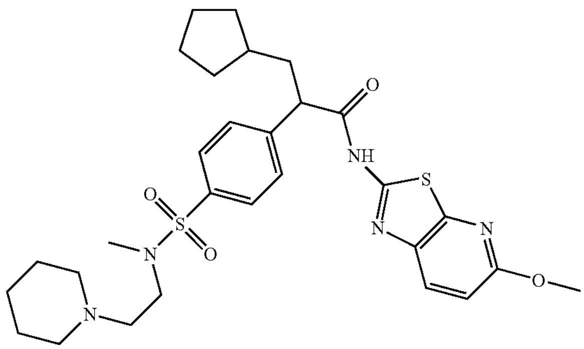 | 3-Cyclopentyl-N-(5-methoxy-thiazolo[5,4-b]pyridin-2-yl)-2-{4-[methyl-(2-piperidin-1-yl-ethyl)-sulfamoyl]-phenyl}-propionamide hydrochloride | 586.79 |
| 28-20 | 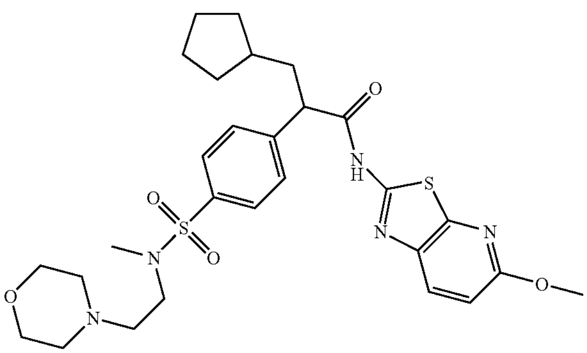 | 3-Cyclopentyl-N-(5-methoxy-thiazolo[5,4-b]pyridin-2-yl)-2-{4-[methyl-(2-morpholin-4-yl-ethyl)-sulfamoyl]-phenyl}-propionamide | 588.77 |
| 28-21 | 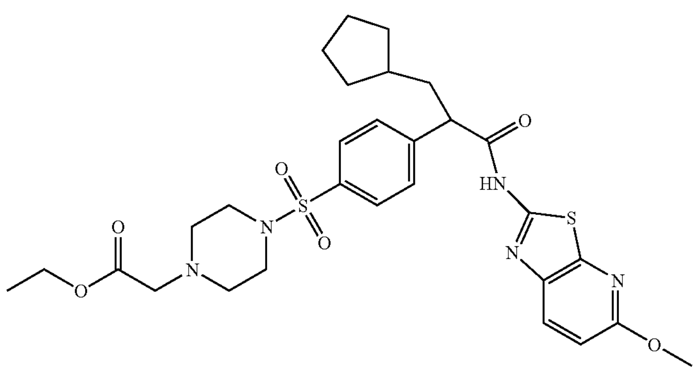 | 4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid ethyl ester | 616.78 |
| 28-22 | 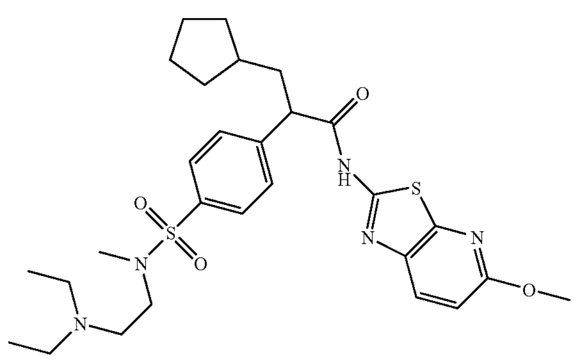 | 3-Cyclopentyl-2-{4-[(2-diethylamino-ethyl)-methyl-sulfamoyl]-phenyl}-N-(5-methoxy-thiazolo[5,4-b]pyridin-2-yl)-propionamide | 574.78 |

-continued

| Example | Structure | Chemical Name | MS; M + 1+ |
|---|---|---|---|
| 28-23 | 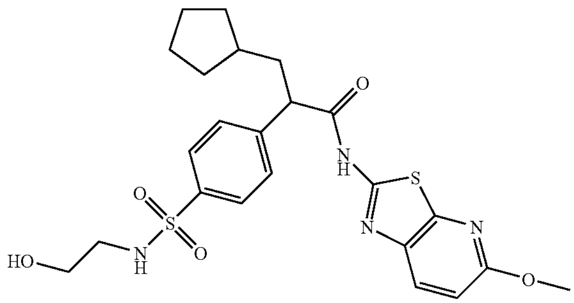 | 3-Cyclopentyl-2-[4-(2-hydroxy-ethylsulfamoyl)-phenyl]-N-(5-methoxy-thiazolo[5,4-b]pyridin-2-yl)-propionamide | 505.63 |
| 28-24 | 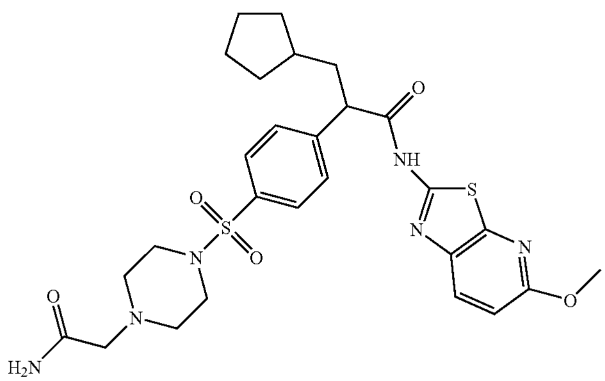 | 2-[4-(4-Carbamoylmethyl-piperazine-1-sulfonyl)-phenyl]-3-cyclopentyl-N-(5-methoxy-thiazolo[5,4-b]pyridin-2-yl)-propionamide | 587.74 |
| 28-25 | 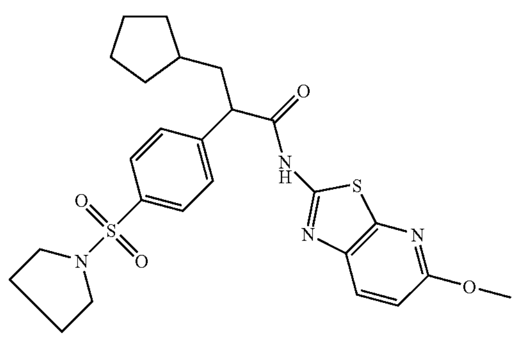 | 3-Cyclopentyl-N-(5-methoxy-thiazolo[5,4-b]pyridin-2-yl)-2-[4-(pyrrolidine-1-sulfonyl)-phenyl]-propionamide | 515.67 |
| 28-26 | 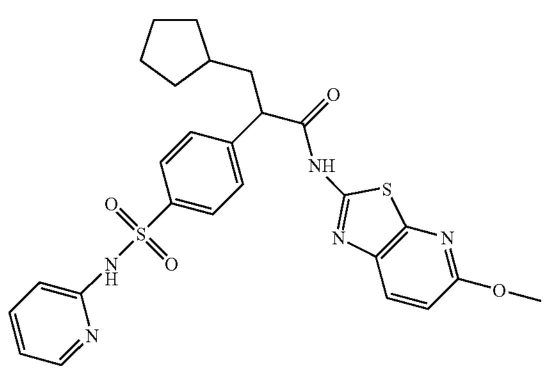 | 3-Cyclopentyl-N-(5-methoxy-thiazolo[5,4-b]pyridin-2-yl)-2-[4-(pyridin-2-ylsulfamoyl)-phenyl]-propionamide | 538.66 |

The following compounds may be prepared according to Method B:

EXAMPLE 29

4-[2-cyclopentyl-1-(5-methoxy-thiazolo[5,4-b]pyridin-2-ylcarbamoyl)-ethyl]-benzenesulfonamide of the formula

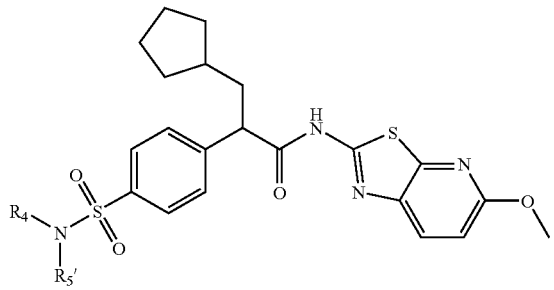

A. 3-Cyclopentyl-2-(4-nitro-phenyl)-propionic acid ethyl ester

To a 1 L round bottom flask containing 250 mL of 9:1 THF/DMPU at −78C is added under nitrogen 11 mL (78.6 mmol) anhydrous DIEA followed by rapid addition of 32 mL of 2.5M n-BuLi in hexanes. After 10 min at −78° C. a solution of 15.4 g (74 mmol) of p-nitro-phenylacetic acid, ethyl ester in 100 mL of 9:1 THF/DMPU is added dropwise over 30 min. A deep purple solution results, and the reaction mixture is stirred at −78° C. for 30 min and then cyclopentyl methyl iodide (17.6 g, 78 mmol) in 50 mL of 9:1 THF/DMPU is added. The reaction is stirred while warming slowly to RT temperature overnight. The mixture is poured into 1 L of 1 N HCl (aq) and extracted twice with methyl-t-butylether (MTBE). The combined MTBE extracts are washed with brine, dried over anhydrous magnesium sulfate, filtered and reduced to an orange oil. Flash chromatography over silica eluting with 4:1 hexane/MTBE affords 3-cyclopentyl-2-(4-nitro-phenyl)-propionic acid ethyl ester as an orange oil: $^1$H NMR (400 MHz, CDCl$_3$) δ 1.0-1.1 (m, 2H), 1.2 (t, 3H, J=7.2), 1.4-1.8 (m, 5H), 1.8-1.9 (m, 2H), 2.1-2.25 (m, 2H), 3.74 (t, 1H, J=7.8), 4.1 (m, 2H), 7.51 (d, 2H, J=8.8), 8.19 (d, 2H, J=8.8).

B. 3-Cyclopentyl-2-(4-nitro-phenyl)-propionic acid

The title A compound, 3-cyclopentyl-2-(4-nitro-phenyl)-propionic acid ethyl ester (3.6 g, 12.3 mmol) is dissolved in 25 mL of methanol and aqueous NaOH (0.70 g, 17.5 mmol in 4 mL of water) is added and the mixture is stirred at RT overnight. The methanol is removed under reduced pressure and the residue is diluted with 100 mL of water and extracted with ether. The aqueous layer is then acidified with 1 N HCl (aq) and then extracted with ethyl acetate. The combined ethyl acetate layers are dried over anhydrous magnesium sulfate, filtered and reduced under vacuum to a crude orange oil. The crude oil is triturated with 100 mL of hexane/10-15 mL of ether to produce 3-cyclopentyl-2-(4-nitro-phenyl)-propionic acid as a solid: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.74 (t, 1H, J=7.8), 7.51 (d, 2H, J=8.8), 8.19 (d, 2H, J=8.8).

C. 3-Cyclopentyl-N-(5-methoxy-thiazolo[5,4-b]pyridin-2-yl)-2-(4-nitro-phenyl)-propionamide The title B compound, 3-cyclopentyl-2-(4-nitro-phenyl)-propionic acid (7.5 g, 28.5 mmol) is dissolved in 25 mL of thionyl chloride and a drop of DMF and the mixture stirred at RT for 5-6 h. The excess of thionyl chloride is removed under reduced pressure. The residue is then taken up in DCM and added dropwise to a solution of 5.2 g (28.5 mmol) of the aminothiazole in 25 mL pyridine. The reaction mixture is stirred for 5 h before being evaporated to remove the pyridine. The residue is partitioned between ethyl acetate and brine, extracted with ethyl acetate. The combined organic layers are washed with saturated sodium bicarbonate, brine, dried over anhydrous magnesium sulfate, filtered and then reduced to an orange-brown solid. This is then vacuum dried to afford 3-cyclopentyl-N-(5-methoxy-thiazolo[5,4-b]pyridin-2-yl)-2-(4-nitro-phenyl)-propionamide as a foam: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.6 (t, 1H, J=7.8), 4.01 (s, 3H), 6.8 (d, 1H, J=8.8), 7.4 (d, 2H, J=8.6), 7.8 (d, 1H, J=8.8 Hz), 8.19 (d, 2H, J=8.6 Hz), 9.3 (s, 1H).

D. 2-(4-Amino-phenyl)-3-cyclopentyl-N-(5-methoxy-thiazolo[5,4-b]pyridin-2-yl)-propionamide The title C compound, 3-cyclopentyl-N-(5-methoxy-thiazolo[5,4-b]pyridin-2-yl)-2-(4-nitro-phenyl)-propionamide (12 g, 28.2 mmol) is diluted with 160 mL of ethanol and 150 mL acetic acid. 8 g of iron powder (325 mesh, 0.14 mol) is added and the mixture heated to reflux. Once reflux begins the mixture is stirred vigorously and then heating is discontinued and the mixture is allowed to cool slowly. The solvents are removed and the residue is treated with 250 mL of water. Saturated sodium bicarbonate is added carefully to bring the mixture to a pH of 8-9. The mixture is extracted with ethyl acetate, washed with brine, dried and evaporated to give an orange solid which is triturated from hexane. The resulted solid is collected by filtration to afford 2-(4-amino-phenyl)-3-cyclopentyl-N-(5-methoxy-thiazolo[5,4-b]pyridin-2-yl)-propionamide: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.6 (t, 1H, J=7.8), 3.98 (s, 3H), 6.7 (d, 1H, J=8.8), 6.8 (d, 2H, J=8.6), 7.2 (d, 2H, J=8.6), 7.8 (d, 1H, J=8.8).

E. 4-[2-Cyclopentyl-1-(5-methoxy-thiazolo[5,4-b]pyridin-2-ylcarbamoyl)-ethyl]-benzenesulfonyl chloride The title D compound, 2-(4-amino-phenyl)-3-cyclopentyl-N-(5-methoxy-thiazolo[5,4-b]pyridin-2-yl)-propionamide (2.0 g, 5.1 mmol) is dissolved in 50 mL of acetic acid and 20 mL of concentrated HCl and the mixture is cooled to 0° C. A solution of 0.35 g (5.1 mmol) of NaNO$_2$ in 5 mL of water is added dropwise and the mixture is stirred for 30 min. The resulting yellow solution is then added to 180 mL of the Green Solution (prepared by bubbling 74 g of sulfur dioxide gas into 740 mL of glacial acetic acid followed by addition of 30 g of CuCl$_2$ in 35-40 mL water. The resulting mixture is filtered through filter paper to obtain a clear green solution) and the mixture is stirred at RT overnight (the initial black-green solution transforms to a light green solution after 24 h). The resulting mixture is poured onto 500 g of ice and the precipitated solids are collected by filtration, washed with water and then dissolved in ethyl acetate, washed with brine, dried over anhydrous magnesium sulfate, filtered and evaporated to afford a yellow foam. This material is flash chromatographed over silica eluting with 7:3 hexane/ethyl acetate to afford 4-[2-cyclopentyl-1-(5-methoxy-thiazolo[5,4-b]pyridin-2-ylcarbamoyl)-ethyl]-benzenesulfonyl chloride as a stable yellow foam: $^1$H NMR (400 MHz, CDCl$_3$) δ 1.0-1.1 (m, 2H), 1.4-1.8 (m, 5H), 1.8-1.9 (m, 2H), 2.1-2.25 (m, 2H), 3.7 (t, 1H, J=7.8), 4.01 (s, 3H), 6.8 (d, 1H, J=8.8), 7.5 (d, 2H, J=8.6), 7.8 (d, 1H, J=8.8), 8.19 (d, 2H, J=8.6), 9.3 (s, 1H).

G. Coupling of 4-[2-cyclopentyl-1-(5-methoxy-thiazolo[5,4-b]pyridin-2-ylcarbamoyl)-ethyl]-benzenesulfonyl chloride with an amine of formula R$_4$—NH—R$_5$'

The title E compound, 4-[2-cyclopentyl-1-(5-methoxy-thiazolo[5,4-b]pyridin-2-ylcarbamoyl)-ethyl]-benzenesulfonyl chloride may be reacted with the desired amine of formula R$_4$—NH—R$_5$' according to methods well know in the art, e.g., using reaction conditions as described in Example 1 for the preparation of the title C compound.

| Example | Structure | Chemical name | MS; M + 1$^+$ |
|---|---|---|---|
| 29-1 | 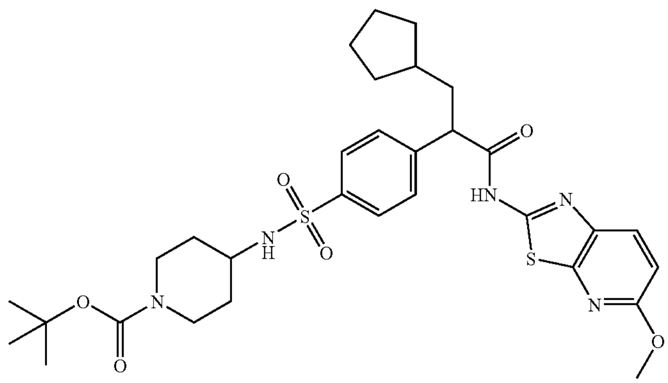 | 4-{4-[2-Cyclopentyl-1-(5-methoxy-thiazolo[5,4-b]pyridin-2-ylcarbamoyl)-ethyl]-benzenesulfonylamino)}-piperidine-1-carboxylic acid tert-butyl ester | 644.83 |
| 29-2 | 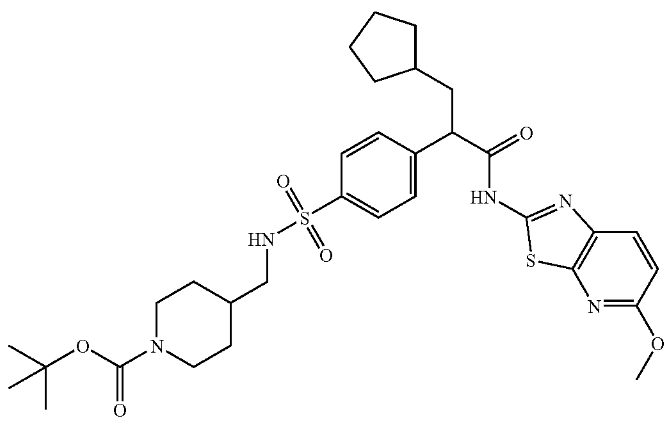 | 4-({4-[2-Cyclopentyl-1-(5-methoxy-thiazolo[5,4-b]pyridin-2-ylcarbamoyl)-ethyl]-benzenesulfonylamino}-methyl)-piperidine-1-carboxylic acid tert-butyl ester | 658.86 |
| 29-3 | 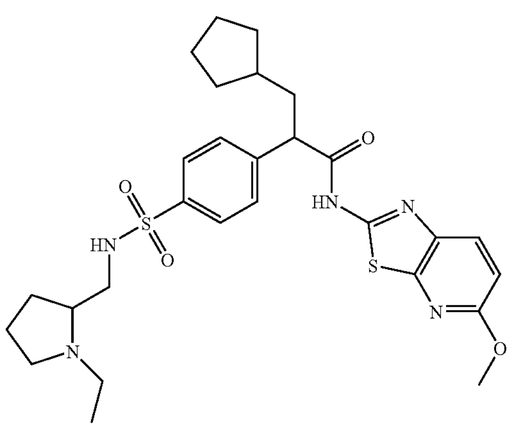 | 3-Cyclopentyl-2-{4-[(1-ethyl-pyrrolidin-2-ylmethyl)-sulfamoyl]-phenyl}-N-(5-methoxy-thiazolo[5,4-b]pyridin-2-yl)-propionamide | 572.77 |

| Example | Structure | Chemical name | MS; M + 1+ |
|---|---|---|---|
| 29-4 | 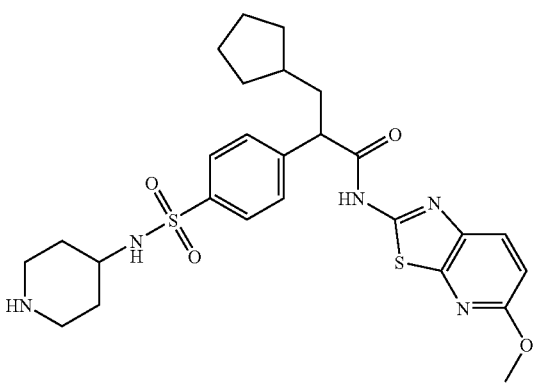 | 3-Cyclopentyl-N-(5-methoxy-thiazolo[5,4-b]pyridin-2-yl)-2-[4-(piperidin-4-ylsulfamoyl)-phenyl]-propionamide | 544.71 |
| 29-5 | 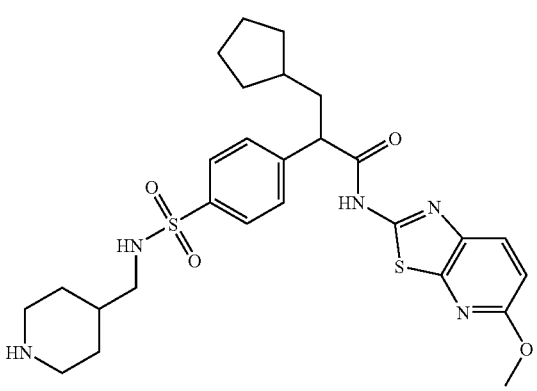 | 3-Cyclopentyl-N-(5-methoxy-thiazolo[5,4-b]pyridin-2-yl)-2-{4-[(piperidin-4-ylmethyl)-sulfamoyl]-phenyl}-propionamide | 558.74 |
| 29-6 | 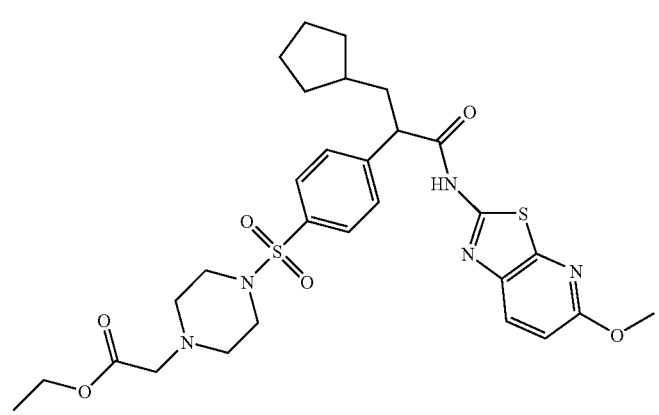 | (4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid ethyl ester | 616.78 |

-continued

| Example | Structure | Chemical name | MS; M + 1+ |
|---|---|---|---|
| 29-7 | 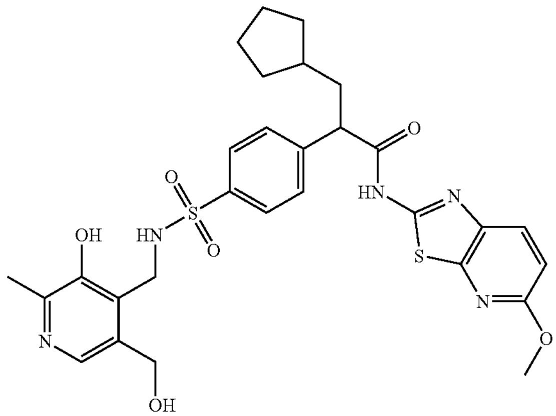 | 3-Cyclopentyl-2-{4-[(3-hydroxy-5-hydroxymethyl-2-methyl-pyridin-4-ylmethyl)-sulfamoyl]-phenyl}-N-(5-methoxy-thiazolo[5,4-b]pyridin-2-yl)-propionamide | 612.74 |
| 29-8 | 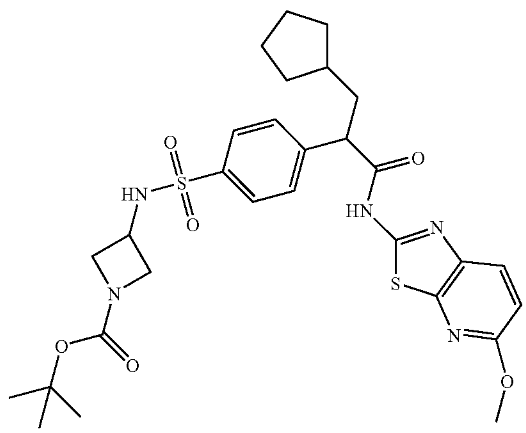 | 3-{4-[2-Cyclopentyl-1-(5-methoxy-thiazolo[5,4-b]pyridin-2-ylcarbamoyl)-ethyl]-benzenesulfonylamino}-azetidine-1-carboxylic acid tert-butyl ester | 616.78 |
| 29-9 | 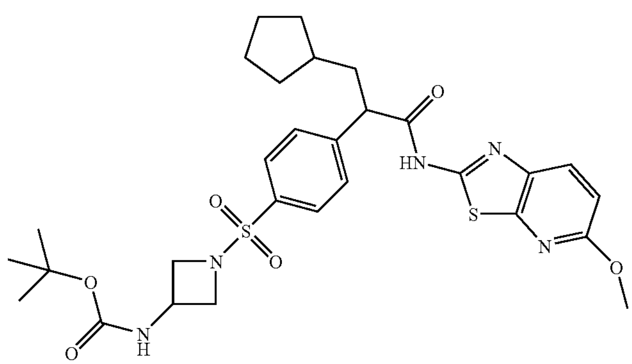 | (1-{4-[2-Cyclopentyl-1-(5-methoxy-thiazolo[5,4-b]pyridin-2-ylcarbamoyl)-ethyl]-benzenesulfonyl}-azetidin-3-yl)-carbamic acid tert-butyl ester | 616.78 |
| 29-10 | 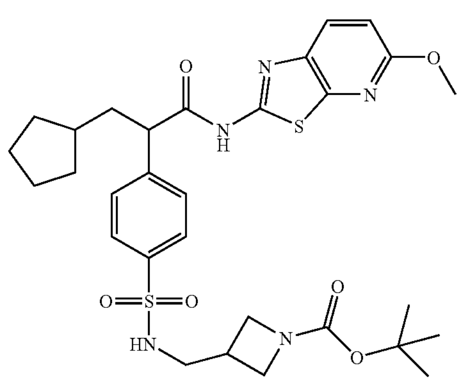 | 3-({4-[2-Cyclopentyl-1-(5-methoxy-thiazolo[5,4-b]pyridin-2-ylcarbamoyl)-ethyl]-benzenesulfonylamino}-methyl)-azetidine-1-carboxylic acid tert-butyl ester | 630.8 |

-continued

| Example | Structure | Chemical name | MS; M + 1+ |
|---|---|---|---|
| 29-11 | 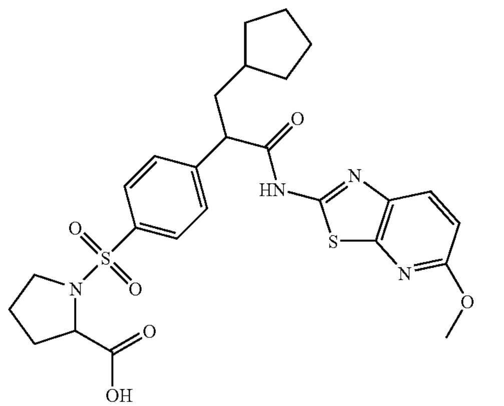 | 1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid | 559.68 |
| 29-12 | 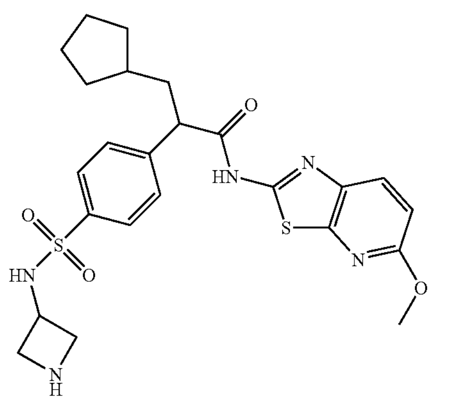 | 2-[4-(Azetidin-3-ylsulfamoyl)-phenyl]-3-cyclopentyl-N-(5-methoxy-thiazolo[5,4-b]pyridin-2-yl)-propionamide | 516.66 |
| 29-13 | 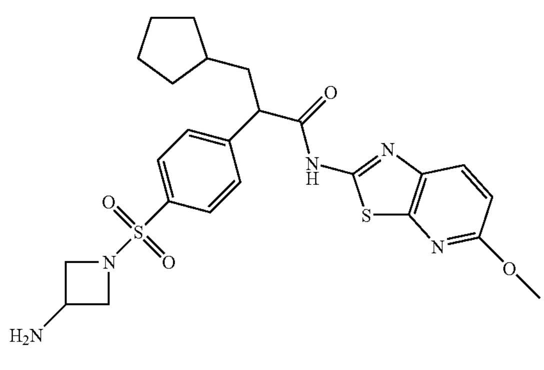 | 2-[4-(3-Amino-azetidine-1-sulfonyl)-phenyl]-3-cyclopentyl-N-(5-methoxy-thiazolo[5,4-b]pyridin-2-yl)-propionamide | 516.66 |
| 29-14 | 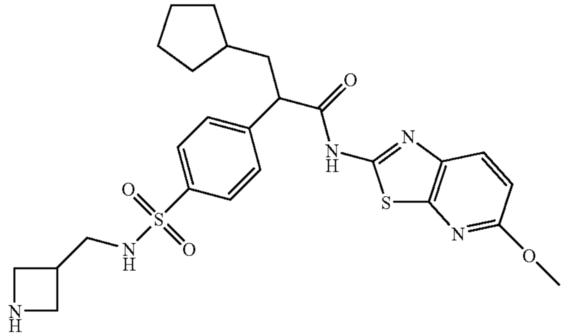 | 2-{4-[(Azetidin-3-ylmethyl)-sulfamoyl]-phenyl}-3-cyclopentyl-N-(5-methoxy-thiazolo[5,4-b]pyridin-2-yl)-propionamide | 530.68 |

| Example | Structure | Chemical name | MS; M + 1+ |
|---|---|---|---|
| 29-15 | 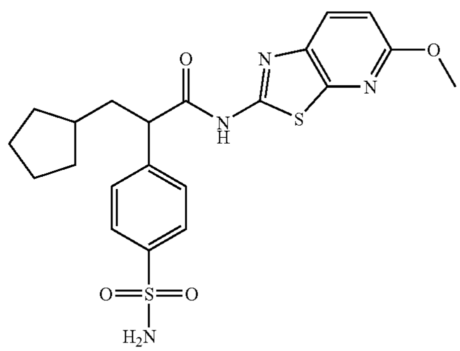 | 3-Cyclopentyl-N-(5-methoxy-thiazolo[5,4-b]pyridin-2-yl)-2-(4-sulfamoyl-phenyl)-propionamide | 461.58 |
| 29-16 | 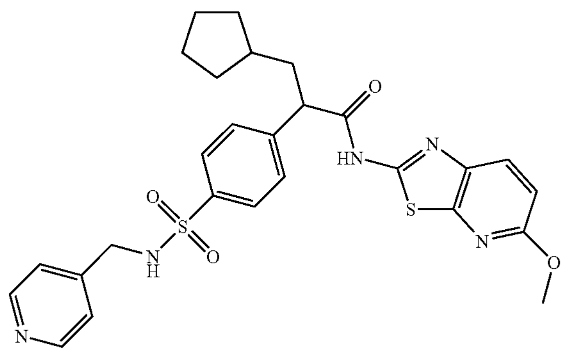 | 3-Cyclopentyl-N-(5-methoxy-thiazolo[5,4-b]pyridin-2-yl)-2-{4-[(pyridin-4-ylmethyl)-sulfamoyl]-phenyl}-propionamide | 552.69 |
| 29-17 | 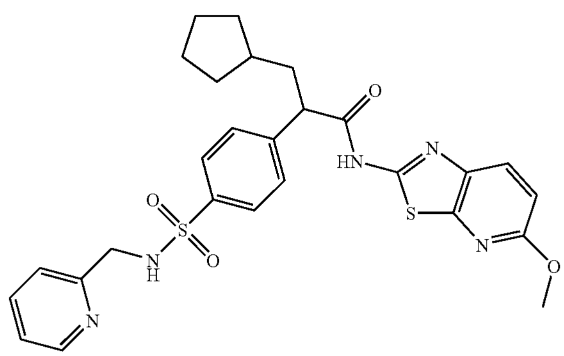 | 3-Cyclopentyl-N-(5-methoxy-thiazolo[5,4-b]pyridin-2-yl)-2-{4-[(pyridin-2-ylmethyl)-sulfamoyl]-phenyl}-propionamide | 552.69 |
| 29-18 | 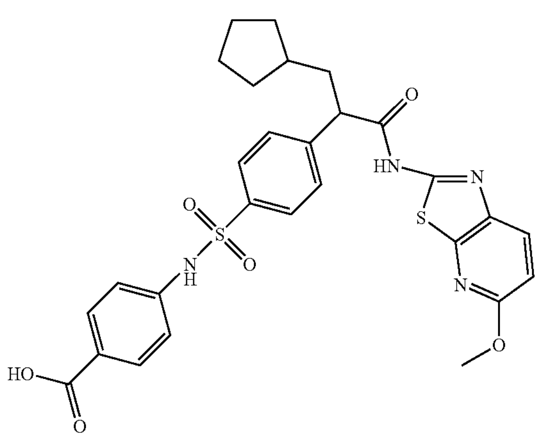 | 4-{4-[2-Cyclopentyl-1-(5-methoxy-thiazolo[5,4-b]pyridin-2-ylcarbamoyl)-ethyl]-benzenesulfonylamino}-benzoic acid | 581.69 |

-continued

| Example | Structure | Chemical name | MS; M + 1+ |
|---|---|---|---|
| 29-19 | 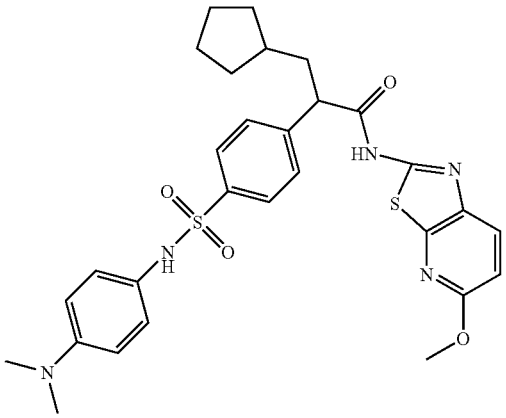 | 3-Cyclopentyl-2-[4-(4-dimethylamino-phenylsulfamoyl)-phenyl]-N-(5-methoxy-thiazolo[5,4-b]pyridin-2-yl)-propionamide | 580.75 |
| 29-20 | 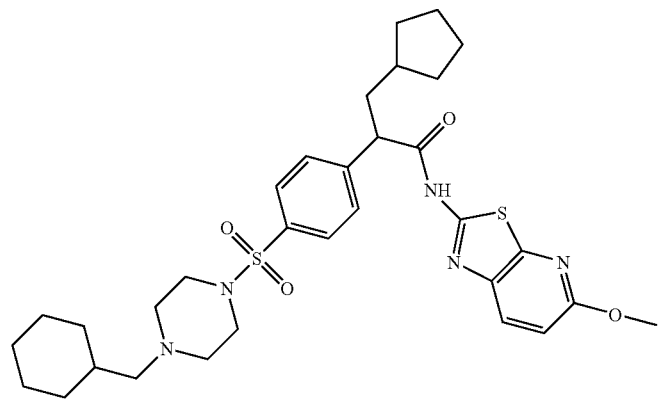 | 2-[4-(4-Cyclohexylmethyl-piperazine-1-sulfonyl)-phenyl]-3-cyclopentyl-N-(5-methoxy-thiazolo[5,4-b]pyridin-2-yl)-propionamide | 626.86 |
| 29-21 | 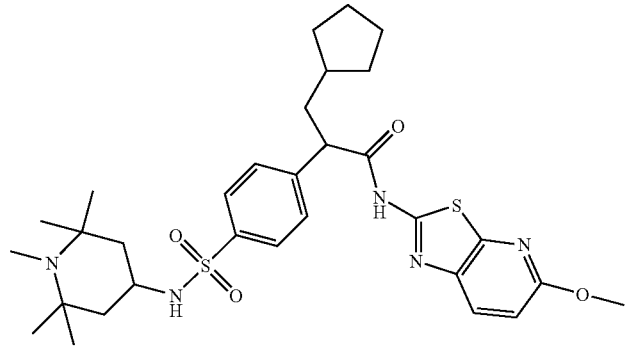 | 3-Cyclopentyl-N-(5-methoxy-thiazolo[5,4-b]pyridin-2-yl)-2-[4-(1,2,2,6,6-pentamethyl-piperidin-4-ylsulfamoyl)-phenyl]-propionamide | 614.85 |
| 29-22 | 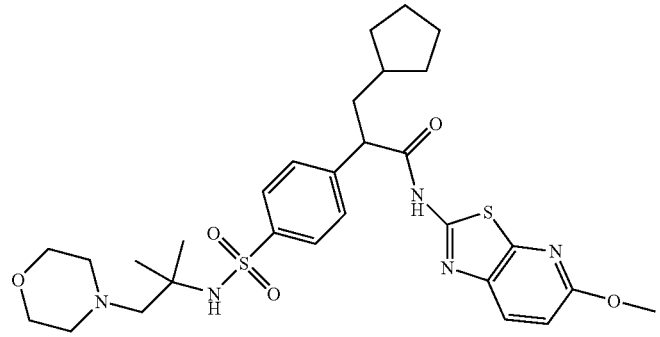 | 3-Cyclopentyl-2-[4-(1,1-dimethyl-2-morpholin-4-yl-ethylsulfamoyl)-phenyl]-N-(5-methoxy-thiazolo[5,4-b]pyridin-2-yl)-propionamide | 602.79 |

-continued

| Example | Structure | Chemical name | MS; M + 1+ |
|---|---|---|---|
| 29-23 | 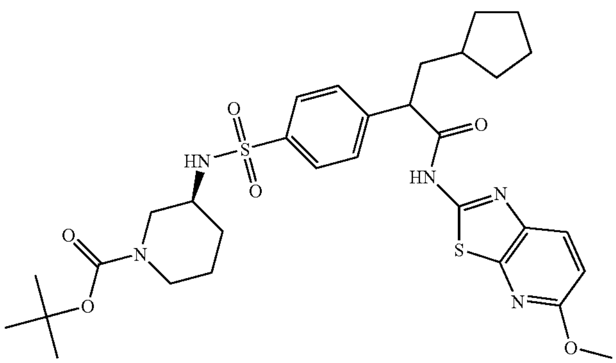 | (S)-3-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester | 644.83 |
| 29-24 | 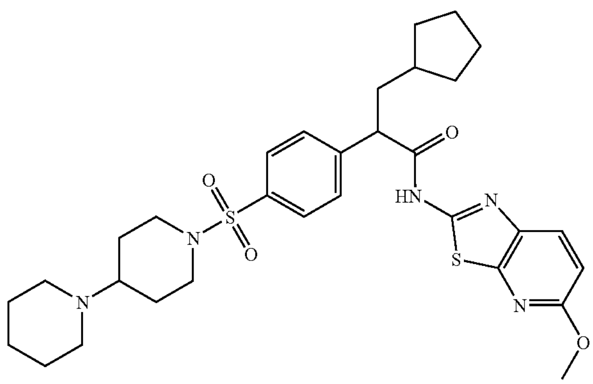 | 2-[4-([1,4']Bipiperidinyl-1'-sulfonyl)-phenyl]-3-cyclopentyl-N-(5-methoxy-thiazolo[5,4-b]pyridin-2-yl)-propionamide | 612.83 |
| 29-25 | 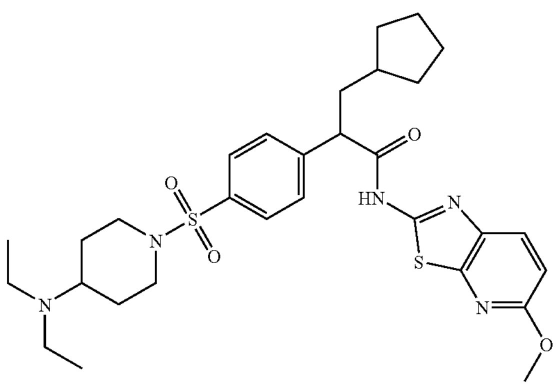 | 3-Cyclopentyl-2-[4-(4-diethylamino-piperidine-1-sulfonyl)-phenyl]-N-(5-methoxy-thiazolo[5,4-b]pyridin-2-yl)-propionamide | 600.82 |
| 29-26 | 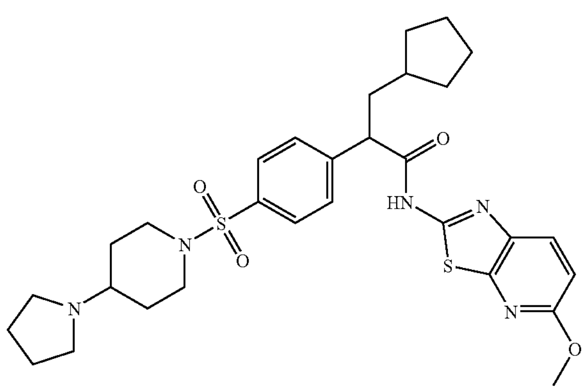 | 3-Cyclopentyl-N-(5-methoxy-thiazolo[5,4-b]pyridin-2-yl)-2-[4-(4-pyrrolidin-1-yl-piperidine-1-sulfonyl)-phenyl]-propionamide | 598.8 |

-continued

| Example | Structure | Chemical name | MS; M + 1+ |
|---|---|---|---|
| 29-27 | 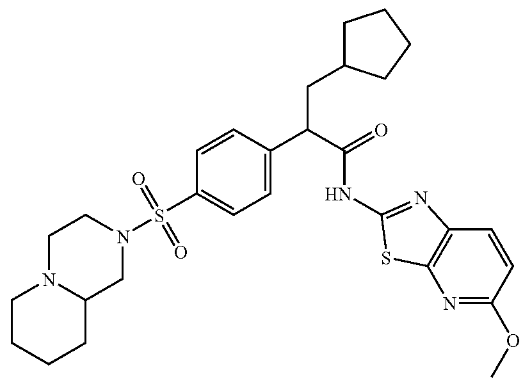 | 3-Cyclopentyl-N-(5-methoxy-thiazolo[5,4-b]pyridin-2-yl)-2-[4-(octahydro-pyrido[1,2-a]pyrazine-2-sulfonyl)-phenyl]-propionamide | 584.78 |
| 29-28 | 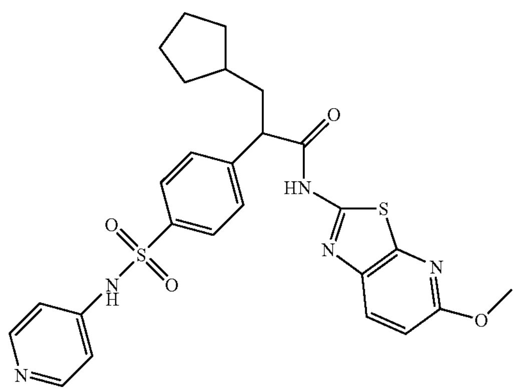 | 3-Cyclopentyl-N-(5-methoxy-thiazolo[5,4-b]pyridin-2-yl)-2-[4-(pyridin-4-ylsulfamoyl)-phenyl]-propionamide | 538.66 |
| 29-29 | 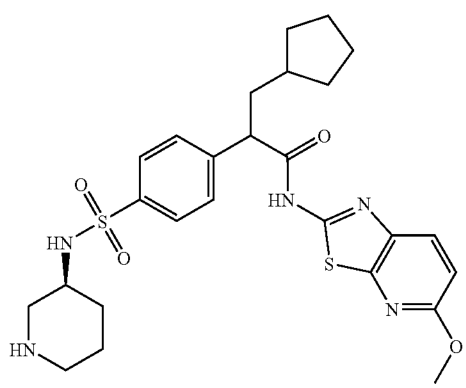 | 3-Cyclopentyl-N-(5-methoxy-thiazolo[5,4-b]pyridin-2-yl)-2-[4-((S)-piperidin-3-ylsulfamoyl)-phenyl]-propionamide | 544.71 |
| 29-30 | 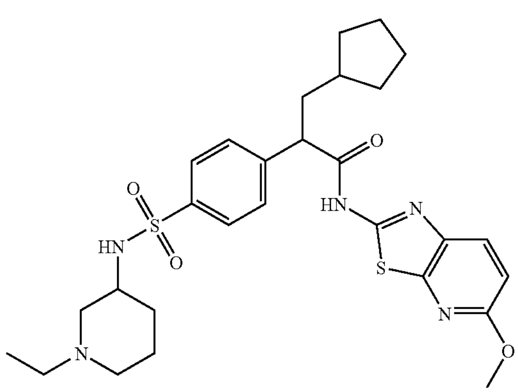 | 3-Cyclopentyl-2-[4-(1-ethyl-piperidin-3-ylsulfamoyl)-phenyl]-N-(5-methoxy-thiazolo[5,4-b]pyridin-2-yl)-propionamide | 572.77 |

-continued

| Example | Structure | Chemical name | MS; M + 1+ |
|---|---|---|---|
| 29-31 | 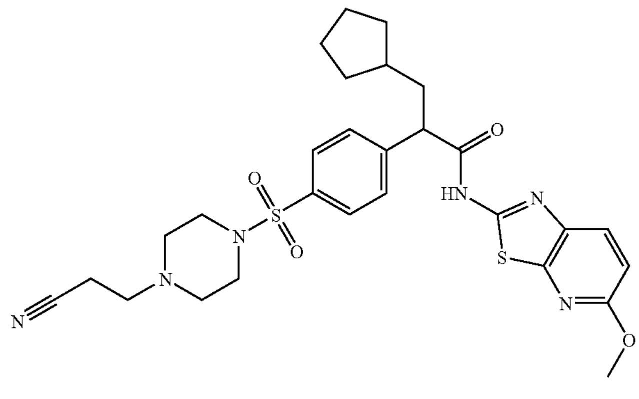 | 2-{4-[4-(2-Cyano-ethyl)-piperazine-1-sulfonyl]-phenyl}-3-cyclopentyl-N-(5-methoxy-thiazolo[5,4-b]pyridin-2-yl)-propionamide | 583.75 |
| 29-32 | 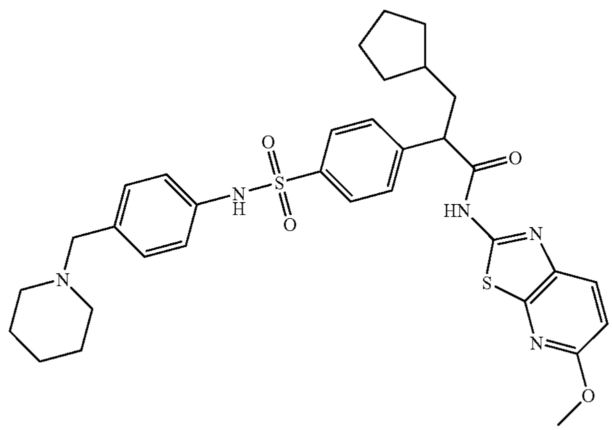 | 3-Cyclopentyl-N-(5-methoxy-thiazolo[5,4-b]pyridin-2-yl)-2-[4-(4-piperidin-1-ylmethyl-phenylsulfamoyl)-phenyl]-propionamide | 634.84 |
| 29-33 | 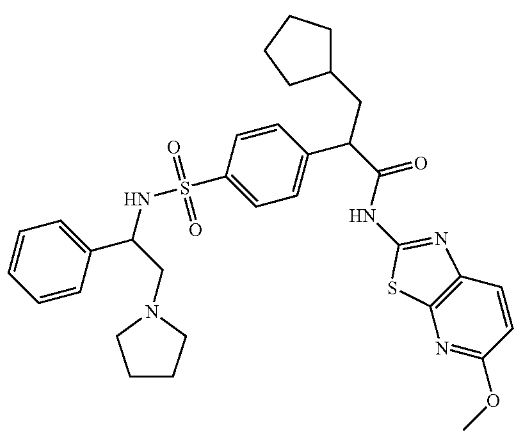 | 3-Cyclopentyl-N-(5-methoxy-thiazolo[5,4-b]pyridin-2-yl)-2-[4-(1-phenyl-2-pyrrolidin-1-yl-ethylsulfamoyl)-phenyl]-propionamide | 634.84 |

-continued

| Example | Structure | Chemical name | MS; M + 1+ |
|---|---|---|---|
| 29-34 | 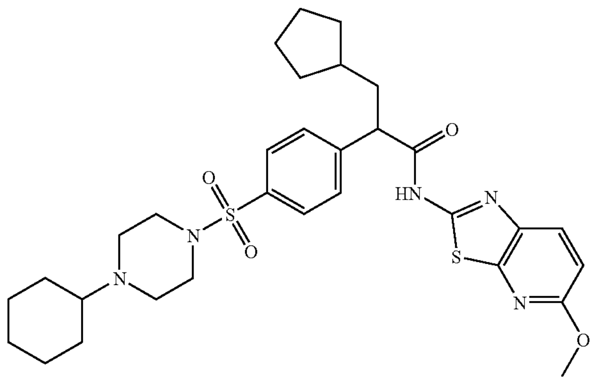 | 2-[4-(4-Cyclohexyl-piperazine-1-sulfonyl)-phenyl]-3-cyclopentyl-N-(5-methoxy-thiazolo[5,4-b]pyridin-2-yl)-propionamide | 612.83 |
| 29-35 | 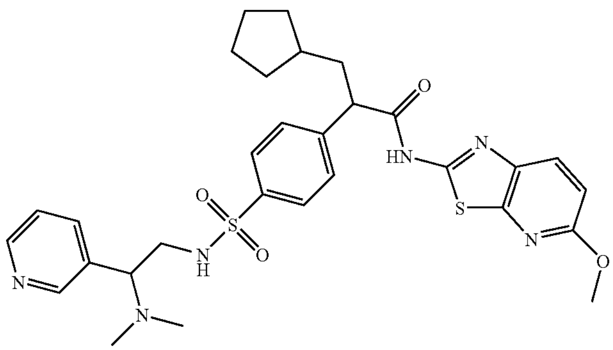 | 3-Cyclopentyl-2-[4-(2-dimethylamino-2-pyridin-3-yl-ethylsulfamoyl)-phenyl]-N-(5-methoxy-thiazolo[5,4-b]pyridin-2-yl)-propionamide | 609.79 |
| 29-36 | 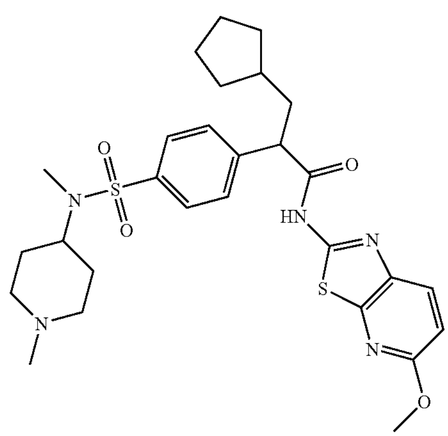 | 3-Cyclopentyl-N-(5-methoxy-thiazolo[5,4-b]pyridin-2-yl)-2-{4-[methyl-(1-methyl-piperidin-4-yl)-sulfamoyl]-phenyl}-propionamide | 572.77 |
| 29-37 | 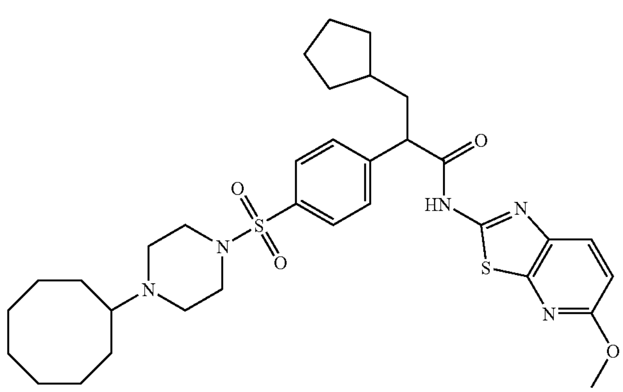 | 2-[4-(4-Cyclooctyl-piperazine-1-sulfonyl)-phenyl]-3-cyclopentyl-N-(5-methoxy-thiazolo[5,4-b]pyridin-2-yl)-propionamide | 640.89 |

-continued

| Example | Structure | Chemical name | MS; M + 1+ |
|---|---|---|---|
| 29-38 | 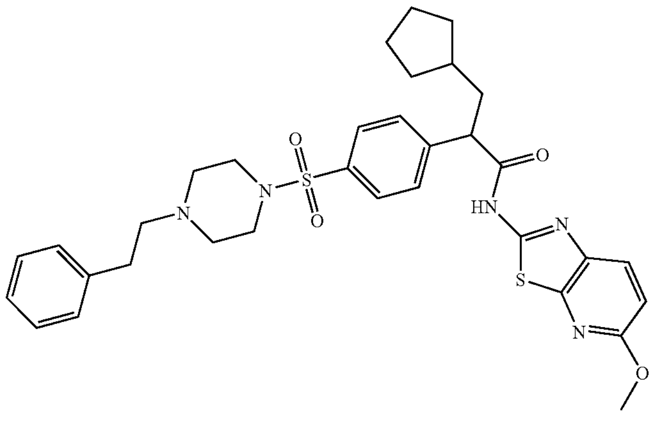 | 3-Cyclopentyl-N-(5-methoxy-thiazolo[5,4-b]pyridin-2-yl)-2-[4-(4-phenethyl-piperazine-1-sulfonyl)-phenyl]-propionamide | 634.84 |
| 29-39 | 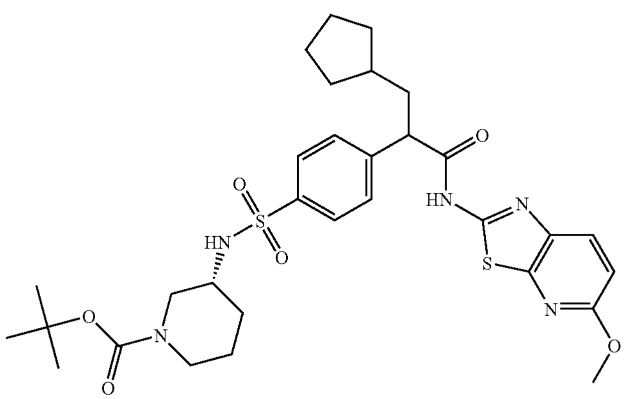 | (R)-3-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester | 644.83 |
| 29-40 | 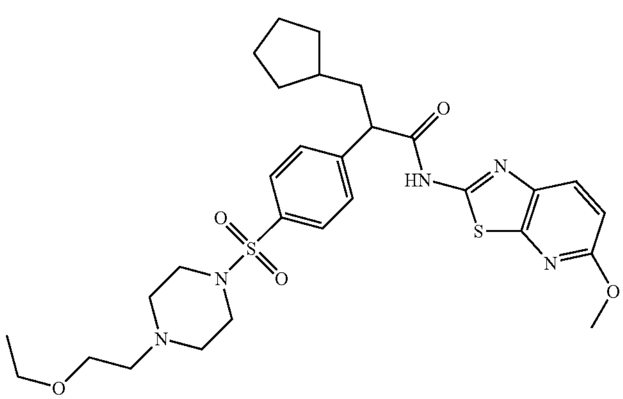 | 3-Cyclopentyl-2-{4-[4-(2-ethoxy-ethyl)-piperazine-1-sulfonyl]-phenyl}-N-(5-methoxy-thiazolo[5,4-b]pyridin-2-yl)-propionamide | 602.79 |

-continued

| Example | Structure | Chemical name | MS; M + 1+ |
|---|---|---|---|
| 29-41 | 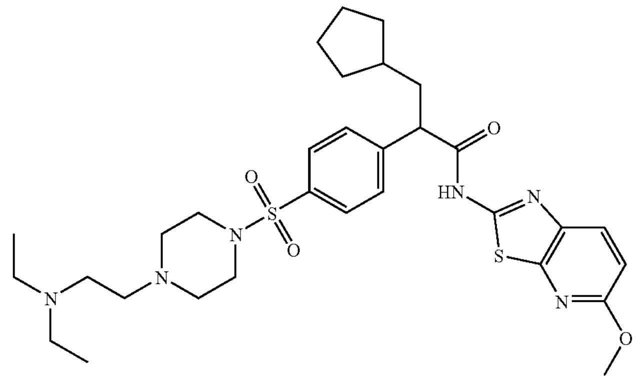 | 3-Cyclopentyl-2-{4-[4-(2-diethylamino-ethyl)-piperazine-1-sulfonyl]-phenyl}-N-(5-methoxy-thiazolo[5,4-b]pyridin-2-yl)-propionamide | 629.86 |
| 29-42 | 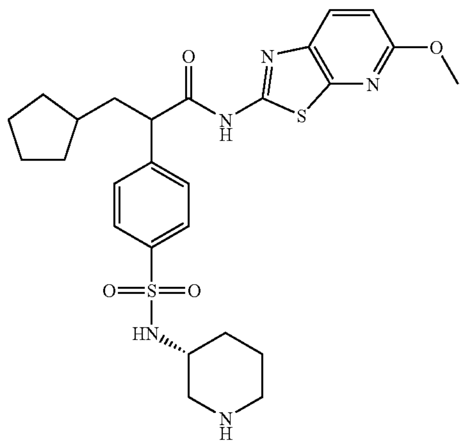 | 3-Cyclopentyl-N-(5-methoxy-thiazolo[5,4-b]pyridin-2-yl)-2-[4-((R)-piperidin-3-ylsulfamoyl)-phenyl]-propionamide | 544.71 |
| 29-43 | 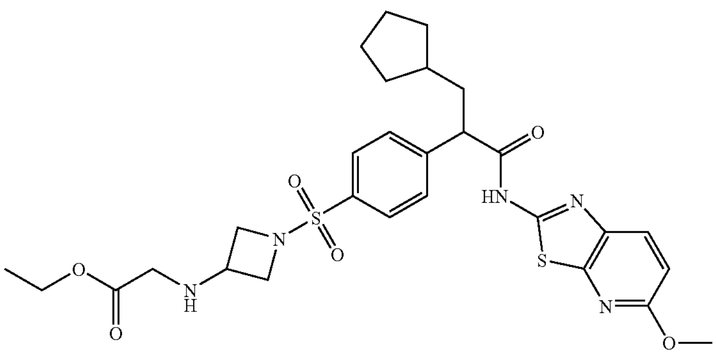 | (1-{4-[2-Cyclopentyl-1-(5-methoxy-thiazolo[5,4-b]pyridin-2-ylcarbamoyl)-ethyl]-benzenesulfonyl}-azetidin-3-ylamino)-acetic acid ethyl ester | 602.75 |
| 29-44 | 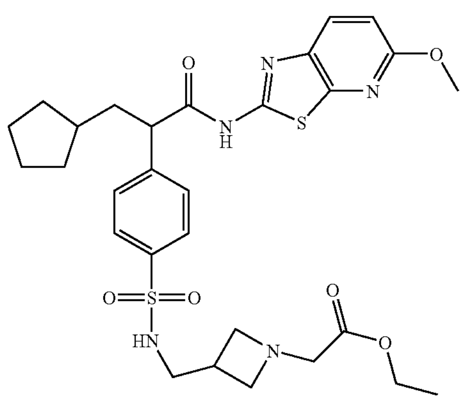 | [3-({4-[2-Cyclopentyl-1-(5-methoxy-thiazolo[5,4-b]pyridin-2-ylcarbamoyl)-ethyl]-benzenesulfonylamino}-methyl)-azetidin-1-yl]-acetic acid ethyl ester | 616.78 |

-continued

| Example | Structure | Chemical name | MS; M + 1+ |
|---|---|---|---|
| 29-45 | 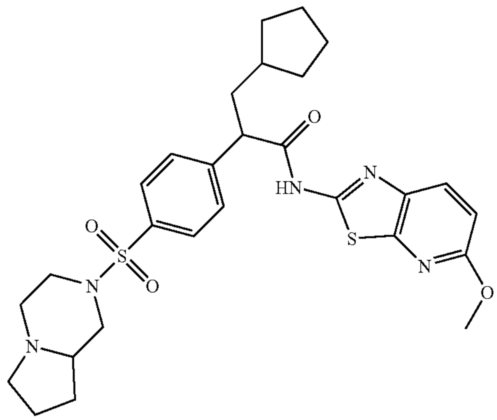 | 3-Cyclopentyl-2-[4-(hexahydro-pyrrolo[1,2-a]pyrazine-2-sulfonyl)-phenyl]-N-(5-methoxy-thiazolo[5,4-b]pyridin-2-yl)-propionamide | 570.75 |
| 29-46 | 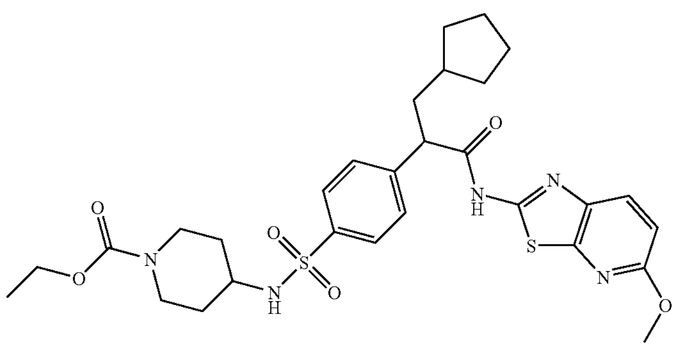 | 4-{4-[2-Cyclopentyl-1-(5-methoxy-thiazolo[5,4-b]pyridin-2-ylcarbamoyl)-ethyl]-benzenesulfonylamino}-piperidine-1-carboxylic acid ethyl ester | 616.78 |
| 29-47 | 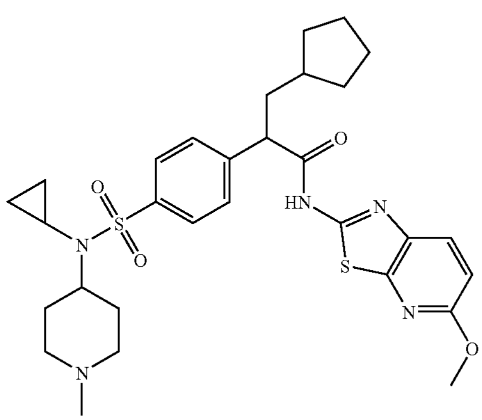 | 3-Cyclopentyl-2-{4-[cyclopropyl-(1-methyl-piperidin-4-yl)-sulfamoyl]-phenyl}-N-(5-methoxy-thiazolo[5,4-b]pyridin-2-yl)-propionamide | 598.8 |

| Example | Structure | Chemical name | MS; M + 1+ |
|---|---|---|---|
| 29-48 | 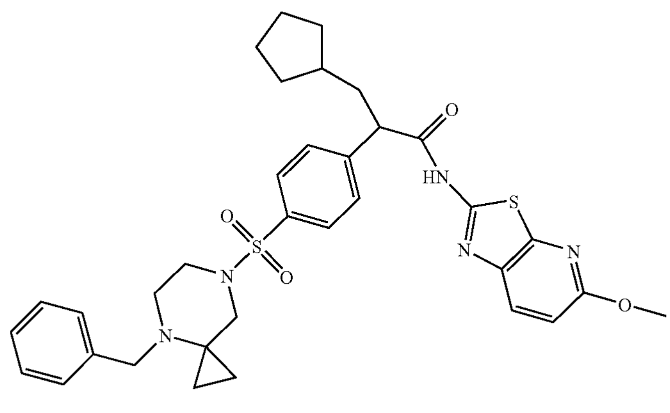 | 2-[4-(4-Benzyl-4,7-diaza-spiro[2.5]octane-7-sulfonyl)-phenyl]-3-cyclopentyl-N-(5-methoxy-thiazolo[5,4-b]pyridin-2-yl)-propionamide | 646.85 |
| 29-49 | 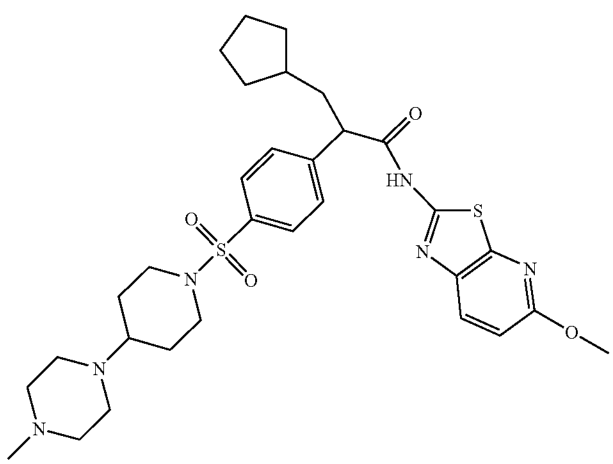 | 3-Cyclopentyl-N-(5-methoxy-thiazolo[5,4-b]pyridin-2-yl)-2-{4-[4-(4-methyl-piperazin-1-yl)-piperidine-1-sulfonyl]-phenyl}-propionamide | 627.85 |
| 29-50 | 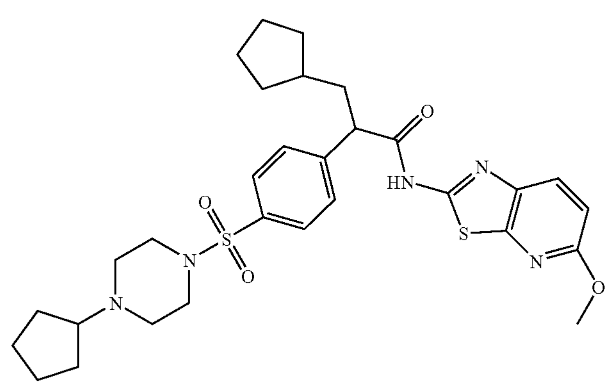 | 3-Cyclopentyl-2-[4-(4-cyclopentyl-piperazine-1-sulfonyl)-phenyl]-N-(5-methoxy-thiazolo[5,4-b]pyridin-2-yl)-propionamide | 598.8 |

-continued

| Example | Structure | Chemical name | MS; M + 1+ |
|---|---|---|---|
| 29-51 | 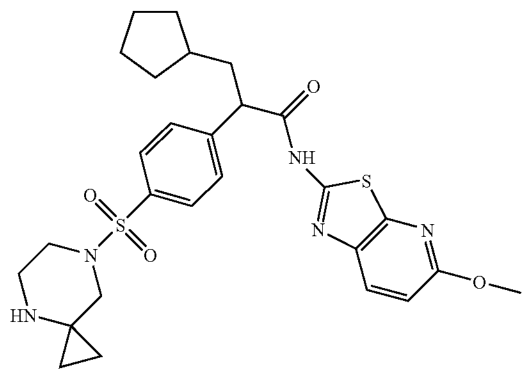 | 3-Cyclopentyl-2-[4-(4,7-diaza-spiro[2.5]octane-7-sulfonyl)-phenyl]-N-(5-methoxy-thiazolo[5,4-b]pyridin-2-yl)-propionamide | 556.72 |
| 29-52 | 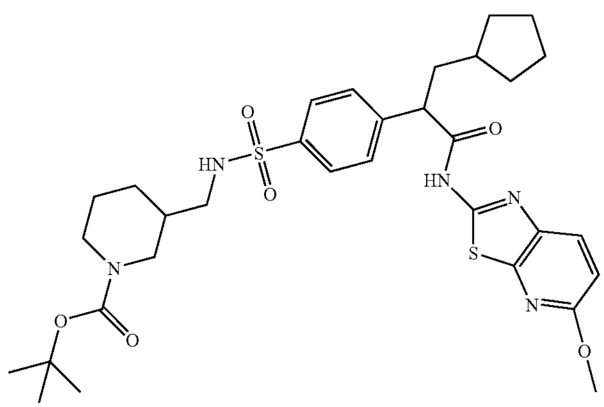 | 3-({4-[2-Cyclopentyl-1-(5-methoxy-thiazolo[5,4-b]pyridin-2-ylcarbamoyl)-ethyl]-benzenesulfonylamino}-methyl)-piperidine-1-carboxylic acid tert-butyl ester | 658.86 |
| 29-53 | 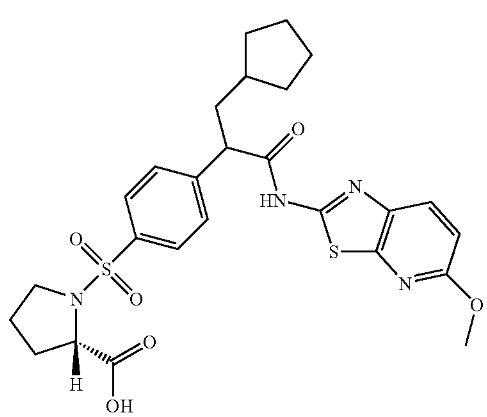 | (S)-1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid | 559.68 |

-continued

| Example | Structure | Chemical name | MS; M + 1+ |
|---|---|---|---|
| 29-54 | 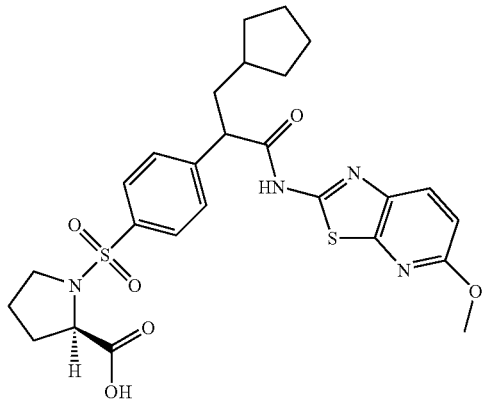 | (R)-1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid | 559.68 |
| 29-55 | 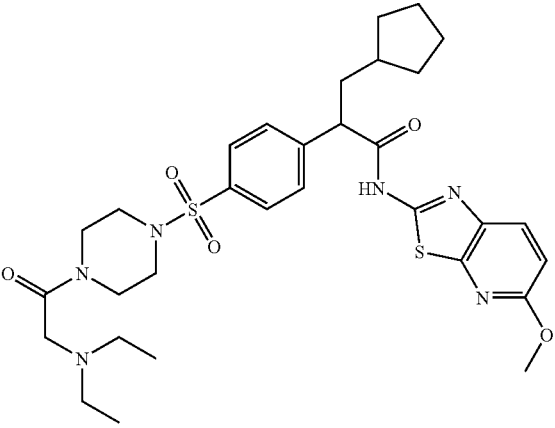 | 3-Cyclopentyl-2-{4-[4-(2-diethylamino-acetyl)-piperazine-1-sulfonyl]-phenyl}-N-(5-methoxy-thiazolo[5,4-b]pyridin-2-yl)-propionamide | 643.85 |
| 29-56 | 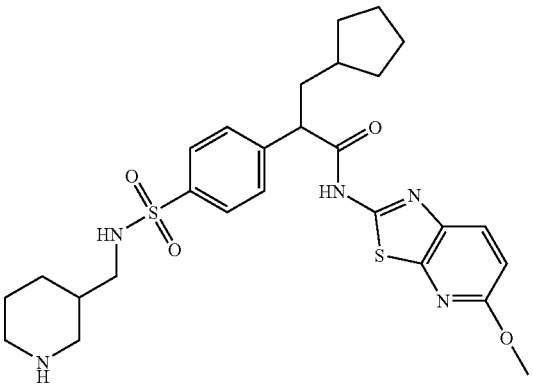 | 3-Cyclopentyl-N-(5-methoxy-thiazolo[5,4-b]pyridin-2-yl)-2-{4-[(piperidin-3-ylmethyl)-sulfamoyl]-phenyl}-propionamide | 558.74 |
| 29-57 | 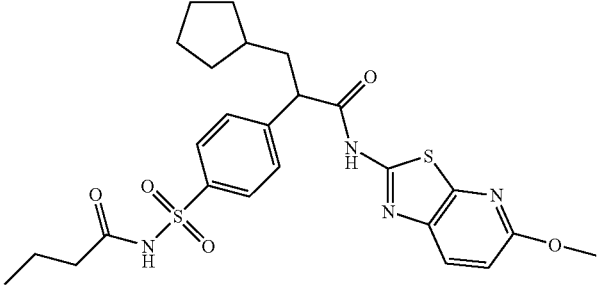 | 2-(4-Butyrylsulfamoyl-phenyl)-3-cyclopentyl-N-(5-methoxy-thiazolo[5,4-b]pyridin-2-yl)-propionamide | 531.67 |

| Example | Structure | Chemical name | MS; M + 1+ |
|---|---|---|---|
| 29-58 | 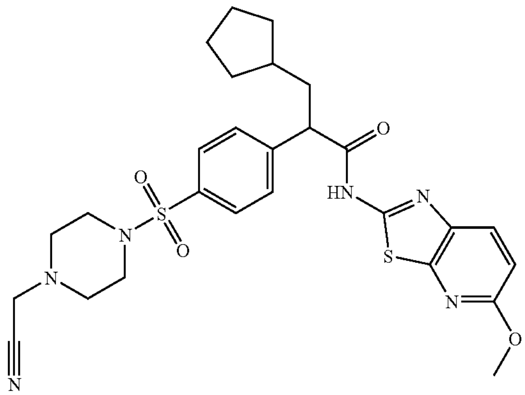 | 2-[4-(4-Cyanomethyl-piperazine-1-sulfonyl)-phenyl]-3-cyclopentyl-N-(5-methoxy-thiazolo[5,4-b]pyridin-2-yl)-propionamide | 569.72 |
| 29-59 | 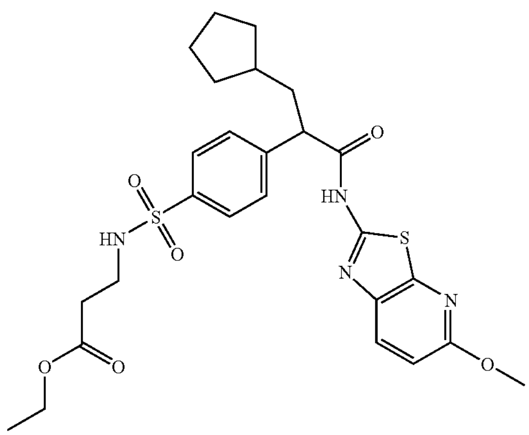 | 3-{4-[2-Cyclopentyl-1-(5-methoxy-thiazolo[5,4-b]pyridin-2-ylcarbamoyl)-ethyl]-benzenesulfonylamino}-propionic acid ethyl ester | 561.7 |
| 29-60 | 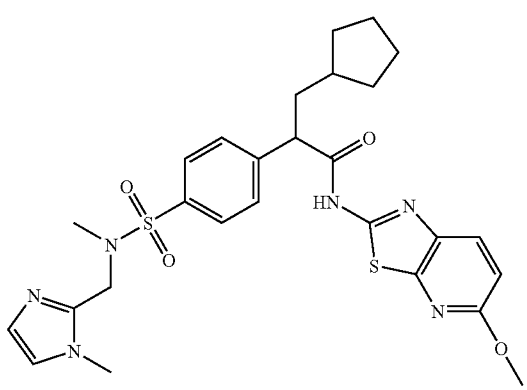 | 3-Cyclopentyl-N-(5-methoxy-thiazolo[5,4-b]pyridin-2-yl)-2-{4-[methyl-(1-methyl-1H-imidazol-2-ylmethyl)-sulfamoyl]-phenyl}-propionamide | 569.72 |

-continued

| Example | Structure | Chemical name | MS; M + 1+ |
|---|---|---|---|
| 29-61 | 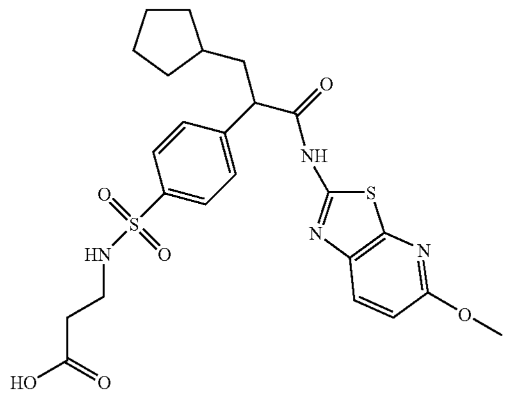 | 3-{4-[2-Cyclopentyl-1-(5-methoxy-thiazolo[5,4-b]pyridin-2-ylcarbamoyl)-ethyl]-benzenesulfonylamino}-propionic acid | 533.64 |
| 29-62 | 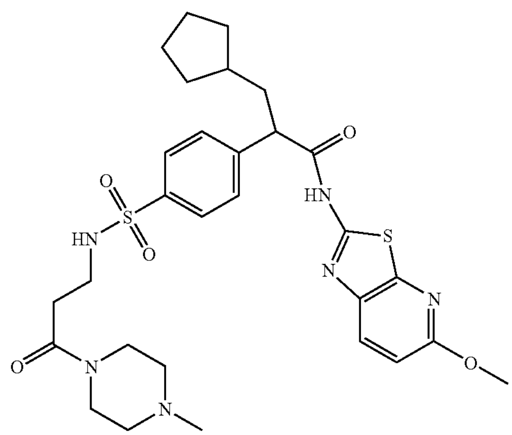 | 3-Cyclopentyl-N-(5-methoxy-thiazolo[5,4-b]pyridin-2-yl)-2-{4-[3-(4-methyl-piperazin-1-yl)-3-oxo-propylsulfamoyl]-phenyl}-propionamide | 615.79 |
| 29-63 | 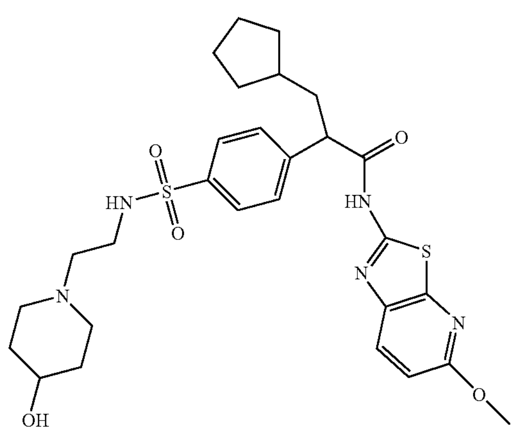 | 3-Cyclopentyl-2-{4-[2-(4-hydroxy-piperidin-1-yl)-ethylsulfamoyl]-phenyl}-N-(5-methoxy-thiazolo[5,4-b]pyridin-2-yl)-propionamide | 588.77 |

-continued

| Example | Structure | Chemical name | MS; M + 1+ |
|---|---|---|---|
| 29-64 | 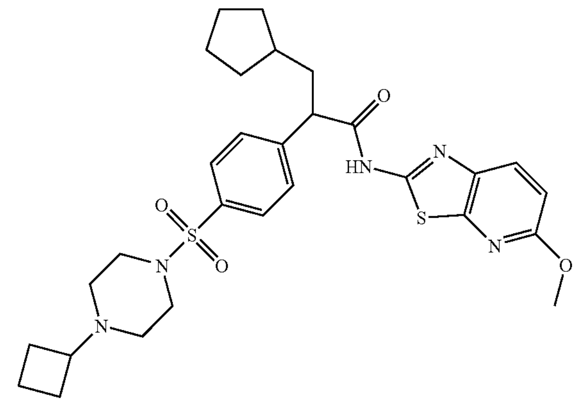 | 2-[4-(4-Cyclobutyl-piperazine-1-sulfonyl)-phenyl]-3-cyclopentyl-N-(5-methoxy-thiazolo[5,4-b]pyridin-2-yl)-propionamide | 584.78 |
| 29-65 | 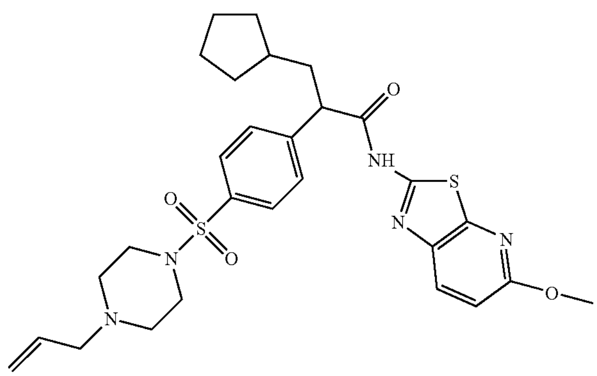 | 2-[4-(4-Allyl-piperazine-1-sulfonyl)-phenyl]-3-cyclopentyl-N-(5-methoxy-thiazolo[5,4-b]pyridin-2-yl)-propionamide | 570.75 |
| 29-66 | 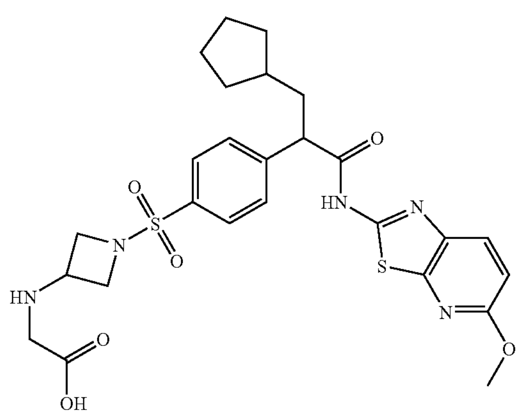 | (2-{4-[2-Cyclopentyl-1-(5-methoxy-thiazolo[5,4-b]pyridin-2-ylcarbamoyl)-ethyl]-benzenesulfonyl}-azetidin-3-ylamino)-acetic acid | 574.69 |

-continued

| Example | Structure | Chemical name | MS; M + 1+ |
|---|---|---|---|
| 29-67 | 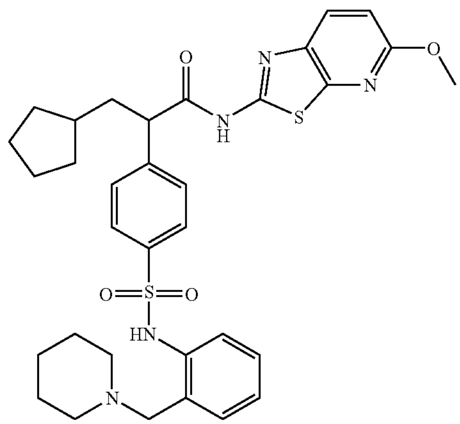 | 3-Cyclopentyl-N-(5-methoxy-thiazolo[5,4-b]pyridin-2-yl)-2-[4-(2-piperidin-1-ylmethyl-phenylsulfamoyl)-phenyl]-propionamide | 634.84 |
| 29-68 | 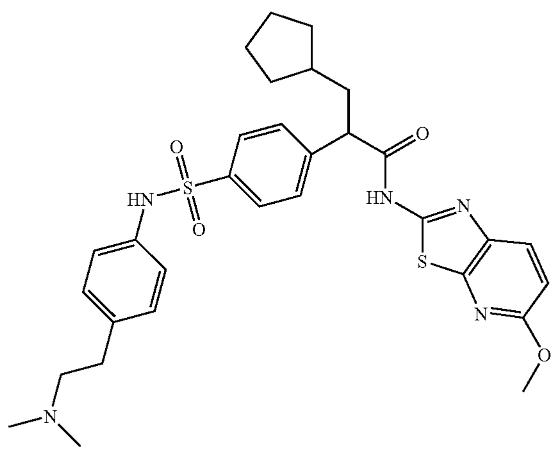 | 3-Cyclopentyl-2-{4-[4-(2-dimethylamino-ethyl)-phenylsulfamoyl]-phenyl}-N-(5-methoxy-thiazolo[5,4-b]pyridin-2-yl)-propionamide | 608.8 |
| 29-69 | 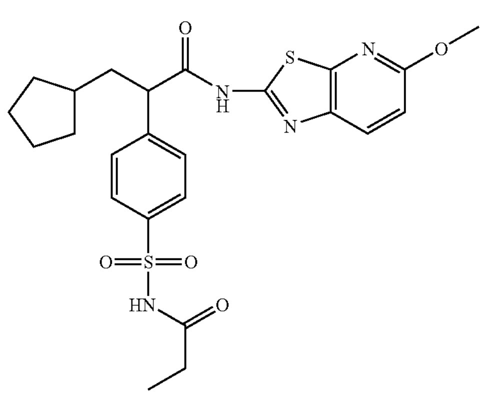 | 3-Cyclopentyl-N-(5-methoxy-thiazolo[5,4-b]pyridin-2-yl)-2-(4-propionylsulfamoyl-phenyl)-propionamide | 517.64 |

-continued

| Example | Structure | Chemical name | MS; M + 1+ |
|---|---|---|---|
| 29-70 | 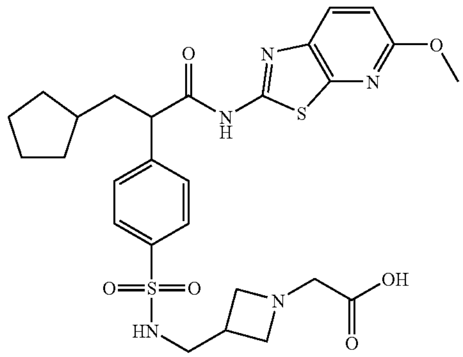 | [3-({4-[2-Cyclopentyl-1-(5-methoxy-thiazolo[5,4-b]pyridin-2-ylcarbamoyl)-ethyl]-benzenesulfonylamino}-methyl)-azetidin-1-yl]-acetic acid | 588.72 |
| 29-71 | 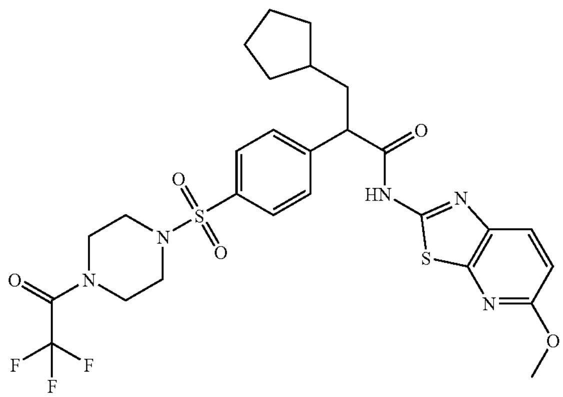 | 3-Cyclopentyl-N-(5-methoxy-thiazolo[5,4-b]pyridin-2-yl)-2-{4-[4-(2,2,2-trifluoro-acetyl)-piperazine-1-sulfonyl]-phenyl}-propionamide | 626.69 |
| 29-72 | 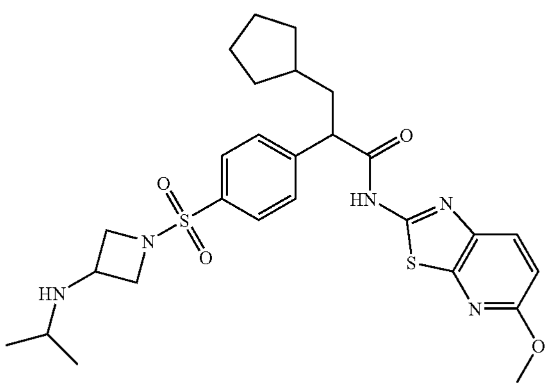 | 3-Cyclopentyl-2-[4-(3-isopropylamino-azetidine-1-sulfonyl)-phenyl]-N-(5-methoxy-thiazolo[5,4-b]pyridin-2-yl)-propionamide | 558.74 |
| 29-73 | 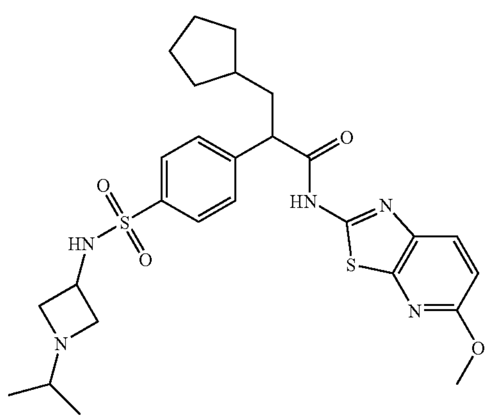 | 3-Cyclopentyl-2-[4-(1-isopropyl-azetidin-3-ylsulfamoyl)-phenyl]-N-(5-methoxy-thiazolo[5,4-b]pyridin-2-yl)-propionamide | 558.74 |

| Example | Structure | Chemical name | MS; M + 1+ |
|---|---|---|---|
| 29-74 | 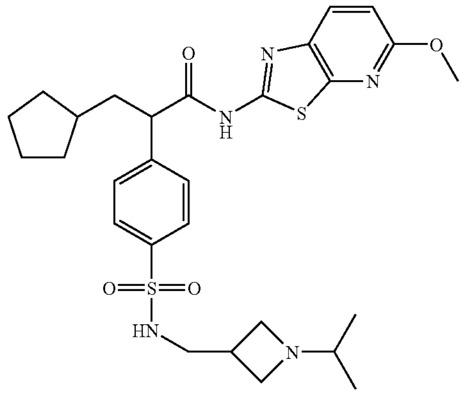 | 3-Cyclopentyl-2-{4-[(1-isopropyl-azetidin-3-ylmethyl)-sulfamoyl]-phenyl}-N-(5-methoxy-thiazolo[5,4-b]pyridin-2-yl)-propionamide | 572.77 |
| 29-75 | 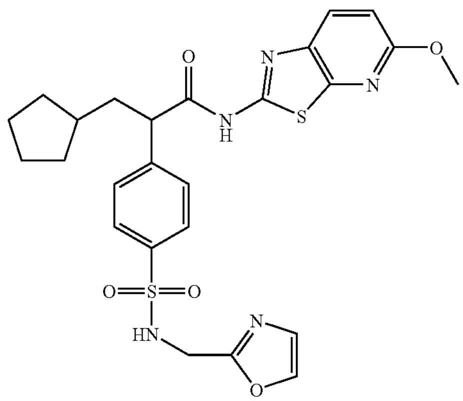 | 3-Cyclopentyl-N-(5-methoxy-thiazolo[5,4-b]pyridin-2-yl)-2-{4-[(oxazol-2-ylmethyl)-sulfamoyl]-phenyl}-propionamide | 542.65 |
| 29-76 | 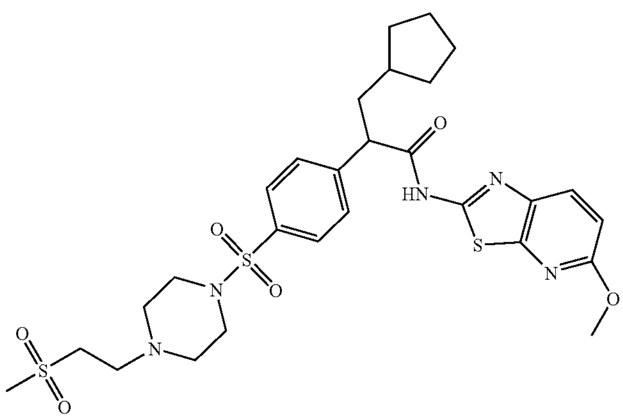 | 3-Cyclopentyl-2-{4-[4-(2-methanesulfonyl-ethyl)-piperazine-1-sulfonyl]-phenyl}-N-(5-methoxy-thiazolo[5,4-b]pyridin-2-yl)-propionamide | 636.83 |
| 29-77 | 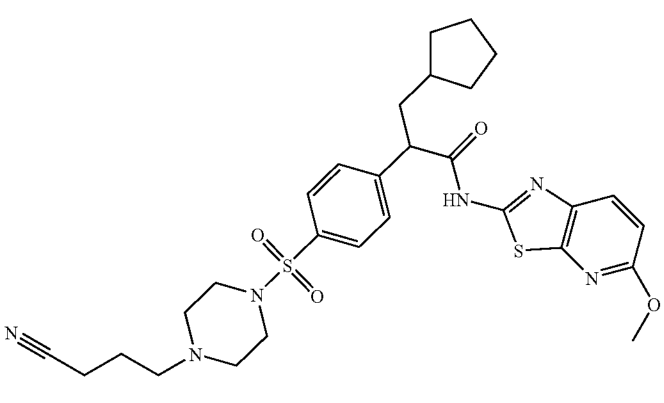 | 2-{4-[4-(3-Cyano-propyl)-piperazine-1-sulfonyl]-phenyl}-3-cyclopentyl-N-(5-methoxy-thiazolo[5,4-b]pyridin-2-yl)-propionamide | 597.78 |

| Example | Structure | Chemical name | MS; M + 1+ |
|---|---|---|---|
| 29-78 | 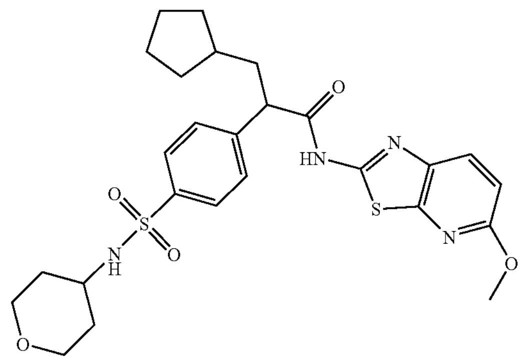 | 3-Cyclopentyl-N-(5-methoxy-thiazolo[5,4-b]pyridin-2-yl)-2-[4-(tetrahydro-pyran-4-ylsulfamoyl)-phenyl]-propionamide | 545.7 |
| 29-79 | 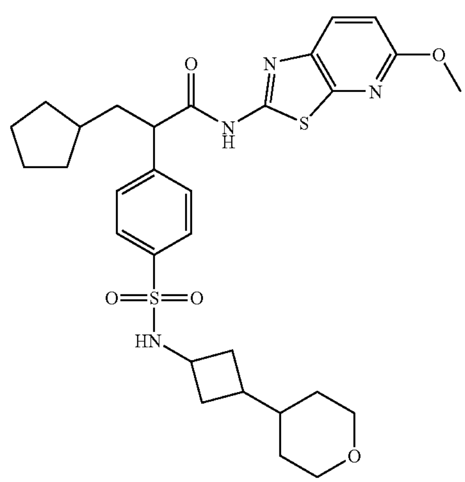 | 3-Cyclopentyl-N-(5-methoxy-thiazolo[5,4-b]pyridin-2-yl)-2-{4-[1-(tetrahydro-pyran-4-yl)-azetidin-3-ylsulfamoyl]-phenyl}-propionamide | 600.78 |
| 29-80 | 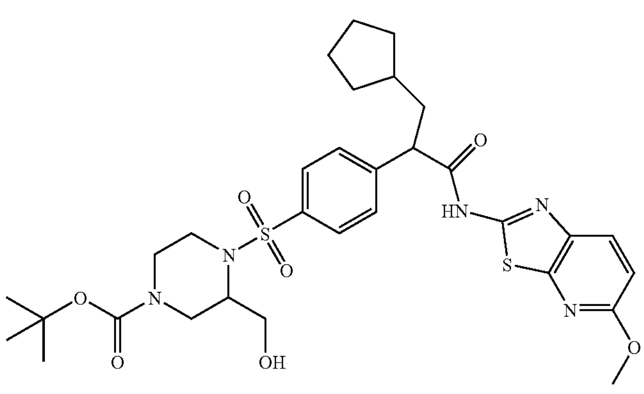 | 4-{4-[2-Cyclopentyl-1-(5-methoxy-thiazolo[5,4-b]pyridin-2-ylcarbamoyl)-ethyl]-benzenesulfonyl}-3-hydroxymethyl-piperazine-1-carboxylic acid tert-butyl ester | 660.83 |

-continued

| Example | Structure | Chemical name | MS; M + 1+ |
|---|---|---|---|
| 29-81 | 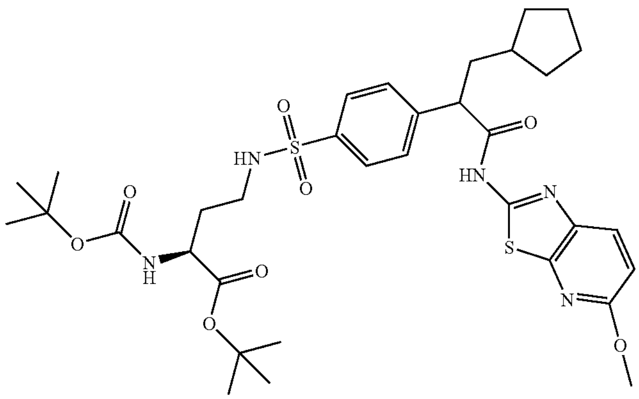 | (S)-2-tert-Butoxycarbonylamino-4-{4-[2-cyclopentyl-1-(5-methoxy-thiazolo[5,4-b]pyridin-2-ylcarbamoyl)-ethyl]-benzenesulfonylamino}-butyric acid tert-butyl ester | 718.91 |
| 29-82 | 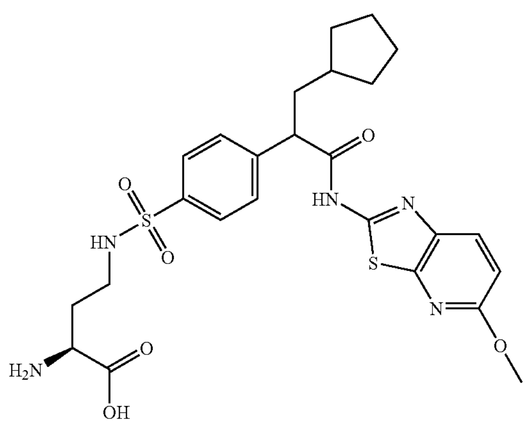 | S)-2-Amino-4-{4-[2-cyclopentyl-1-(5-methoxy-thiazolo[5,4-b]pyridin-2-ylcarbamoyl)-ethyl]-benzenesulfonylamino}-butyric acid | 562.68 |
| 29-83 | 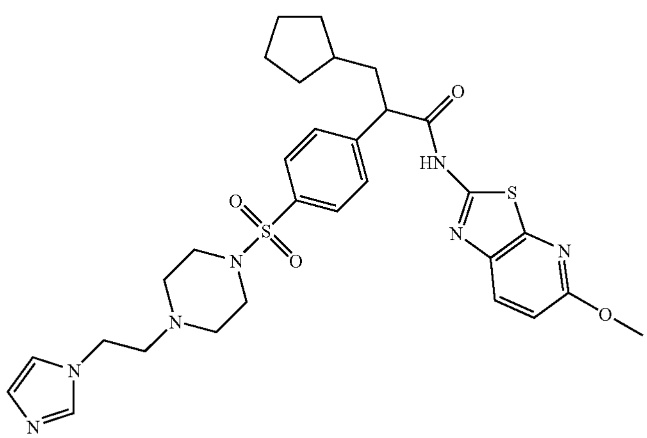 | 3-Cyclopentyl-2-{4-[4-(2-imidazol-1-yl-ethyl)-piperazine-1-sulfonyl]-phenyl}-N-(5-methoxy-thiazolo[5,4-b]pyridin-2-yl)-propionamide | 624.8 |

-continued

| Example | Structure | Chemical name | MS; M + 1+ |
|---|---|---|---|
| 29-84 | 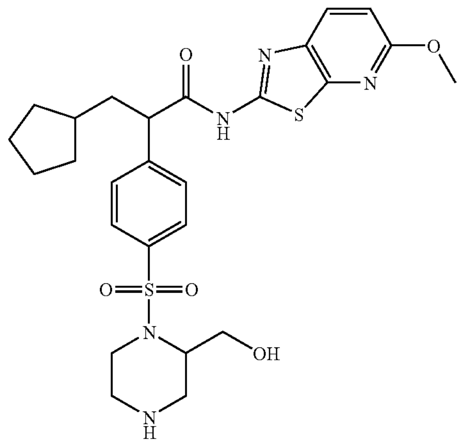 | 3-Cyclopentyl-2-[4-(2-hydroxymethyl-piperazine-1-sulfonyl)-phenyl]-N-(5-methoxy-thiazolo[5,4-b]pyridin-2-yl)-propionamide | 560.71 |
| 29-85 | 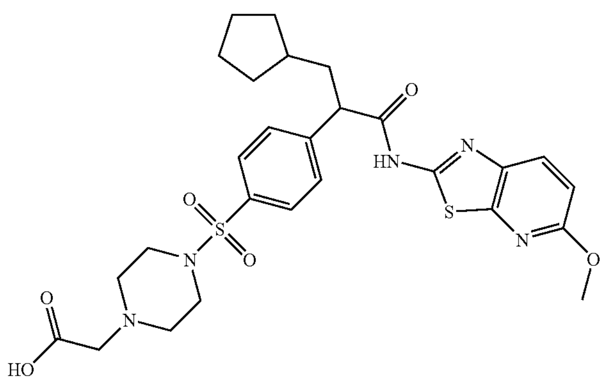 | (4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid | 588.72 |
| 29-86 | 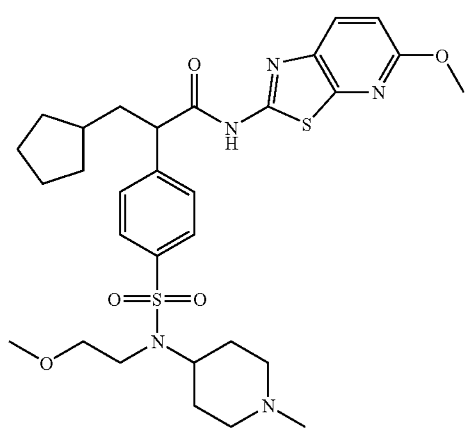 | 3-Cyclopentyl-2-{4-[(2-methoxy-ethyl)-(1-methyl-piperidine-4-yl)-sulfamoyl]-phenyl}-N-(5-methoxy-thiazolo[5,4-b]pyridin-2-yl)-propionamide | 616.82 |

-continued

| Example | Structure | Chemical name | MS; M + 1+ |
|---|---|---|---|
| 29-87 | 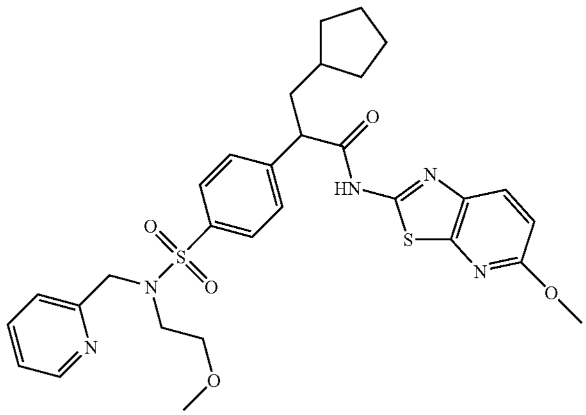 | 3-Cyclopentyl-2-{4-[(2-methoxy-ethyl)-pyridin-2-ylmethyl-sulfamoyl]-phenyl}-N-(5-methoxy-thiazolo[5,4-b]pyridin-2-yl)-propionamide hydrochloride | 610.77 |
| 29-88 | 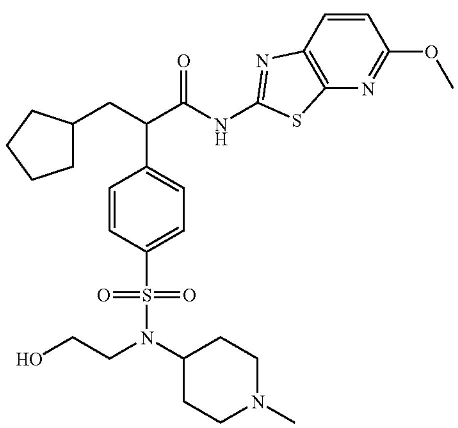 | 3-Cyclopentyl-2-{4-[(2-hydroxy-ethyl)-(1-methyl-piperidin-2-yl)-sulfamoyl]-phenyl}-N-(5-methoxy-thiazolo[5,4-b]pyridin-2-yl)-propionamide | 602.79 |
| 29-89 | 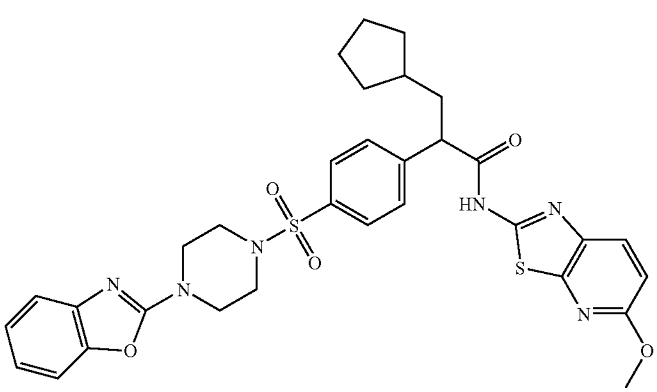 | 2-[4-(4-Benzooxazol-2-yl-piperazine-1-sulfonyl)-phenyl]-3-cyclopentyl-N-(5-methoxy-thiazolo[5,4-b]pyridin-2-yl)-propionamide | 647.79 |

-continued

| Example | Structure | Chemical name | MS; M + 1+ |
|---|---|---|---|
| 29-90 | 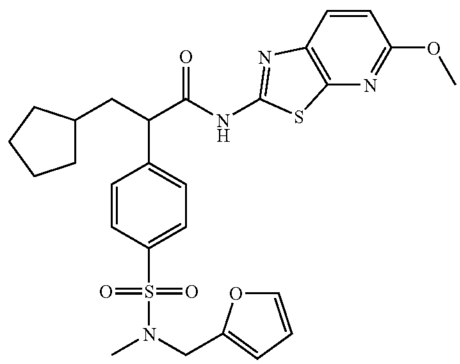 | 3-Cyclopentyl-2-[4-(furan-2-ylmethyl-methyl-sulfamoyl)-phenyl]-N-(5-methoxy-thiazolo[5,4-b]pyridin-2-yl)-propionamide | 555.69 |
| 29-91 | 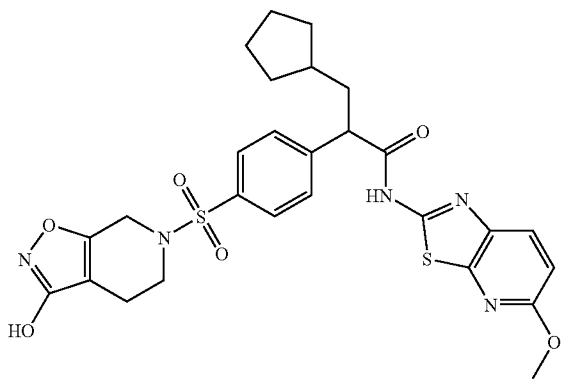 | 3-Cyclopentyl-2-[4-(3-hydroxy-4,7-dihydro-5H-isoxazolo[5,4-c]pyridine-6-sulfonyl)-phenyl]-N-(5-methoxy-thiazolo[5,4-b]pyridin-2-yl)-propionamide | 584.69 |
| 29-92 | 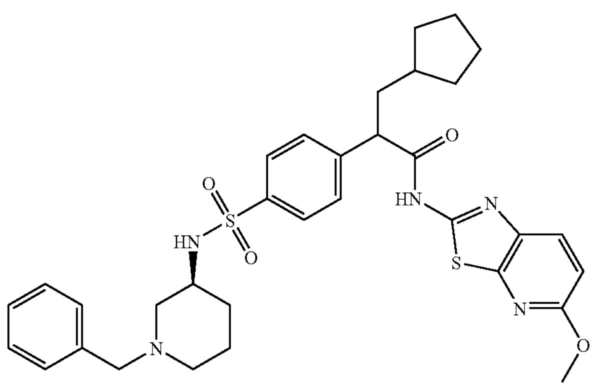 | 2-[4-((S)-1-Benzyl-piperidin-3-ylsulfamoyl)-phenyl]-3-cyclopentyl-N-(5-methoxy-thiazolo[5,4-b]pyridin-2-yl)-propionamide | 634.84 |
| 29-93 | 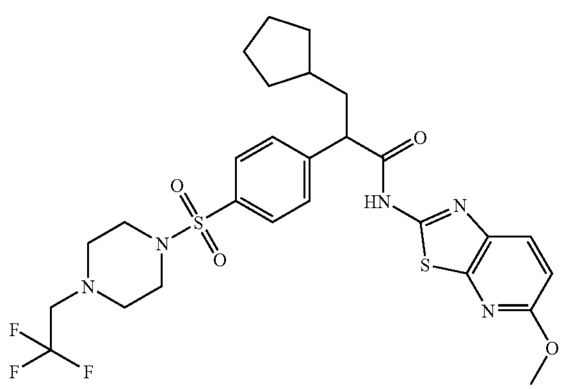 | 3-Cyclopentyl-N-(5-methoxy-thiazolo[5,4-b]pyridin-2-yl)-2-{4-[4-(2,2,2-trifluoro-ethyl)-piperazine-1-sulfonyl]-phenyl}-propionamide | 612.71 |

-continued

| Example | Structure | Chemical name | MS; M + 1+ |
|---|---|---|---|
| 29-94 | 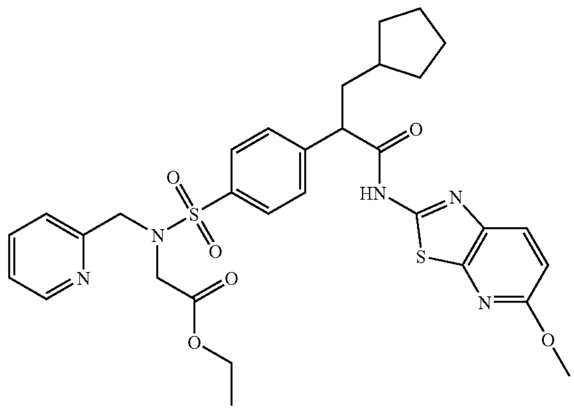 | ({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-acetic acid ethyl ester hydrochloride | 638.78 |
| 29-95 | 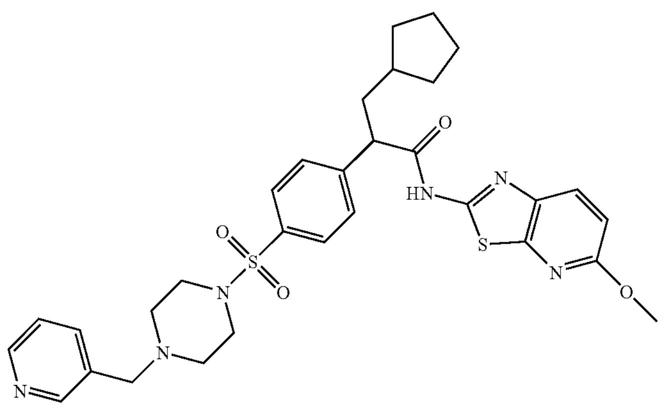 | 3-Cyclopentyl-N-(5-methoxy-thiazolo[5,4-b]pyridin-2-yl)-2-[4-(4-pyridin-3-ylmethyl-piperazine-1-sulfonyl)-phenyl]-propionamide hydrochloride | 621.8 |
| 29-96 | 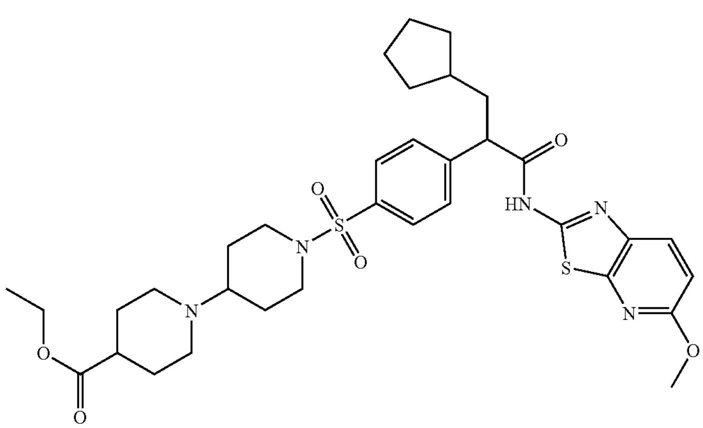 | 1'-{4-[2-Cyclopentyl-1-(5-methoxy-thiazolo[5,4-b]pyridin-2-ylcarbamoyl)-ethyl]-benzenesulfonyl}-[1,4']bipiperidinyl-4-carboxylic acid ethyl ester hydrochloride | 684.9 |

-continued

| Example | Structure | Chemical name | MS; M + 1+ |
|---|---|---|---|
| 29-97 | 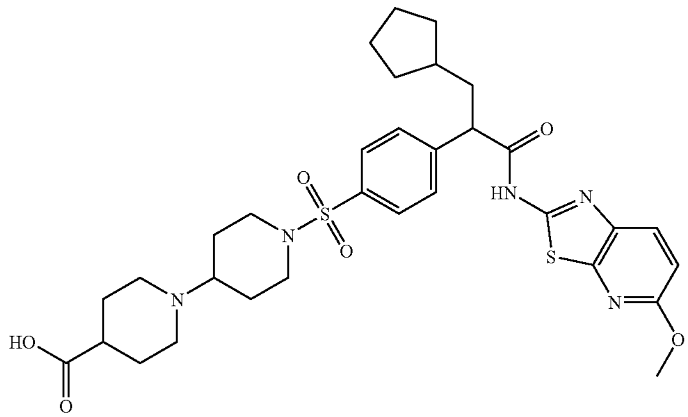 | 1'-{4-[2-Cyclopentyl-1-(5-methoxy-thiazolo[5,4-b]pyridin-2-ylcarbamoyl)-ethyl]-benzenesulfonyl}-[1,4']bipiperidinyl-4-carboxylic acid hydrochloride | 656.84 |
| 29-98 | 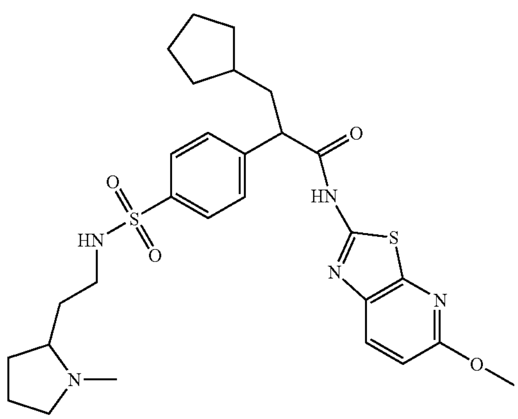 | 3-Cyclopentyl-N-(5-methoxy-thiazolo[5,4-b]pyridin-2-yl)-2-{4-[2-(1-methyl-pyrrolidin-2-yl)-ethylsulfamoyl]-phenyl}-propionamide | 572.77 |
| 29-99 | 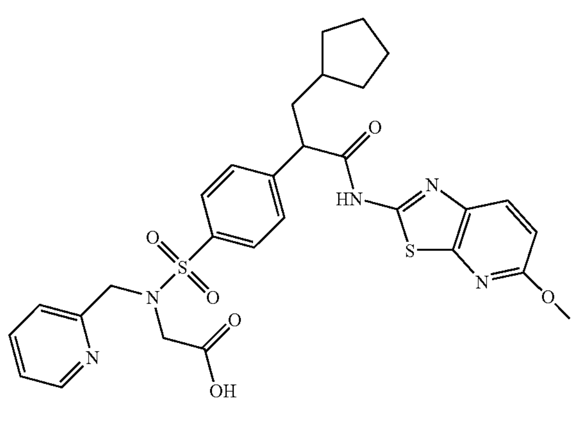 | ({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-acetic acid | 610.73 |

-continued

| Example | Structure | Chemical name | MS; M + 1+ |
|---|---|---|---|
| 29-100 | 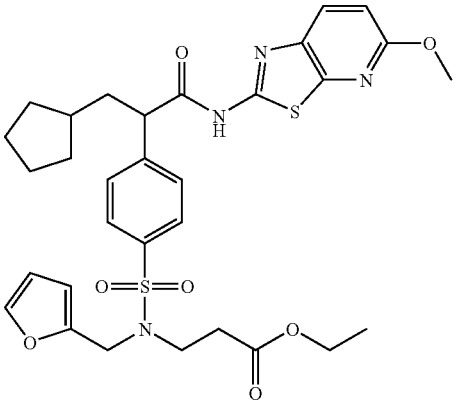 | 3-({4-[2-Cyclopentyl-1-(5-methoxy-thiazolo[5,4-b]pyridin-2-ylcarbamoyl)-ethyl]-benzenesulfonyl}-furan-2-ylmethyl-amino)-propionic acid ethyl ester | 641.78 |
| 29-101 | 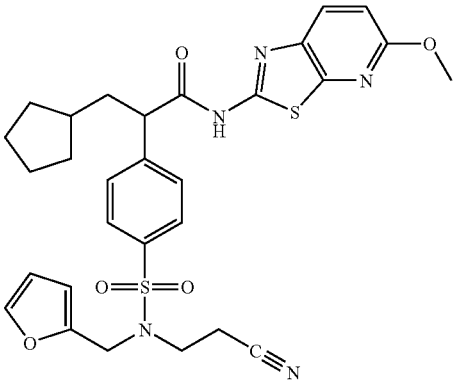 | 2-{4-[(2-Cyano-ethyl)-furan-2-ylmethyl-sulfamoyl]-phenyl}-3-cyclopentyl-N-(5-methoxy-thiazolo[5,4-b]pyridin-2-yl)-propionamide | 594.73 |
| 29-102 | 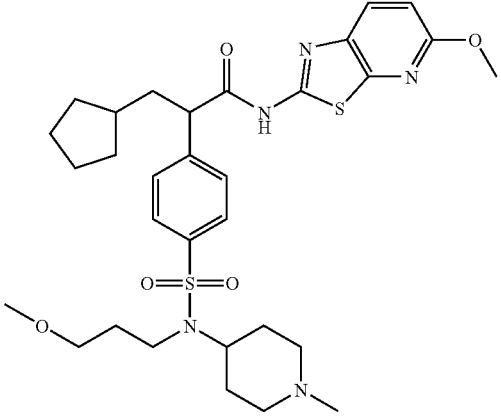 | 3-Cyclopentyl-2-{4-[(3-methoxy-propyl)-(1-methyl-piperidin-4-yl)-sulfamoyl]-phenyl}-N-(5-methoxy-thiazolo[5,4-b]pyridin-2-yl)-propionamide | 630.85 |

-continued

| Example | Structure | Chemical name | MS; M + 1+ |
|---|---|---|---|
| 29-103 | 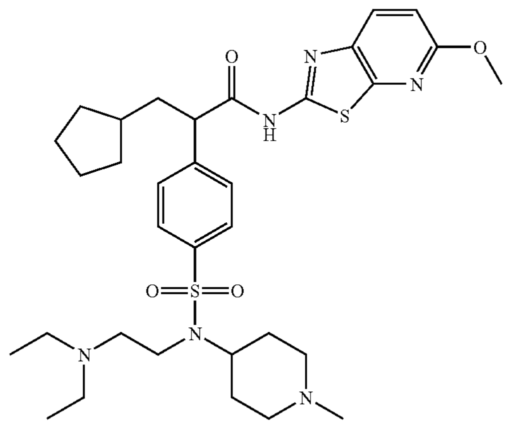 | 3-Cyclopentyl-2-{4-[(2-diethylamino-ethyl)-(1-methyl-piperidin-4-yl)-sulfamoyl]-phenyl}-N-(5-methoxy-thiazolo[5,4-b]pyridin-2-yl)-propionamide | 657.92 |
| 29-104 | 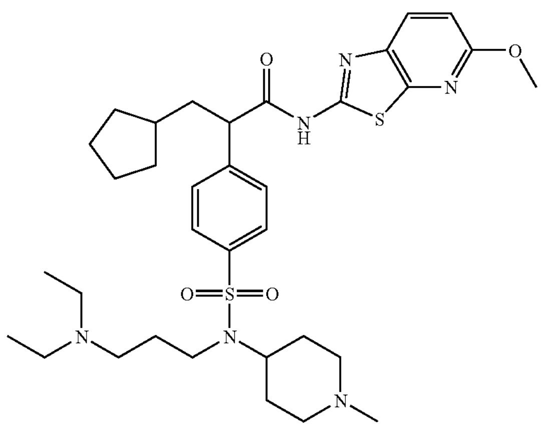 | 3-Cyclopentyl-2-{4-[(3-diethylamino-propyl)-(1-methyl-piperidin-4-yl)-sulfamoyl]-phenyl}-N-(5-methoxy-thiazolo[5,4-b]pyridin-2-yl)-propionamide | 671.94 |
| 29-105 | 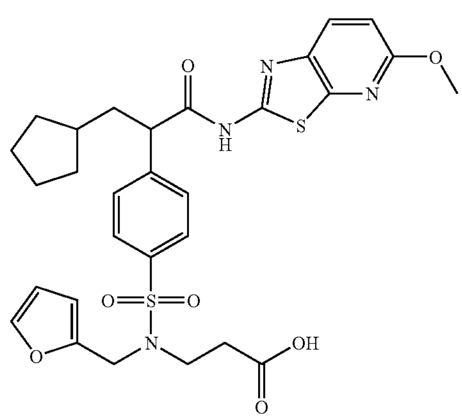 | 3-({4-[2-Cyclopentyl-1-(5-methoxy-thiazolo[5,4-b]pyridin-2-ylcarbamoyl)-ethyl]-benzenesulfonyl}-furan-2-ylmethyl-amino)-propionic acid | 613.73 |

| Example | Structure | Chemical name | MS; M + 1+ |
|---|---|---|---|
| 29-106 | 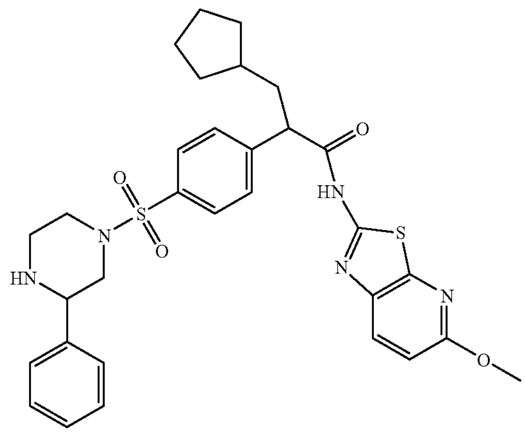 | 3-Cyclopentyl-N-(5-methoxy-thiazolo[5,4-b]pyridin-2-yl)-2-[4-(3-phenyl-piperazine-1-sulfonyl)-phenyl]-propionamide | 606.78 |
| 29-107 | 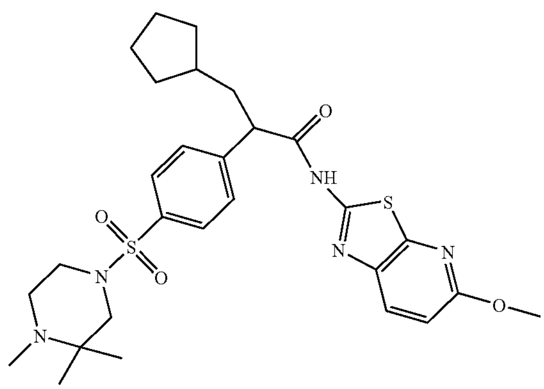 | 3-Cyclopentyl-N-(5-methoxy-thiazolo[5,4-b]pyridin-2-yl)-2-[4-(3,3,4-trimethyl-piperazine-1-sulfonyl)-phenyl]-propionamide | 572.77 |
| 29-108 | 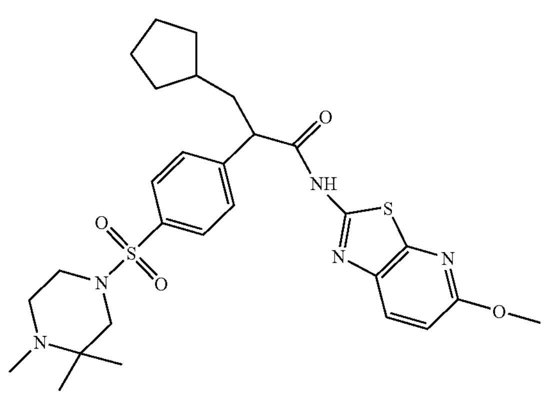 | 3-Cyclopentyl-2-[4-(3,3-dimethyl-piperazine-1-sulfonyl)-phenyl]-N-(5-methoxy-thiazolo[5,4-b]pyridin-2-yl)-propionamide | 558.74 |

| Example | Structure | Chemical name | MS; M + 1⁺ |
|---|---|---|---|
| 29-109 | 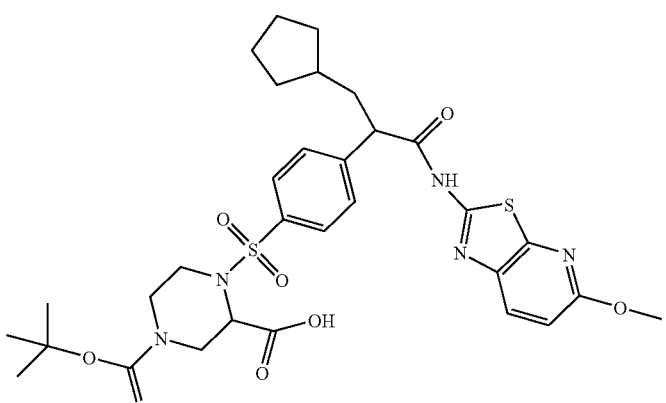 | 4-{4-[2-Cyclopentyl-1-(5-methoxy-thiazolo[5,4-b]pyridin-2-ylcarbamoyl)-ethyl]-benzenesulfonyl}-piperazine-1,3-dicarboxylic acid 1-tert-butyl ester | 674.81 |
| 29-110 | 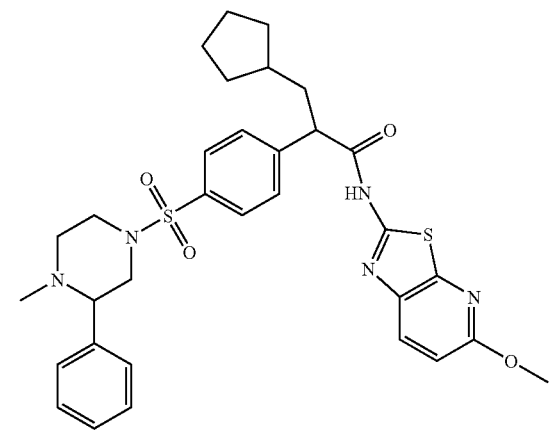 | 3-Cyclopentyl-N-(5-methoxy-thiazolo[5,4-b]pyridin-2-yl)-2-[4-(4-methyl-3-phenyl-piperazine-1-sulfonyl)-phenyl]-propionamide | 620.81 |
| 29-111 | 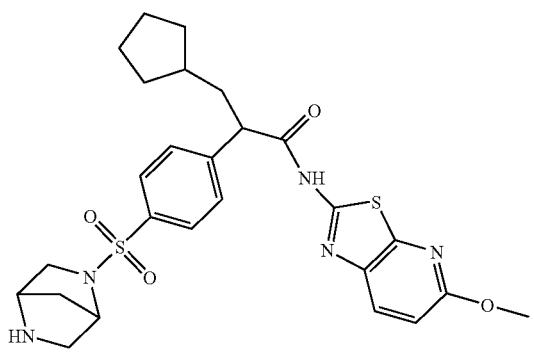 | 3-Cyclopentyl-2-[4-(2,5-diaza-bicyclo[2.2.1]heptane-2-sulfonyl)-phenyl]-N-(5-methoxy-thiazolo[5,4-b]pyridin-2-yl)-propionamide | 542.7 |

What is claimed is:

1. A compound of the formula

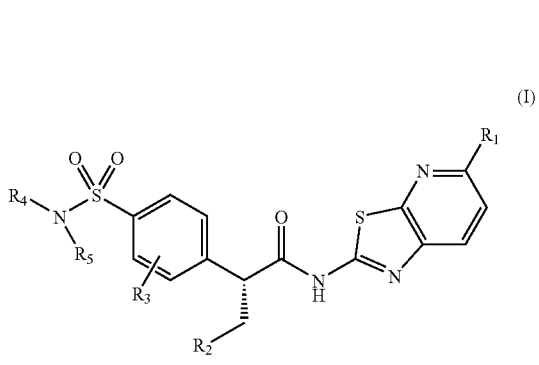

(I)

wherein

R$_1$ is alkoxy;

R$_2$ is C$_3$-C$_6$ cycloalkyl or C$_3$-C$_6$ heterocyclyl;

R$_3$ is hydrogen, halogen, cyano, lower alkyl or lower alkoxy;

R$_4$ is hydrogen, optionally substituted alkyl, or cycloalkyl;

R$_5$ is —(CR$_6$R$_7$)$_m$—W—R$_8$ in which

R$_6$ and R$_7$ are independently hydrogen, optionally substituted alkyl or cycloalkyl; or R$_6$ and R$_7$ combined are alkylene which together with the carbon atom to which they are attached form a 3- to 7-membered ring;

m is zero or an integer from 1 to 5;

W is —NR$_9$— in which

R$_9$ is hydrogen, optionally substituted alkyl or heterocyclyl; or

R$_9$ is —C(O)R$_{10}$, —C(O)OR$_{10}$, or —C(O)NR$_{10}$R$_{11}$ in which

R$_{10}$ is optionally substituted alkyl, cycloalkyl, aryl, heteroaryl, aralkyl or heteroaralkyl;

R$_{11}$ is hydrogen or lower alkyl; or

R$_{11}$ and R$_{10}$ combined are alkylene which together with the nitrogen atom to which they are attached form a 4- to 7-membered ring; or W is absent;

R$_8$ is hydrogen, optionally substituted C$_1$-C$_7$ alkyl, cycloalkyl, aryl or heterocyclyl; or R$_8$ and R$_9$ combined are alkylene which together with the nitrogen atom to which they are attached form a 4- to 7-membered ring; or R$_5$ and R$_4$ combined are alkylene which together with the nitrogen atom to which they are attached form a 4- to 7-membered ring; or R$_5$ and R$_4$ taken together with the nitrogen atom to which they are attached form a 6- to 12-membered fused, bridged or spiral bicyclic ring, which may be optionally substituted or may contain 1 to 3 other heteroatoms selected from oxygen, nitrogen and sulfur;

or an enantiomer thereof; or an enantiomeric mixture thereof; or a pharmaceutically acceptable salt thereof.

2. A compound according to claim 1 of the formula

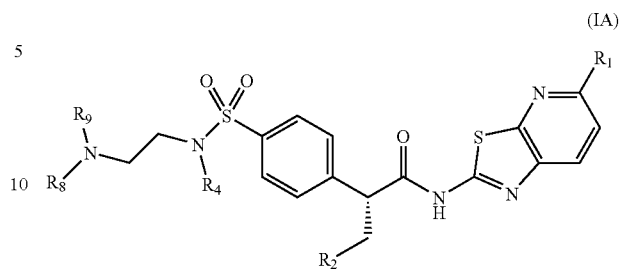

(IA)

wherein

R$_1$ is C$_1$-C$_4$ alkoxy;

R$_2$ is C$_3$-C$_5$ cycloalkyl;

R$_4$ is hydrogen or lower alkyl;

R$_8$ is hydrogen, optionally substituted C$_1$-C$_7$ alkyl, cycloalkyl, aryl or heterocyclyl;

R$_9$ is hydrogen or lower alkyl; or

R$_9$ is —C(O)R$_{10}$, —C(O)OR$_{10}$, or —C(O)NR$_{10}$R$_{11}$ in which

R$_{10}$ is optionally substituted alkyl, cycloalkyl, aryl, heteroaryl, aralkyl or heteroaralkyl;

R$_{11}$ is hydrogen or lower alkyl; or

R$_{11}$ and R$_{10}$ combined are alkylene which together with the nitrogen atom to which they are attached form a 5- to 7-membered ring; or R$_9$ and R$_8$ combined are alkylene which together with the nitrogen atom to which they are attached form a 5- to 7-membered ring;

or an enantiomer thereof; or an enantiomeric mixture thereof; or a pharmaceutically acceptable salt thereof.

3. A compound according to claim 1 of the formula

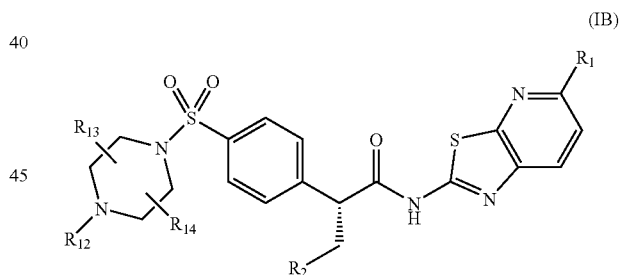

(IB)

wherein

R$_1$ is C$_1$-C$_4$ alkoxy;

R$_2$ is C$_3$-C$_5$ cycloalkyl;

R$_{12}$ is hydrogen, optionally substituted lower alkyl, cycloalkyl, aryl, heteroaryl, aralkyl or heteroaralkyl; or R$_{12}$ is —C(O)R$_{15}$, —C(O)OR$_{15}$, or —C(O)NR$_{15}$R$_{16}$ in which R$_{15}$ optionally substituted alkyl, cycloalkyl, aryl, heteroaryl, aralkyl or heteroaralkyl;

R$_{16}$ is hydrogen or lower alkyl; or

R$_{16}$ and R$_{15}$ combined are alkylene which together with the nitrogen atom to which they are attached form a 5- to 7-membered ring;

R$_{13}$ and R$_{14}$ are independently hydrogen or lower alkyl;

or an enantiomer thereof; or an enantiomeric mixture thereof; or a pharmaceutically acceptable salt thereof.

4. A compound according to claim 3, wherein $R_{12}$ is methyl.

5. A compound according to claim 1 of the formula

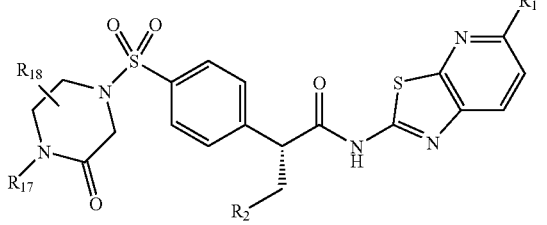

(IC)

wherein
$R_1$ is $C_1$-$C_4$ alkoxy;
$R_2$ is $C_3$-$C_6$ cycloalkyl,
$R_{17}$ is hydrogen, optionally substituted lower alkyl, cycloalkyl, aryl, heteroaryl, aralkyl or heteroaralkyl;
$R_{18}$ is hydrogen or lower alkyl;
or an enantiomer thereof; or an enantiomeric mixture thereof; or a pharmaceutically acceptable salt thereof.

6. A compound according to claim 1 of the formula

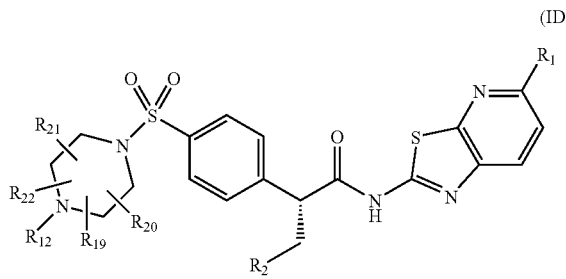

(ID)

wherein
$R_1$ is $C_1$-$C_4$ alkoxy;
$R_2$ is $C_3$-$C_5$ cycloalkyl;
$R_{12}$ is hydrogen, optionally substituted lower alkyl, cycloalkyl, aryl, heteroaryl, aralkyl or heteroaralkyl; or
$R_{12}$ is —C(O)$R_{15}$, —C(O)O$R_{15}$, or —C(O)N$R_{15}R_{16}$ in which
  $R_{15}$ optionally substituted alkyl, cycloalkyl, aryl, heteroaryl, aralkyl or heteroaralkyl;
  $R_{16}$ is hydrogen or lower alkyl; or
  $R_{16}$ and $R_{15}$ combined are alkylene which together with the nitrogen atom to which they are attached form a 5- to 7-membered ring;
$R_{19}$, $R_{20}$, $R_{21}$ and $R_{22}$ are independently hydrogen, optionally substituted lower alkyl, cycloalkyl, aryl or heterocyclyl;
or an enantiomer thereof; or an enantiomeric mixture thereof; or a pharmaceutically acceptable salt thereof.

7. A compound according to claim 1 of the formula

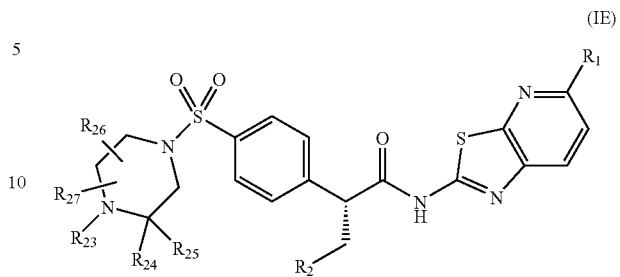

(IE)

wherein
$R_1$ is $C_1$-$C_4$ alkoxy;
$R_2$ is $C_3$-$C_5$ cycloalkyl;
$R_{12}$ is hydrogen, optionally substituted lower alkyl, cycloalkyl, aryl, heteroaryl, aralkyl or heteroaralkyl; or
$R_{23}$ is —C(O)$R_{15}$, —C(O)O$R_{15}$, or —C(O)N$R_{15}R_{16}$ in which
  $R_{15}$ optionally substituted alkyl, cycloalkyl, aryl, heteroaryl, aralkyl or heteroaralkyl;
  $R_{16}$ is hydrogen or lower alkyl; or
  $R_{16}$ and $R_{15}$ combined are alkylene which together with the nitrogen atom to which they are attached form a 5- to 7-membered ring; or
$R_{23}$ and $R_{24}$ combined are alkylene which together with the nitrogen and carbon atoms to which they are attached form a 4- to 7-membered ring;
$R_{25}$ is hydrogen; or
$R_{25}$ and $R_{24}$ combined are alkylene which together with the carbon atom to which they are attached form a 3- to 7-membered ring;
$R_{26}$ and $R_{27}$ are independently optionally substituted lower alkyl, cycloalkyl, aryl or heterocyclyl;
or an enantiomer thereof; or an enantiomeric mixture thereof; or a pharmaceutically acceptable salt thereof.

8. A compound according to claim 1, wherein
$R_1$ is methoxy;
or an enantiomer thereof; or an enantiomeric mixture thereof; or a pharmaceutically acceptable salt thereof.

9. A compound according to claim 1, wherein
$R_2$ is cyclopentyl;
or an enantiomer thereof; or an enantiomeric mixture thereof; or a pharmaceutically acceptable salt thereof.

10. A compound according to claim 1 which is selected from:
3-Cyclopentyl-2-(4-cyclopropylsulfamoyl-phenyl)-N-(5-methoxy-thiazolo[5,4-b]pyridin-2-yl)-propionamide;
3-Cyclopentyl-2-[4-(2-methoxy-ethylsulfamoyl)-phenyl]-N-(5-methoxy-thiazolo[5,4-b]pyridin-2-yl)-propionamide;
3-Cyclopentyl-2-[4-(3-methoxy-benzylsulfamoyl)-phenyl]-N-(5-methoxy-thiazolo[5,4-b]pyridin-2-yl)-propionamide;
3-Cyclopentyl-N-(5-methoxy-thiazolo[5,4-b]pyridin-2-yl)-2-(4-phenylsulfamoyl-phenyl)-propionamide;
2-[4-(2-Carbamoyl-ethylsulfamoyl)-phenyl]-3-cyclopentyl-N-(5-methoxy-thiazolo[5,4-b]pyridin-2-yl)-propionamide;
3-Cyclopentyl-2-(4-diisopropylsulfamoyl-phenyl)-N-(5-methoxy-thiazolo[5,4-b]pyridin-2-yl)-propionamide;
3-Cyclopentyl-2-{4-[(furan-2-ylmethyl)-sulfamoyl]phenyl}-N-(5-methoxy-thiazolo[5,4-b]pyridin-2-yl)-propionamide;

3-Cyclopentyl-N-(5-methoxy-thiazolo[5,4-b]pyridin2-yl)-2-[4-(phenyl-propyl-sulfamoyl)-phenyl]-propionamide;
3-Cyclopentyl-2-(4-dimethylsulfamoyl-phenyl)-N-(5-methoxy-thiazolo[5,4-b]pyridin-2-yl)-propionamide;
3-Cyclopentyl-2-(4-diethylsulfamoyl-phenyl)-N-(5-methoxy-thiazolo[5,4-b]pyridin-2-yl)-propionamide;
3-Cyclopentyl-2-(4-dipropylsulfamoyl-phenyl)-N-(5-methoxy-thiazolo[5,4-b]pyridin-2-yl)-propionamide;
3-Cyclopentyl-N-(5-methoxy-thiazolo[5,4-b]pyridin-2-yl)-2-{4-[(pyridin-3-ylmethyl)-sulfamoyl]-phenyl}-propionamide;
2-(4-Cyclohexylsulfamoyl-phenyl)-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(piperidine-1-sulfonyl)-phenyl]-propionamide;
3-Cyclopentyl-N-(5-methoxy-thiazolo[5,4-b]pyridin-2-yl)-2-[4-(morpholine-4-sulfonyl)-phenyl]-propionamide;
3-Cyclopentyl-N-(5-methoxy-thiazolo[5,4-b]pyridin-2-yl)-2-{4-[(thiophen-2-ylmethyl)-sulfamoyl]-phenyl}-propionamide;
3-Cyclopentyl-N-(5-methoxy-thiazolo[5,4-b]pyridin-2-yl)-2-{4-(pyridin-3-ylsulfamoyl)-phenyl]-propionamide;
3-Cyclopentyl-2-[4-(2-fluoro-benzylsulfamoyl)-phenyl]-N-(5-methoxy-thiazolo[5,4-b]pyridin-2-yl)-propionamide;
3-Cyclopentyl-2-[4-(4-methoxy-benzylsulfamoyl)-phenyl]-N-(5-methoxy-thiazolo[5,4-b]pyridin-2-yl)-propionamide;
2-(4-Benzylsulfamoyl-phenyl)-3-cyclopentyl-N-(5-methoxy-thiazolo[5,4-b]pyridin-2-yl)-propionamide;
2-[4-(Benzyl-methyl-sulfamoyl)-phenyl]-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(4-methyl-piperazine-1-sulfonyl)-phenyl]-propionamide;
3-Cyclopentyl-2-(4-dibutylsulfamoyl-phenyl)-N-(5-methoxy-thiazolo[5,4-b]pyridin-2-yl)-propionamide;
3-Cyclopentyl-2-[4-(4-ethyl-piperazine-1-sulfonyl)-phenyl]-N-(5-methoxy-thiazolo[5,4-b]pyridin-2-yl)-propionamide;
2-[4-(4-Acetyl-piperazine-1-sulfonyl)-phenyl]-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(piperazine-1-sulfonyl)-phenyl]-propionamide hydrochloride;
3-Cyclopentyl-N-(5-methoxy-thiazolo[5,4-b]pyridin-2-yl)-2-[4-(4-phenyl-piperazine-1-sulfonyl)-phenyl]-propionamide;
3-Cyclopentyl-2-{4-[4-(2-methoxy-phenyl)-piperazine-1-sulfonyl]-phenyl}-N-(5-methoxy-thiazolo[5,4-b]pyridin-2-yl)-propionamide;
2-{4-[4-(3-Chloro-phenyl)-piperazine-1-sulfonyl]-phenyl}-3-cyclopentyl-N-(5-methoxy-thiazolo[5,4-b]pyridin-2-yl)-propionamide;
2-[4-(4-Benzyl-piperazine-1-sulfonyl)-phenyl]-3-cyclopentyl-N-(5-methoxy-thiazolo[5,4-b]pyridin-2-yl)-propionamide;
3-Cyclopentyl-2-[4-(4-isopropyl-piperazine-1-sulfonyl)-phenyl]-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(4-o-tolyl-piperazine-1-sulfonyl)-phenyl]-propionamide;
N-[2-(2-{4-[4-(2-Chloro-phenyl)-piperazine-1-sulfonyl]-phenyl}-3-cyclopentyl-propionylamino)-thiazol-5-yl]-acetimidic acid methyl ester;
3-Cyclopentyl-2-{4-[14-(4-fluoro-phenyl)-piperazine-1-sulfonyl]-phenyl}-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(4-pyridin-2-yl-piperazine-1-sulfonyl)-phenyl]-propionamide;
3-Cyclopentyl-2-{4-[(2-hydroxy-ethyl)-methyl-sulfamoyl]-phenyl}-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(4-pyridin-4-yl-piperazine-1-sulfonyl)-phenyl]-propionamide;
3-Cyclopentyl-N-(5-methoxy-thiazolo[5,4-b]pyridin-2-yl)-2-[4-(2-piperidin-1-yl-ethylsulfamoyl)-phenyl]-propionamide;
3-Cyclopentyl-N-(5-methoxy-thiazolo[5,4-b]pyridin-2-yl)-2-[4-(2-pyrrolidin-1-yl-ethylsulfamoyl)-phenyl]-propionamide;
3-Cyclopentyl-2-{4-[(2-dimethylamino-ethyl)-ethyl-sulfamoyl]-phenyl}-N-(5-methoxy-thiazolo[5,4-b]pyridin-2-yl)-propionamide hydrochloride;
3-Cyclopentyl-2-{4-[(2-dimethylamino-ethylsulfamoyl]-phenyl}-N-(5-methoxy-thiazolo[5,4-b]pyridin-2-yl)-propionamide hydrochloride;
3-Cyclopentyl-2-{4-[4-(2-hydroxy-ethyl)-piperazine-1-sulfonyl]-phenyl}-N-(5-methoxy-thiazolo[5,4-b]pyridin-2-yl)-propionamide,
3-Cyclopentyl-N-(5-methoxy-thiazolo[5,4-b]pyridin-2-yl)-2-{4-[methyl-(2-pyrrolidin-1-yl-ethyl)-sulfamoyl]-phenyl}-propionamide hydrochloride;
3-Cyclopentyl-N-(5-methoxy-thiazolo[5,4-b]pyridin-2-yl)-2-{4-[methyl-(2-piperidin-1-yl-ethyl)-sulfamoyl]-phenyl}-propionamide hydrochloride;
3-Cyclopentyl-N-(5-methoxy-thiazolo[5,4-b]pyridin-2-yl)-2-{4[methyl-(2-morpholin-4-yl-ethyl)-sulfamoyl]-phenyl}-propionamide;
4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid ethyl ester;
3-Cyclopentyl-2-{4-[(2-diethylamino-ethyl)-methyl-sulfamoyl]-phenyl}-N-(5-methoxy-thiazolo[5,4-b]pyridin-2-yl)-propionamide;
3-Cyclopentyl-2-{4-[(2-hydroxy-ethylsulfamoyl]-phenyl}-N-(5-methoxy-thiazolo[5,4-b]pyridin-2-yl)-propionamide;
2-[4-(4-Carbamoylmethyl-piperazine-1-sulfonyl)-phenyl]-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(pyrrolidine-1-sulfonyl)-phenyl]-propionamide;
3-Cyclopentyl-N-(5-methoxy-thiazolo[5,4-b]pyridin-2-yl)-2-[4-(pyridin-2-ylsulfamoyl)-phenyl]-propionamide;
4-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester;
4-({4-[2-Cyclopentyl-1-(5-methoxy-thiazolo[5,4-b]pyridin-2-ylcarbamoyl)-ethyl]-benzenesulfonylamino}-methyl)-piperidine-1-carboxylic acid tert-butyl ester;

3-Cyclopentyl-2-{4-[(1-ethyl-pyrrolidin-2-ylmethyl)-sulfamoyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(piperidin-4-ylsulfamoyl)-phenyl]-propionamide;

3-Cyclopentyl-N-(5-methoxy-thiazolo[5,4-b]pyridin-2-yl)-2-{4-[(piperidin-4-ylmethyl)-sulfamoyl]-phenyl}propionamide;

(4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid ethyl ester;

3-Cyclopentyl-2-{4-[(3-hydroxy-5-hydroxymethyl-2-methyl-pyridin-4-ylmethyl)-sulfamoyl]-phenyl}-N-(5-methoxy-thiazolo[5, 4-b]pyridin-2-yl)-propionamide;

3-{4-[2-Cyclopentyl-1-(5-methoxy-thiazolo[5,4-b]pyridin-2-ylcarbamoyl)-ethyl]-benzenesulfonylamino}-azetidine-1-carboxylic acid tert-butyl ester;

(1-{4-[2-Cyclopentyl-1-(5-methoxy-thiazolo[5,4-b]pyridin-2-ylcarbamoyl)-ethyl]-benzenesulfonyl}-azetidin-3-yl)-carbamic acid tert-butyl ester;

3-({4-[2-Cyclopentyl-1-(5-methoxy-thiazolo[5,4-b]pyridin-2-ylcarbamoyl)-ethyl]-benzenesulfonylamino}-methyl)-azetidine-1-carboxylic acid tert-butyl ester;

1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid;

2-[4-(Azetidin-3-ylsulfamoyl)-phenyl]-3-cyclopentyl-N-(5-methoxy-thiazolo[5,4-b]pyridin-2-yl)-propionamide;

2-[4-(3-Amino-azetidine-1-sulfonyl)-phenyl]-3-cyclopentyl-N-(5-methoxy-thiazolo[5,4-b]pyridin-2-yl)-propionamide;

2-{4-[(Azetidin-3-ylmethyl)-sulfamoyl]-phenyl}-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-(4-sulfamoyl-phenyl)-propionamide;

3-Cyclopentyl-N-(5-methoxy-thiazolo[5,4-b]pyridin-2-yl)-2-{4-[(pyridin-4-ylmethyl)-sulfamoyl]-phenyl}-propionamide;

3-Cyclopentyl-N-(5-methoxy-thiazolo[5,4-b]pyridin-2-yl)-2-{4-[(pyridin-2-ylmethyl)-sulfamoyl]-phenyl}-propionamide;

4-{4-[2-Cyclopentyl-1-(5-methoxy-thiazolo[5,4-b]pyridin-2-ylcarbamoyl)-ethyl]-benzenesulfonylamino}-benzoic acid;

3-Cyclopentyl-2-[4-(4-(4-dimethylamino-phenylsulfamoyl)-phenyl]-N-(5-methoxy-thiazolo[5,4-b]pyridin-2-yl)-propionamide;

2-[4-(4-Cyclohexylmethyl-piperazine-1-sulfonyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(1,2,2,6,6-pentamethyl-piperidin-4-ylsulfamoyl)-phenyl]-propionamide;

3-Cyclopentyl-2-[4-(1,1-dimethyl-2-morpholin-4-yl-ethylsulfamoyl)-phenyl]-N-(5-methoxy-thiazolo[5,4-b]pyridin-2-yl)-propionamide;

(S)-3-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester;

2-[4-([1,4']Bipiperidinyl-1'-sulfonyl)-phenyl]-3-cyclopentyl-N-(5-methoxy-thiazolo[5,4-b]pyridin-2-yl)-propionamide;

3-Cyclopentyl-2-[4-(4-diethylamino-piperidine-1-sulfonyl)-phenyl]-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-pyrrolidin-1-yl-piperidine-1-sulfonyl)-phenyl]-propionamide;

3-Cyclopentyl-N-(5-methoxy-thiazolo[5,4-b]pyridin-2-yl)-2-[4-(octahydro-pyrido[1,2-a]pyrazine-2-sulfonyl)-phenyl]-propionamide;

3-Cyclopentyl-N-(5-methoxy-thiazolo[5,4-b]pyridin-2-yl)-2-[4-(pyridin-4-ylsulfamoyl)-phenyl]-propionamide 3-Cyclopentyl-N-(5-methoxy-thiazolo[5,4-b]pyridin-2-yl)-2-[4-((S)-piperidin-3-ylsulfamoyl)-phenlyl]-propionamide;

3-Cyclopentyl-2-[4-(1-ethyl-piperidin-3-ylsulfamoyl)-phenyl]-N-(5-methoxy-thiazolo[5,4-b]pyridin-2-yl)-propionamide;

2-{4-[4-(2-Cyano-ethyl)-piperazine-1-sulfonyl]-phenyl}-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-piperidin-1-ylmethyl-phenylsulfamoyl)-phenyl]-propionamide;

3-Cyclopentyl-N-(5-methoxy-thiazolo[5,4-b]pyridin-2-yl)-2-[4-(1-phenyl-2-pyrrolidin-1-yl-ethylsulfamoyl)-phenyl]-propionamide;

2-[4-(4-Cyclohexyl-piperazine-1-sulfonyl)-phenyl]-3-cyclopentyl-N-(5-methoxy-thiazolo[5,4-b]pyridin-2-yl)-propionamide;

3-Cyclopentyl-2-[4-(2-dimethylamino-2-pyridin-3-yl-ethylsulfamoyl)-phenyl]-N-(5-methoxy-thiazolo[5,4-b]pyridin-2-yl)-propionamide;

3-Cyclopentyl-N-(5-methoxy-thiazolo[5,4-b]pyridin-2-yl)-2-{4-[methyl-(1-methyl-piperidin-4-yl)-sulfamoyl]-phenyl}-propionamide;

2-[4-(4-Cyclooctyl-piperazine-1-sulfonyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2-yl)-2-[4-(4-phenethyl-piperazine-1-sulfonyl)-phenyl]-propionamide, (R)-3-{4-[2-Cyclopentyl-1-(5-methoxy-thiazolo[5,4-b]pyridin-2-ylcarbamoyl)-ethyl]-benzenesulfonylamino}-piperidine-1-carboxylic acid tert-butyl ester;

3-Cyclopentyl-2-{4-[4-(2-ethoxy-ethyl)-piperazine-1-sulfonyl]-phenyl}-N-(5-methoxy-thiazolo[5,4-b]pyridin-2-yl)-propionamide;

3-Cyclopentyl-2-{4-[4-(2-diethylamino-ethyl)-piperazine-1-sulfonyl]-phenyl}-N-(5-methoxy-thiazolo[5,4-b]pyridin-2-yl)-propionamide;

3-Cyclopentyl-N-(5-methoxy-thiazolo[5,4-b]pyridin-2-yl)-2-[4-((R)-piperidine-3-ylsulfamoyl)-phenyl]-propionamide;

(1-{4-[2-Cyclopentyl- 1-(5-methoxy-thiazolo[5,4-b]pyridin-2-ylcarbamoyl)-ethyl]-benzenesulfonyl}-azetidin-3-ylamino)-acetic acid ethyl ester;

[3-({4-[2-Cyclopentyl-1-(5-methoxy-thiazolo[5,4-b]pyridin-2-ylcarbamoyl)-ethyl]-benzenesulfonylamino}-methyl)-azetidin-1-yl]-acetic acid ethyl ester;

3-Cyclopentyl-2-[4-(hexahydro-pyrrolo[1,2-a]pyrazine-2-sulfonyl)-phenyl]-N-(5-methoxy-thiazolo[5,4-b]pyridin-2-yl)-propionamide;

4-{4-[2-Cyclopentyl-1-(5-methoxy-thiazolo[5,4-b]pyridin-2-ylcarbamoyl)-ethyl]-benzenesulfonylamino}-piperidine-1-carboxylic acid ethyl ester;

3-Cyclopentyl-2-{4-[cyclopropyl-(1-methyl-piperidin-4-yl)-sulfamoyl]-phenyl}-N-(5-methoxy-thiazolo[5,4-b]pyridin-2-yl)-propionamide;
2-[4-(4-Benzyl-4,7-diaza-spiro[2.5]octane-7-sulfonyl)-phenyl]-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-{4-[4-(4-methyl-piperazin-1-yl)-piperidine-1-sulfonyl]-phenyl}-propionamide;
3-Cyclopentyl-2-[4-(4-cyclopentyl-piperazine-1-sulfonyl)-phenyl]-N-(5-methoxy-thiazolo[5,4-b]pyridin-2-yl)-propionamide;
3-Cyclopentyl-2-[4-(4,7-diaza-spiro[2.5]octane-7-sulfonyl)-phenyl]-N-(5-methoxy-thiazolo[5,4-b]pyridin-2-yl)-propionamide;
3-({4-[2-Cyclopentyl-1-(5-methoxy-thiazolo[5,4-b]pyridin-2-ylcarbamoyl)-ethyl]-benzenesulfonylamino}-methyl)-piperidine-1-carboxylic acid tert-butyl ester;
(S)-1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid;
(R)-1-{4-[2-Cyclopentyl-1-(5-methoxy-thiazolo[5,4-b]pyridin-2-ylcarbamoyl)-ethyl]-benzenesulfonyl}-pyrrolidine-2-carboxylic acid;
3-Cyclopentyl-2-{4-[4-(2-diethylamino-acetyl)-piperazine-1-sulfonyl]-phenyl}-N-(5-methoxy-thiazolo[5,4-b]pyridin-2-yl)-propionamide;
3-Cyclopentyl-N-(5-methoxy-thiazolo[5,4-b]pyridin-2-yl)-2-{4-[(piperidin-3-ylmethyl)-sulfamoyl]-phenyl}-propionamide;
2-(4-Butyrylsulfamoyl-phenyl)-3-cyclopentyl-N-(5-methoxy-thiazolo[5,4-b]pyridin-2-yl)-propionamide;
2-[4-(4-Cyanomethyl-piperazine-1-sulfonyl)-phenyl]-3-cyclopentyl-N-(5-methoxy-thiazolo[5,4-b]pyridin-2-yl)-propionamide;
3-{4-[2-Cyclopentyl-1-(5-methoxy-thiazolo[5,4-b]pyridin-2-ylcarbamoyl)-ethyl]-benzenesulfonylamino}-propionic acid ethyl ester;
3-Cyclopentyl-N-(5-methoxy-thiazolo[5,4-b]pyridin-2-yl)-2-{4-[methyl-(1-methyl-1H-imidazol-2-ylmethyl)-sulfamoyl]-phenyl}-propionamide;
3-{4-[2-Cyclopentyl-1-(5-methoxy-thiazolo[5,4-b]pyridin-2-ylcarbamoyl)-ethyl]-benzenesulfonylamino}-propionic acid;
3-Cyclopentyl-N-(5-methoxy-thiazolo[5,4-b]pyridin-2-yl)-2-{4-[3-(4-methyl-piperazin-1-yl)-3-oxo-propylsulfamoyl]-phenyl}-propionamide;
3-Cyclopentyl-2-{4-[2-(4-hydroxy-piperidin-1-yl)-ethylsulfamoyl]-phenyl}-N-(5-methoxy-thiazolo[5,4-b]pyridin-2-yl)-propionamide;
2-[4-(4-Cyclobutyl-piperazine-1-sulfonyl)-phenyl]-3-cyclopentyl-N-(5-methoxy-thiazolo[5,4-b]pyridin-2-yl)-propionamide;
2-[4-(4-Allyl-piperazine-1-sulfonyl)-phenyl]-3-cyclopentyl-N-(5-methoxy-thiazolo[5,4-b]pyridin-2-yl)-propionamide;
(1-{4-[2-Cyclopentyl-1-(5-methoxy-thiazolo[5,4-b]pyridin-2-ylcarbamoyl)-ethyl]-benzenesulfonyl}-azetidin-3-ylamino)-acetic acid;
3-Cyclopentyl-N-(5-methoxy-thiazolo[5,4-b]pyridin-2-yl)-2-[4-(2-piperidin-1-ylmethyl-phenylsulfamoyl)-phenyl]-propionamide;
3-Cyclopentyl-2-{4-[4-(2-dimethyamino-ethyl)-phenylsulfamoyl]-phenyl}-N-(5-methoxy-thiazolo[5,4-b]pyridin-2-yl)-propionamide;
3-Cyclopentyl-N-(5-methoxy-thiazolo[5, 4-b]pyridin-2-yl)-2-(4-propionylsulfamoyl-phenyl)-propionamide;

[3-({4-[2-Cyclopentyl-1-(5-methoxy-thiazolo[5,4-b]pyridin-2-ylcarbamoyl)-ethyl]-benzenesulfonylamino}-methyl)-azetidin-1-yl]-acetic acid;
3-Cyclopentyl-N-(5-methoxy-thiazolo[5,4-b]pyridin-2-yl)-2-{4-[4-(2,2,2-trifluoro-acetyl)-piperazine-1-sulfonyl]-phenyl}-propionamide;
3-Cyclopentyl-2-[4-(3-isopropylamino-azetidine-1-sulfonyl)-phenyl]-N-(5-methoxy-thiazolo[5,4-b]pyridin-2-yl)-propionamide;
3-Cyclopentyl-2-[4-(1-isopropy)-azetidin-3-ylsulfamoyl)-phenyl]-N-(5-methoxy-thiazolo[5,4-b]pyridin-2-yl)-propionamide;
3-Cyclopentyl-2-{4-[(1-isopropyl-azetidin-3-ylmethyl)-sulfamoyl]-phenyl}-N-(5-methoxy-thiazolo[5,4-b]pyridin-2-yl)-propionamide;
3-Cyclopentyl-N-(5-methoxy-thiazolo[5,4-b]pyridin-2-yl)-2-{4-[(oxazol-2-ylmethyl)-sulfamoyl]-phenyl}-propionamide;
3-Cyclopentyl-2-{4-[4-(2-methanesulfonyl-ethyl)-piperazine-1-sulfonyl]-phenyl}-N-(5-methoxy-thiazolo[5,4-b]pyridin-2-yl)-propionamide;
2-{4-[4-(3-Cyano--propyl)-piperazine-1-sulfonyl]-phenyl}-3-cyclopentyl-N-(5-methoxy-thiazolo[5,4-b]pyridin-2-yl)-propionamide;
3-Cyclopentyl-N-(5-methoxy-thiazolo[5,4-b]pyridin-2-yl)-2-[4-(tetrahydro-pyran-4-ylsulfamoyl)-phenyl]-propionamide;
3-Cyclopentyl-N-(5-methoxy-thiazolo[5,4-b]pyridin-2-yl)-2-{4-[1-(tetrahydro-pyran-4-yl)-azetidin-3-ylsulfamoyl]-phenyl}-propionamide;
4-{4-[2-Cyclopentyl-1-(5-methoxy-thiazolo[5,4-b]pyridin-2-ylcarbamoyl)-ethyl]-benzenesulfonyl}-3-hydroxymethyl-piperazine-1-carboxylic acid tert-butyl ester;
(S)-2-tert-Butoxycarbonylamino-4-{4-[2-cyclopentyl-1-(5-methoxy-thiazolo[5,4-b]pyridin-2-ylcarbamoyl)-ethyl]-benzenesulfonylamino}-butyric acid tert-butyl ester;
S)-2-Amino-4-{4-[2-cyclopentyl-1-(5-methoxy-thiazolo[5,4-b]pyridin-2-ylcarbamoyl)-ethyl]-benzenesulfonylamino}-butyric acid;
3-Cyclopentyl-2-{4-[4-(2-imidazol-1-yl-ethyl)-piperazine-1-sulfonyl]-phenyl}-N-(5-methoxy-thiazolo[5,4-b]pyridin-2-yl)-propionamide;
3-Cyclopentyl-2-[4-(2-hydroxymethyl-piperazine-1-sulfonyl)-phenyl]-N-(5-methoxy-thiazolo[5,4-b]pyridin-2-yl)-propionamide;
(4-{4-[2-Cyclopentyl-1-(5-methoxy-thiazolo[5,4-b]pyridin-2-ylcarbamoyl)-ethyl]-benzenesulfonyl}-piperazin-1-yl)-acetic acid;
3-Cyclopentyl-2-{4-[(2-methoxy-ethyl)-(1-methyl-piperidin-4-yl)-sulfamoyl]-phenyl}-N-(5-methoxy-thiazolo[5,4-b]pyridin-2-yl)-propionamide;
3-Cyclopentyl-2-{4-[(2-methoxy-ethyl)-pyridin-2-ylmethyl-sulfamoyl]-phenyl}-N-(5-methoxy-thiazolo[5,4-b]pyridin-2-yl)-propionamide hydrochloride;
3-Cyclopentyl-2-{4-[(2-hydroxy-ethyl)-(1-methyl-piperidin-4-yl)-sulfamoyl]-phenyl}-N-(5-methoxy-thiazolo[5,4-b]pyridin-2-yl)-propionamide;
2-[4-(4-Benzooxazol-2-yl-piperazine-1-sulfonyl)-phenyl]-3-cyclopentyl-N-(5-methoxy-thiazolo[5,4-b]pyridin-2-yl)-propionamide;
3-Cyclopentyl-2-[4-(furan-2-ylmethyl-methyl-sulfamoyl)-phenyl]-N-(5-methoxy-thiazolo[5,4-b]pyridin-2-yl)-propionamide;

3-Cyclopentyl-2-[4-(3-hydroxy-4,7-dihydro-5H-isoxazolo[5,4-c]pyridine-6-sulfonyl)-phenyl]-N-(5-methoxy-thiazolo[5,4-b]pyridin-2-yl)-propionamide;

2-[4-((S)-1-Benzyl-piperidin-3-ylsulfamoyl)-phenyl]-3-cyclopentyl-N-(5-methoxy-thiazolo[5,4-b]pyridin-2-yl)-propionamide;

3-Cyclopentyl-N-(5-methoxy-thiazolo[5,4-b]pyridin-2yl)-2{4-[4-(2,2,2-trifluoro-ethyl)-piperazine-1-sulfonyl]-phenyl}-propionamide;

({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-acetic acid ethyl ester hydrochloride;

3-Cyclopentyl-N-(5-methoxy-thiazolo[5,4-b]pyridin-2-yl)-2-[4-(4-pyridin-3-ylmethyl-piperazine-1-sulfonyl)-phenyl]-propionamide hydrochloride;

1-{4-[2-Cyclopentyl-1-(5-methoxy-thiazolo[5,4-b]pyridin-2-ylcarbamoyl)-ethyl]-benzenesulfonyl}-[1,4']bipiperidinyl-4-carboxylic acid ethyl ester hydrochloride;

1'-{4-[2-Cyclopentyl-1-(5-methoxy-thiazolo[5,4-b]pyridin-2-ylcarbamoyl)-ethyl]-benzenesulfonyl}-[1,4']bipiperidinyl-4-carboxylic acid hydrochloride;

3-Cyclopentyl-N-(5-methoxy-thiazolo[5,4-b)pyridin-2-yl)-2-{4-(2-(1-methyl-pyrrolidin-2-yl)-ethylsulfamoyl]-phenyl}-propionamide;

({4-[2-Cyclopentyl-1-(5-methoxy-thiazolo[5,4-b]pyridin-2-ylcarbamoyl)-ethyl]-benzenesulfonyl}-pyridin-2-ylmethyl-amino)-acetic acid;

3-({4-[2-Cyclopentyl-1-(5-methoxy-thiazolo[5,4-b]pyridin-2-ylcarbamoyl)-ethyl]-benzenesulfonyl}-furan-2-ylmethyl-amino)-propionic acid ethyl ester;

2-{4-[(2-Cyano-ethyl)-furan-2-ylmethyl-sulfamoyl]-phenyl}-3-cyclopentyl-N-(5-methoxy-thiazolo[5,4-b]pyridin-2-yl)-propionamide;

3-Cyclopentyl-2-{4-[(3-methoxy-propyl)-(1-methyl-piperidin-4-yl)-sulfamoyl]-phenyl}-N-(5-methoxy-thiazolo[5,4-b]pyridin-2-yl)-propionamide;

3-Cyclopentyl-2-{4-[(2-diethylamino-ethyl)-(1-methyl-piperidin-4-yl)-sulfamoyl]-phenyl}-N-(5-methoxy-thiazolo[5,4-b]pyridin-2-yl)-propionamide;

3-Cyclopentyl-2-{4-[(3-diethylamino-propyl)-(1-methyl-piperidin-4-yl)-sulfamoyl]-phenyl}-N-(5-methoxy-thiazolo[5,4-b]pyridin-2-yl)-propionamide;

3-({4-[2-Cyclopentyl-1-(5-methoxy-thiazolo-[5,4-b]pyridin-2-ylcarbamoyl)-ethyl]-benzenesulfonyl}-furan-2-ylmethyl-amino)-propionic acid;

3-Cyclopentyl-N-(5-methoxy-thiazolo[5,4-b]pyridin-2-yl)-2-[4-(3-phenyl-piperazine-1-sulfonyl)-phenyl]-propionamide;

3-Cyclopentyl-N-(5--methoxy-thiazolo[5,4-b]pyridin-2-yl)-2-[4-(3,3,4-trimethyl-piperazine-1-sulfonyl)-phenyl]-propionamide;

3-Cyclopentyl-2-[4-(3, 3-dimethyl-piperazine-1-sulfonyl)-phenyl]-N-(5-methoxy-thiazolo[5,4-b]pyridin-2-yl)-propionamide;

4-{4-[2-Cyclopentyl-1-(5-methoxy-thiazolo[5,4-b]pyridin-2-ylcarbamoyl)-ethyl]-beenzenesulfonyl}-piperazine-1,3-dicarboxylic acid 1-tert-butyl ester;

3-Cyclopentyl-N-(5-methoxy-thiazolo[5,4-b]pyridine-2-yl)-2-[4-(4-methyl-3-phenyl-piperazine-1-sulfonyl)-phenyl]-propionamide; and 3-Cyclopentyl-2-[4-(2,5-diaza-bicyclo[2.2.1]heptane-2-sulfonyl)-phenyl]-N-(5-methoxy-thiazolo[5,4-b]pyridin-2-yl)-propionamide;

or an enantiomer thereof; or an enantiomeric mixture thereof; or a pharmaceutically acceptable salt thereof.

11. A method for the treatment of impaired glucose tolerance, Type 2 diabetes and obesity which method comprises administering to a mammal in need thereof a therapeutically effective amount of a compound of claim 1.

12. A pharmaceutical composition comprising a therapeutically effective amount of a compound of claim 1 in combination with one or more pharmaceutically acceptable carriers.

13. A pharmaceutical composition according to claim 12 for the treatment of impaired glucose tolerance, Type 2 diabetes and obesity.

\* \* \* \* \*